US009977021B2

(12) United States Patent
Bluestone et al.

(10) Patent No.: US 9,977,021 B2
(45) Date of Patent: *May 22, 2018

(54) CD127 EXPRESSION INVERSELY CORRELATES WITH FOXP3 AND SUPPRESSIVE FUNCTION OF CD4+ TREGS

(71) Applicant: The Regents of the University of California, Oakland, CA (US)

(72) Inventors: Jeffrey A. Bluestone, San Francisco, CA (US); Weihong Liu, San Francisco, CA (US); Amy Putnam, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 410 days.

This patent is subject to a terminal disclaimer.

(21) Appl. No.: 14/666,772

(22) Filed: Mar. 24, 2015

(65) Prior Publication Data

US 2015/0192582 A1  Jul. 9, 2015

Related U.S. Application Data

(63) Continuation of application No. 11/756,479, filed on May 31, 2007, now Pat. No. 9,012,134.

(60) Provisional application No. 60/803,623, filed on May 31, 2006.

(51) Int. Cl.
| | |
|---|---|
| *G01N 33/53* | (2006.01) |
| *G01N 33/569* | (2006.01) |
| *A61K 39/00* | (2006.01) |
| *C12N 5/0783* | (2010.01) |
| *G01N 33/50* | (2006.01) |
| *A61K 35/17* | (2015.01) |
| *A61K 35/12* | (2015.01) |

(52) U.S. Cl.
CPC ....... *G01N 33/56972* (2013.01); *A61K 35/17* (2013.01); *A61K 39/0008* (2013.01); *C12N 5/0636* (2013.01); *G01N 33/505* (2013.01); *A61K 2035/122* (2013.01); *A61K 2039/515* (2013.01); *G01N 2333/70514* (2013.01); *G01N 2333/70517* (2013.01); *G01N 2333/70596* (2013.01); *G01N 2333/7155* (2013.01)

(58) Field of Classification Search
None
See application file for complete search history.

(56) References Cited

U.S. PATENT DOCUMENTS

| 5,474,897 A | 12/1995 | Weiss et al. |
| 5,543,320 A | 8/1996 | Park et al. |
| 6,797,267 B2 | 9/2004 | Horwitz |
| 9,012,134 B2 * | 4/2015 | Bluestone .......... A61K 39/0008 435/2 |
| 2005/0249701 A1 | 11/2005 | Morre et al. |
| 2006/0062763 A1 | 3/2006 | Godfrey et al. |
| 2009/0208471 A1 | 8/2009 | Yun et al. |

FOREIGN PATENT DOCUMENTS

WO    2007/014420 A1    2/2007

OTHER PUBLICATIONS

Baecher-Allan et al. (Clinical Immunology 115 (2005) 10-18).*
Liu et al. (JEM vol. 203, No. 7, Jul. 10, 2006 1701-1711).*
Baecher-Allan et al. 2004. *Seminars in Immunology* 16:89-97.
Banham, Alison "Cell-surface IL-7 receptor expression facilitates the purification of FOXP3+ regulatory T cells," Trends in Immunology, vol. 27, No. 12, 4 pp.
Baratelli et al. "Prostaglandin E2 Induces FOXP3 Gene Expression and T Regulatory Cell Function in Human CD4+ T Cells," The Journal of Immunology, 2005, vol. 175, pp. 1483-1490.
Caton et al. "CD4+CD25+Regulatory T Cell Selection," Ann. N.Y. Acad. Sci., 2004, vol. 1029, pp. 101-114.
Cozzo, C. et al., "Cutting Edge: Self-Peptides Drive the Peripheral Expansion of $CD4^+$ $CD25^+$ Regulatory T Cells[1]," *The Journal of Immunology* (2003) 171:5678-5682.
Cupedo et al. "Development and activation of regulatory T cells in the human fetus," Eur. J. Immunol., 2005, vol. 35, pp. 383-390.
Dieckmann et al. 2001. *J. Exp. Med.* 193(11):1303-1310.
Earle et al. 2005. *Clinical Immunology* 115:3-9.
Fehervari, Z. et al., "Development and function of $CD25^+$ $CD4^+$ regulatory T cells," *Current Opinion in Immunology* (2004) 16:203-208.
Fontenot et al. 2003. *Nat. Immunol.* 4(4):330-336. ePub Mar. 3, 2003.
Fontenot, J. D. et al., "Molecular aspects of regulatory T cell development," *Seminars in Immunology* (2004) 16:73-80.
Franchimont et al. 2002. *The Journal of Immunology* 168:2212-2218.
Gambineri, E., M.D. et al., "Immune dysregulation, polyendocrinopathy, enteropathy, and X-linked inheritance (IPEX), a syndrome of systemic autoimmunity caused by mutations of FOXP3, a critical regulator of T-cell homeostasis," *Current Opinion in Rheumatology* (2003) 15:430-435.
Gattinoni et al. 2005. *J. Exp. Med.* 202(7):907-912.
Gavin et al. 2002. *Nat. Immunol.* 3(1)33-41. ePub Dec. 10, 2001.
Godfrey, Wayne R. et al., "Cord blood $CD4^+CD25^+$derived T regulatory cell lines express FoxP3 protein and manifest potent suppressor function," Blood, Jan. 15, 2005, vol. 105, No. 2, pp. 750-758.

(Continued)

*Primary Examiner* — Zachary S Skelding
(74) *Attorney, Agent, or Firm* — Kilpatrick Townsend & Stockton LLP

(57) ABSTRACT

The invention provides methods of isolating $CD127^{lo/-}$ immunosuppressive regulatory T cells which can be greatly enriched for FoxP3, methods of expanding the isolated cells, pharmaceutical compositions of such cells, and methods of their use in the treatment of autoimmune and other immune system mediated disorders.

10 Claims, 21 Drawing Sheets

(56) References Cited

OTHER PUBLICATIONS

Goldsby et al. 2002. *Immunology*, 5th Ed., W.H. Freeman and Co., pp. 334-335.
Janeway et al. 2001. *Immunobiology*, 5th edition, Garland Publishing, pp. 636-637.
June et al. "Clinical application of expanded $CD4^+25^+$ cells," Seminars in Immunology, 2006, vol. 18, pp. 78-88.
Klein et al. 1997. *Immunology*, 2nd Ed., Blackwell Science, pp. 642-644.
Liu et al. "CD127 expression inversely correlates with FoxP3 and suppressive function of human $CD4^+$T reg cells," The Journal of Experimental Medicine, 2006, vol. 203, No. 7, pp. 1701-.
Miura, Y. et al., "Association of Foxp3 regulatory gene expression with graft-versus-host disease," *Blood* (Oct. 1, 2004) 104(7):2187-2193.
Paiardini et al. "Loss of CD127 Expression Defines an Expansion of Effector CD8+ T Cells in HIV-Infected Individuals," The Journal of Immunology, 2900-2909.
Parretta et al. 2005. *J. Immunol.* 174:7654-7664.
Popescu et al. 2003. *Am. J. Transplantation* 3:1369-1377.
Prince et al. 1992. *Cellular Immunology* 145:254-262.
Ramsdell, F. et al., "Transcription factors in autoimmunity," *Current Opinion in Immunology* (2003) 15:718-724.
Ramsdell, F., "Foxp3 and Natural Regulatory T Cells: Key to a Cell Lineage," *Immunity* (Aug. 2003) 19:165-168.
Seddiki et al. 2005. *Tissue Antigens* 66(5):537.
Seddiki et al. "Expression of interleukin (IL)-2 and IL-7 receptors discriminates between human regulatory and activated T cells," The Journal of Experimental Medicine, vol. 203, No. 7, pp. 1693-1700.
Sereti, Irini et al., "In vivo expansion of CD4+CD45RO-$CD25^+$ T cells expressing FoxP3 in IL-2-treated HIV-infected patients," Journal of Clinical Investigation, vol. 115, No. 7, Jul. 1, 2005, American Society for Clinical Investigation, U.S., pp. 1839-1847.
Tang et al. 2004. *J. Exp. Med.* 199(11):1455-1465.
Torgerson, T. R. et al., "Immune dysregulation, polyendocrinopathy, enteropathy, X-linked syndrome: a model of immune dysregulation," *Current Opinion in Allergy and Clinical Immunology* (2002) 2:481-487.
Walker, M. R. et al., "Induction of FoxP3 and acquisition of T regulatory activity by stimulated human $CD4^+CD25^-$T cells," *The Journal of Clinical Investigation* (Nov. 2003) 112(9):1437-1443.
Wiley Online Library, *Tissue Antigens* (Nov. 2005) 66(5):343-622.
Zorn, E. et al., "Reduced frequency of FOXP3+CD4+CD25+ regulatory T cells in patients with chronic graft-versus-host disease," *Blood* (Oct. 15, 2005) 106(8):2903-2911.
International Search Report and Written Opinion from Appl. No. PCT/US07/70143, dated Dec. 14, 2007.
The Supplementary European Search Report from EP Application No. 07 78 4254. (2009).
BD Biosciences, "Human Regulatory T Cell Analysis: A new approach using CD127, CD25, and CD4 antibodies for identification, isolation, and characterization of viable human regulatory T lymphocytes," 2006, 12 pages.

* cited by examiner

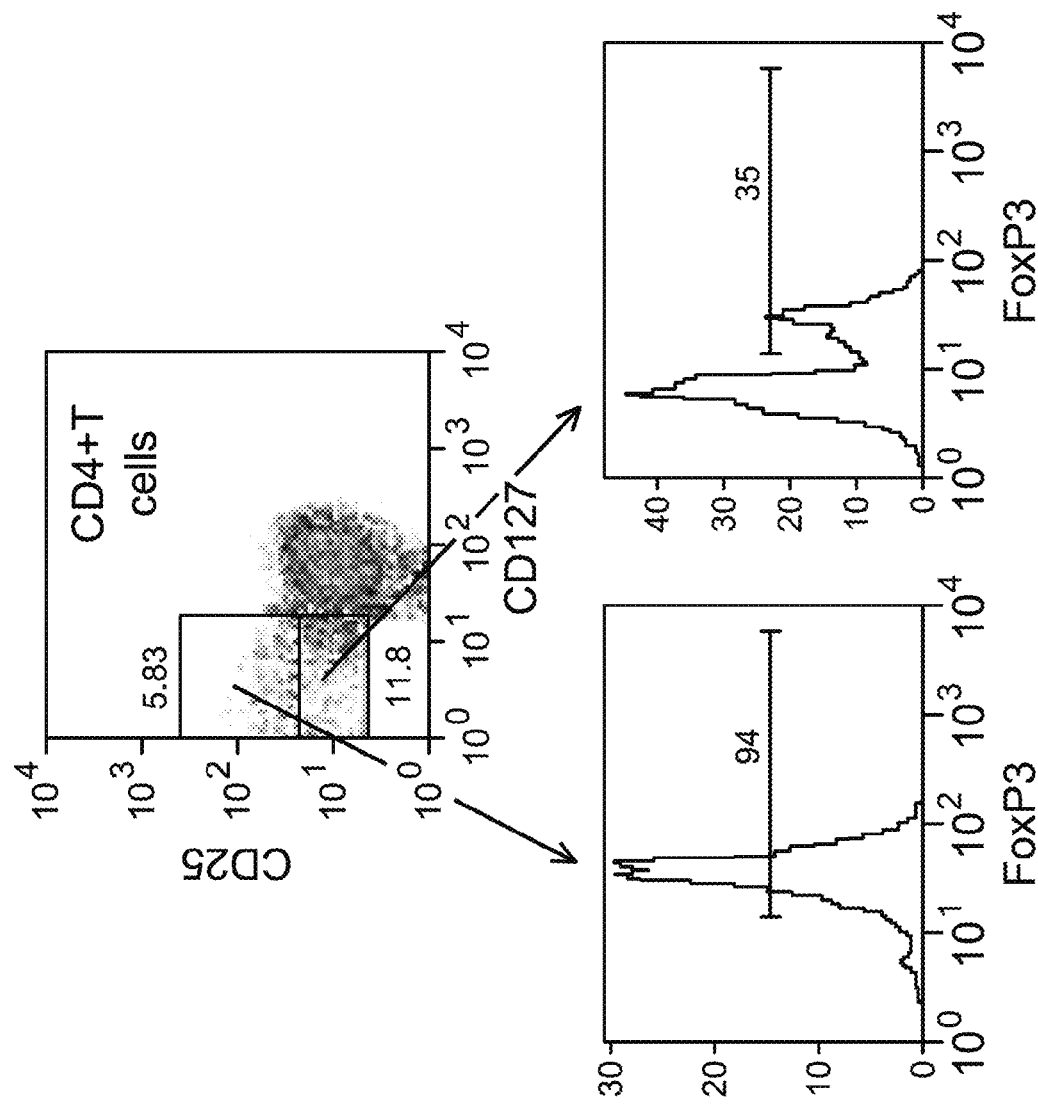

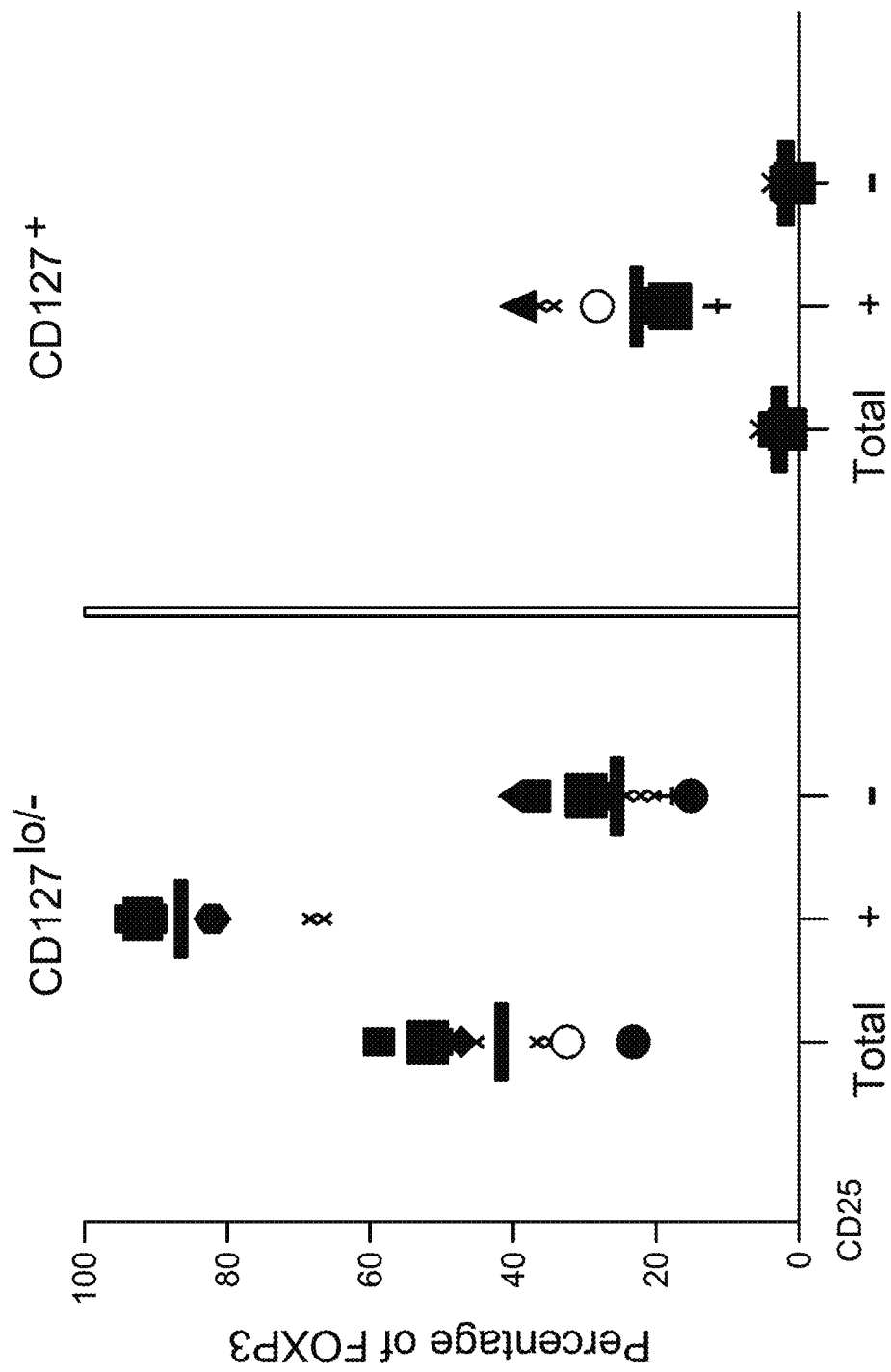

Fig. 9

CD127 or interleukin 7 receptor precursor [Homo sapiens]
Amino acid sequence

ACCESSION NP_002176 XP_942460 VERSION NP_002176.2 GI:28610151

NM_002185.2 S:CCDS3911.1

```
  1  MTILGTTFGM  VFSLLQVVSG  ESGYAQNGDL  EDAELDDYSF
 41  SCYSQLEVNG  SQHSLTCAFE  DPDVNITNLE  FEICGALVEV
 81  KCLNFRKLQE  IYFIETKKFL  LIGKSNICVK  VGEKSLTCKK
121  IDLTTIVKPE  APFDLSVVYR  EGANDFVVTF  NTSHLQKKYV
161  KVLMHDVAYR  QEKDENKWTH  VNLSSTKLTL  LQRKLQPAAM
201  YEIKVRSIPD  HYFKGFWSEW  SPSYYFRTPE  INNSSGEMDP
241  ILLTISILSF  FSVALLVILA  CVLWKKRIKP  IVWPSLPDHK
281  KTLEHLCKKP  RKNLNVSFNP  ESFLDCQIHR  VDDIQARDEV
321  EGFLQDTFPQ  QLEESEKQRL  GGDVQSPNCP  SEDVVITPES
361  FGRDSSLTCL  AGNVSACDAP  ILSSSRSLDC  RESGKNGPHV
401  YQDLLLSLGT  TNSTLPPPFS  LQSGILTLNP  VAQGQPILTS
441  LGSNQEEAYV  TMSSFYQNQ
```

Fig. 10

CD4 [Homo sapiens]. Amino acid sequence

```
 1   MNRGVPFRHL LLVLQLALLP AATQGKKVVL
31   GKKGDTVELT CTASQKKSIQ FHWKNSNQIK
61   ILGNQGSFLT K
```

FoxP3 Expression on Day 14 of Expanded CD4+CD127- Cells

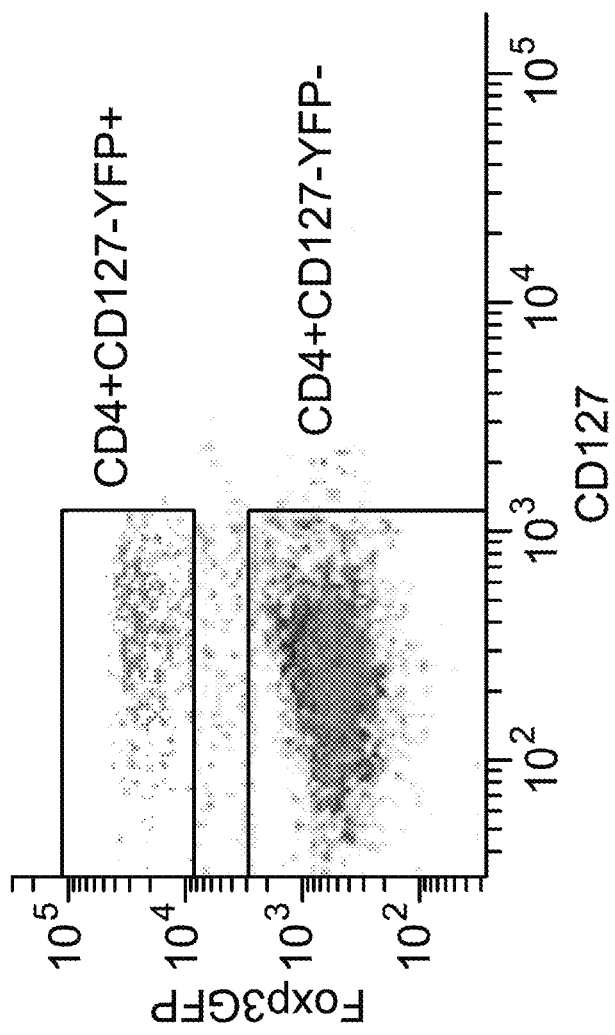

SEQUENCE LISTING

```
<160> NUMBER OF SEQ ID NOS: 42

<210> SEQ ID NO 1
<211> LENGTH: 459
<212> TYPE: PRT
<213> ORGANISM: Homo sapiens
<220> FEATURE:
<223> OTHER INFORMATION: CD127 antigen, interleukin-7 receptor (IL-7R),
      interleukin-7 receptor alpha chain (IL-7R-alpha)

<400> SEQUENCE: 1

Met Thr Ile Leu Gly Thr Thr Phe Gly Met Val Phe Ser Leu Leu Gln
 1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
        50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Val Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190
```

-continued

Arg Lys Leu Gln Pro Ala Ala Met Tyr Glu Ile Lys Val Arg Ser Ile
            195                 200                 205
Pro Asp His Tyr Phe Lys Gly Phe Trp Ser Glu Trp Ser Pro Ser Tyr
        210                 215                 220
Tyr Phe Arg Thr Pro Glu Ile Asn Asn Ser Ser Gly Glu Met Asp Pro
225                 230                 235                 240
Ile Leu Leu Thr Ile Ser Ile Leu Ser Phe Phe Ser Val Ala Leu Leu
                245                 250                 255
Val Ile Leu Ala Cys Val Leu Trp Lys Lys Arg Ile Lys Pro Ile Val
            260                 265                 270
Trp Pro Ser Leu Pro Asp His Lys Lys Thr Leu Glu His Leu Cys Lys
        275                 280                 285
Lys Pro Arg Lys Asn Leu Asn Val Ser Phe Asn Pro Glu Ser Phe Leu
290                 295                 300
Asp Cys Gln Ile His Arg Val Asp Asp Ile Gln Ala Arg Asp Glu Val
305                 310                 315                 320
Glu Gly Phe Leu Gln Asp Thr Phe Pro Gln Gln Leu Glu Glu Ser Glu
                325                 330                 335
Lys Gln Arg Leu Gly Gly Asp Val Gln Ser Pro Asn Cys Pro Ser Glu
            340                 345                 350
Asp Val Val Ile Thr Pro Glu Ser Phe Gly Arg Asp Ser Ser Leu Thr
        355                 360                 365
Cys Leu Ala Gly Asn Val Ser Ala Cys Asp Ala Pro Ile Leu Ser Ser
370                 375                 380
Ser Arg Ser Leu Asp Cys Arg Glu Ser Gly Lys Asn Gly Pro His Val
385                 390                 395                 400
Tyr Gln Asp Leu Leu Leu Ser Leu Gly Thr Thr Asn Ser Thr Leu Pro
                405                 410                 415
Pro Pro Phe Ser Leu Gln Ser Gly Ile Leu Thr Leu Asn Pro Val Ala
            420                 425                 430
Gln Gly Gln Pro Ile Leu Thr Ser Leu Gly Ser Asn Gln Glu Glu Ala
        435                 440                 445
Tyr Val Thr Met Ser Ser Phe Tyr Gln Asn Gln
    450                 455

<210> SEQ ID NO 2
<211> LENGTH: 71
<212> TYPE: PRT
<213> ORGANISM: Homo sapiens
<220> FEATURE:
<223> OTHER INFORMATION: CD4 antigen, T cell receptor (TCR) co-receptor

<400> SEQUENCE: 2

Met Asn Arg Gly Val Pro Phe Arg His Leu Leu Leu Val Leu Gln Leu
  1               5                  10                  15
Ala Leu Leu Pro Ala Ala Thr Gln Gly Lys Lys Val Val Leu Gly Lys
                20                  25                  30
Lys Gly Asp Thr Val Glu Leu Thr Cys Thr Ala Ser Gln Lys Lys Ser
            35                  40                  45
Ile Gln Phe His Trp Lys Asn Ser Asn Gln Ile Lys Ile Leu Gly Asn
        50                  55                  60
Gln Gly Ser Phe Leu Thr Lys
65                  70

<210> SEQ ID NO 3

```
<211> LENGTH: 17
<212> TYPE: PRT
<213> ORGANISM: Artificial Sequence
<220> FEATURE:
<223> OTHER INFORMATION: synthetic transferrin (119-) autoantigen
      peptide

<400> SEQUENCE: 3

Val Val Lys Lys Gly Thr Asp Phe Gln Leu Asn Gln Leu Glu Gly Lys
1               5                   10                  15

Lys

<210> SEQ ID NO 4
<211> LENGTH: 16
<212> TYPE: PRT
<213> ORGANISM: Artificial Sequence
<220> FEATURE:
<223> OTHER INFORMATION: synthetic transferrin (119-) autoantigen
      peptide

<400> SEQUENCE: 4

Val Val Lys Lys Gly Thr Asp Phe Gln Leu Asn Gln Leu Gly Lys Lys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetic kappa-A-beta (37-51 major; 37-52
      minor) autoantigen peptide

<400> SEQUENCE: 5

Tyr Val Arg Phe Asp Ser Asp Val Gly Glu Tyr Arg Ala Val Thr Glu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetic lysozyme c (48-63) autoantigen
      peptide

<400> SEQUENCE: 6

Gly Asp Gln Ser Thr Asp Tyr Gly Ile Phe Gln Ile Asn Ser Arg Tyr
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: synthetic nucleoporin NUP155 (120-)
      autoantigen peptide

<400> SEQUENCE: 7

Arg Gln Val Arg Phe Tyr Ser Gly Val Ile Glu Leu
1               5                   10

<210> SEQ ID NO 8
<211> LENGTH: 15
<212> TYPE: PRT
<213> ORGANISM: Artificial Sequence
<220> FEATURE:
<223> OTHER INFORMATION: synthetic saposin D (37-) autoantigen peptide

<400> SEQUENCE: 8
```

Leu Pro Asp Pro Tyr Gln Lys Gln Cys Asp Asp Phe Val Ala Glu
1               5                   10                  15

<210> SEQ ID NO 9
<211> LENGTH: 13
<212> TYPE: PRT
<213> ORGANISM: Artificial Sequence
<220> FEATURE:
<223> OTHER INFORMATION: synthetic 26S proteasome p112 (224-)
      autoantigen peptide

<400> SEQUENCE: 9

Ile Phe Leu Asp Asp Pro Gln Ala Val Ser Asp Val Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic 14-3-3 protein beta, delta, eta,
      theta or tau (95-) autoantigen peptide

<400> SEQUENCE: 10

Lys Thr Ala Phe Asp Glu Ala Ile Ala Glu Leu Asp
1               5                   10

<210> SEQ ID NO 11
<211> LENGTH: 20
<212> TYPE: PRT
<213> ORGANISM: Artificial Sequence
<220> FEATURE:
<223> OTHER INFORMATION: synthetic kappa-A-beta (146-) autoantigen
      peptide

<400> SEQUENCE: 11

Ser Thr Gln Leu Ile Arg Asn Gly Asp Trp Thr Phe Gln Val Leu Val
1               5                   10                  15

Met Leu Glu Met
            20

<210> SEQ ID NO 12
<211> LENGTH: 20
<212> TYPE: PRT
<213> ORGANISM: Artificial Sequence
<220> FEATURE:
<223> OTHER INFORMATION: synthetic kappa-A-beta (110-) autoantigen
      peptide

<400> SEQUENCE: 12

His His Asn Thr Leu Val Cys Ser Val Thr Asp Phe Tyr Pro Ala Lys
1               5                   10                  15

Ile Lys Val Arg
            20

<210> SEQ ID NO 13
<211> LENGTH: 20
<212> TYPE: PRT
<213> ORGANISM: Artificial Sequence
<220> FEATURE:
<223> OTHER INFORMATION: synthetic Ig gamma 1-chain (141-) autoantigen
      peptide

<400> SEQUENCE: 13

Ser Met Val Thr Leu Gly Cys Leu Val Lys Gly Tyr Phe Pro Glu Pro
1               5                   10                  15

Val Thr Val Thr
            20

<210> SEQ ID NO 14
<211> LENGTH: 15
<212> TYPE: PRT
<213> ORGANISM: Artificial Sequence
<220> FEATURE:
<223> OTHER INFORMATION: synthetic insulin B ss5-15 aa1-15 autoantigen
      peptide

<400> SEQUENCE: 14

Phe Val Asn Gln His Leu Cys Gly Ser His Leu Val Glu Ala Leu
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      271-285 autoantigen peptide

<400> SEQUENCE: 15

Pro Arg Leu Ile Ala Phe Thr Ser Glu His Ser His Phe Ser Leu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      116-130 autoantigen peptide

<400> SEQUENCE: 16

Asn Ile Leu Leu Gln Tyr Val Val Lys Ser Phe Asp Arg Ser Thr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      356-370 autoantigen peptide

<400> SEQUENCE: 17

Lys Tyr Lys Ile Trp Met His Val Asp Ala Ala Trp Gly Gly Gly
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: sythethic glutamic acid decarboxylase (GAD65)
      376-390autoantigen peptide

<400> SEQUENCE: 18

Lys His Lys Trp Lys Leu Asn Gly Val Glu Arg Ala Asn Ser Val
1               5                   10                  15

<210> SEQ ID NO 19
<211> LENGTH: 15
<212> TYPE: PRT
<213> ORGANISM: Artificial Sequence

```
<220> FEATURE:
<223> OTHER INFORMATION: synthetic glutamic acid decarboxylase (GAD65)
      481-495 autoantigen peptide

<400> SEQUENCE: 19

Leu Tyr Asn Ile Ile Lys Asn Arg Glu Gly Tyr Glu Met Val Phe
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      511-525 autoantigen peptide

<400> SEQUENCE: 20

Pro Ser Leu Arg Val Leu Glu Asp Asn Glu Glu Arg Met Ser Arg
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      546-560 autoantigen peptide

<400> SEQUENCE: 21

Ser Tyr Gln Pro Leu Gly Asp Lys Val Asn Phe Phe Arg Met Val
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      556-570 autoantigen peptide

<400> SEQUENCE: 22

Phe Phe Arg Met Val Ile Ser Asn Pro Ala Ala Thr His Gln Asp
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      566-580 autoantigen peptide

<400> SEQUENCE: 23

Ala Thr His Gln Asp Ile Asp Phe Leu Ile Glu Glu Ile Glu Arg
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic glutamic acid decarboxylase (GAD65)
      206-220 autoantigen peptide

<400> SEQUENCE: 24

Thr Tyr Glu Ile Ala Pro Val Phe Val Leu Leu Glu Tyr Val Thr
 1               5                  10                  15
```

<210> SEQ ID NO 25
<211> LENGTH: 16
<212> TYPE: PRT
<213> ORGANISM: Artificial Sequence
<220> FEATURE:
<223> OTHER INFORMATION: synthetic muscle nicotinic acetylcholine
      receptor (AChR) 121-126 autoantigen peptide

<400> SEQUENCE: 25

Pro Ala Ile Phe Lys Ser Tyr Cys Glu Ile Ile Val Thr His Phe Pro
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: synthetic muscle nicotinic acetylcholine
      receptor (AChR) 129-145 autoantigen peptide

<400> SEQUENCE: 26

Glu Ile Ile Val Thr His Phe Pro Phe Asp Glu Gln Asn Cys Ser Met
1               5                   10                  15

Lys

<210> SEQ ID NO 27
<211> LENGTH: 18
<212> TYPE: PRT
<213> ORGANISM: Artificial Sequence
<220> FEATURE:
<223> OTHER INFORMATION: synthetic muscle nicotinic acetylcholine
      receptor (AChR) 195-212 autoantigen peptide

<400> SEQUENCE: 27

Asp Thr Pro Tyr Leu Asp Ile Thr Tyr His Phe Val Met Gln Arg Leu
1               5                   10                  15

Pro Leu

<210> SEQ ID NO 28
<211> LENGTH: 13
<212> TYPE: PRT
<213> ORGANISM: Artificial Sequence
<220> FEATURE:
<223> OTHER INFORMATION: synthetic cartilage glycoprotein-39 (YKL40)
      259-271 autoantigen peptide

<400> SEQUENCE: 28

Pro Thr Phe Gly Arg Ser Phe Thr Leu Ala Ser Ser Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: synthetic myelin oligodendrocyte glycoprotein
      (MOG) 97-108 autoantigen peptide

<400> SEQUENCE: 29

Thr Cys Phe Phe Arg Asp His Ser Tyr Gln Glu Glu
1               5                   10

<210> SEQ ID NO 30
<211> LENGTH: 9
<212> TYPE: PRT
<213> ORGANISM: Artificial Sequence

```
<220> FEATURE:
<223> OTHER INFORMATION: synthetic myelin basic protein (MBP) 111-119
      autoantigen peptide

<400> SEQUENCE: 30

Ser Leu Ser Arg Phe Ser Trp Gly Ala
1               5

<210> SEQ ID NO 31
<211> LENGTH: 9
<212> TYPE: PRT
<213> ORGANISM: Artificial Sequence
<220> FEATURE:
<223> OTHER INFORMATION: synthetic myelin basic protein (MBP) 87-95
      autoantigen peptide

<400> SEQUENCE: 31

Val Val His Phe Phe Lys Asn Ile Val
1               5

<210> SEQ ID NO 32
<211> LENGTH: 14
<212> TYPE: PRT
<213> ORGANISM: Artificial Sequence
<220> FEATURE:
<223> OTHER INFORMATION: synthetic anion channel protein band 3 861-874
      Autoantigen peptide

<400> SEQUENCE: 32

Cys Leu Ala Val Leu Trp Val Val Lys Ser Thr Pro Ala Ser
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic S-antigen 341-354 autoantigen peptide

<400> SEQUENCE: 33

Phe Leu Gly Glu Leu Thr Ser Ser Glu Val Ala Thr Glu Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic HLA-B(B27PD) 125-138 autoantigen
      peptide

<400> SEQUENCE: 34

Ala Leu Asn Glu Asp Leu Ser Ser Gln Thr Ala Ala Asp Thr
1               5                   10

<210> SEQ ID NO 35
<211> LENGTH: 20
<212> TYPE: DNA
<213> ORGANISM: Artificial Sequence
<220> FEATURE:
<223> OTHER INFORMATION: synthetic ligation-mediated PCR (LMPCR) IL-7R
      promoter 5'-primer

<400> SEQUENCE: 35
cagggaatat ccaggaggaa                                               20

<210> SEQ ID NO 36
```

```
<211> LENGTH: 22
<212> TYPE: DNA
<213> ORGANISM: Artificial Sequence
<220> FEATURE:
<223> OTHER INFORMATION: synthetic ligation-mediated PCR (LMPCR) IL-7R
      promoter 3'-primer

<400> SEQUENCE: 36
tgtgtgagcc agtgtgtatg aa                                               22

<210> SEQ ID NO 37
<211> LENGTH: 21
<212> TYPE: DNA
<213> ORGANISM: Artificial Sequence
<220> FEATURE:
<223> OTHER INFORMATION: synthetic ligation-mediated PCR (LMPCR) IL-7R
      2K upstream 5'-primer

<400> SEQUENCE: 37
tttgggattt ctccttgaac a                                                21

<210> SEQ ID NO 38
<211> LENGTH: 20
<212> TYPE: DNA
<213> ORGANISM: Artificial Sequence
<220> FEATURE:
<223> OTHER INFORMATION: synthetic ligation-mediated PCR (LMPCR) IL-7R
      2K upstream 3'-primer

<400> SEQUENCE: 38
tctctgggca tttcaaaacc                                                  20

<210> SEQ ID NO 39
<211> LENGTH: 20
<212> TYPE: DNA
<213> ORGANISM: Artificial Sequence
<220> FEATURE:
<223> OTHER INFORMATION: synthetic ligation-mediated PCR (LMPCR) IL-7R
      intron 4 5'-primer

<400> SEQUENCE: 39
gaggtggcag aagagtggag                                                  20

<210> SEQ ID NO 40
<211> LENGTH: 20
<212> TYPE: DNA
<213> ORGANISM: Artificial Sequence
<220> FEATURE:
<223> OTHER INFORMATION: synthetic ligation-mediated PCR (LMPCR) IL-7R
      intron 4 3'-primer

<400> SEQUENCE: 40
tgcatcacac tgcaaacaaa                                                  20

<210> SEQ ID NO 41
<211> LENGTH: 20
<212> TYPE: DNA
<213> ORGANISM: Artificial Sequence
<220> FEATURE:
<223> OTHER INFORMATION: synthetic ligation-mediated PCR (LMPCR) IL-7R
      intron 7 and exon 8 5'-primer

<400> SEQUENCE: 41
acatgctggc aattctgtga                                                  20

<210> SEQ ID NO 42
<211> LENGTH: 20
```

```
<212> TYPE: DNA
<213> ORGANISM: Artificial Sequence
<220> FEATURE:
<223> OTHER INFORMATION: synthetic ligation-mediated PCR (LMPCR) IL-7R
      intron 7 and exon 8 3'-primer

<400> SEQUENCE: 42
tctggcagtc caggaaactt                                                     20
```

CD127 EXPRESSION INVERSELY CORRELATES WITH FOXP3 AND SUPPRESSIVE FUNCTION OF CD4+ TREGS

CROSS-REFERENCES TO RELATED APPLICATIONS

This application is a continuation of U.S. application Ser. No. 11/756,479, filed May 31, 2007, which claims the benefit of U.S. Provisional Application Ser. No. 60/803,623 filed May 31, 2006 each of which is incorporated by reference in its entirety for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file SEQTXT_81906-939479-171820US.txt, created on Mar. 23, 2015, 16,109 bytes, machine format IBM-PC, MS-Windows operating system, is hereby incorporated by reference in its entirety for all purposes.

BACKGROUND OF THE INVENTION

Over the past decade, there have been tremendous advances in our understanding of the basic process that control immune tolerance. The identification of regulatory T cells (Treg), particularly $CD4^+CD25^+$ Tregs, as an important component of self-tolerance has opened a major area of investigation in immunology, and numerous studies have demonstrated the potent influence of Tregs in suppressing pathologic immune responses in autoimmune diseases, transplantation, and graft-vs-host disease (reviewed in (1-6)). Tregs have a unique and robust therapeutic profile. The cells require specific T cell receptor (TCR)-mediated activation to develop regulatory activity but their effector function appears to be non-specific, regulating local inflammatory responses through a combination of cell-cell contact and suppressive cytokine production (7-9). Moreover, there are a number of therapeutic interventions that appear to promote Treg development and function (10, 11). This, so called "adaptive" regulatory T cell population, share many of the attributes of thymic-dependent, natural Tregs but can differ in critical cell surface biomarkers and functional attributes (12). For instance, Tr1 and Th3 cells have been described that produce IL-10 and TGFβ, respectively (13, 14). These results have led to novel approaches to immunotherapy as the ability to isolate and expand this cell subset in mice has led to novel therapeutic interventions in immunological diseases (6, 15). However, a major obstacle to the study and application of Tregs in the human setting has been the lack of specific cell surface biomarkers to define and separate Tregs from other regulatory or effector T cell subsets.

Although many studies indicate that CD25 is a crucial cell-surface marker for the regulatory subset (16, 17), unlike the mouse, several studies have suggested that only the $CD4^+$ T cell subset expressing the highest levels of CD25 (termed $CD25^{hi}$) have in vitro suppressive activity (16). Moreover, the addition of other markers such as HLA-DR suggest even a lower percentage (often less than 1%) of $CD4^+$ T cells comprise the suppressive T cell subset. Finally, some markers such as CTLA-4 and GITR, which have been reported to be expressed on Tregs (18-21), are also expressed on potent effector T cells and as such make immunophenotyping and determination of their functional role problematic (22, 23). This has led to a number of disparate reports of Treg quantification in disease settings. For instance, some studies suggest that the number of $CD4^+CD25^{hi}$ Tregs are deficient in Type 1 Diabetes (T1D) (24) while others suggest that the number and function of these cells is normal in T1D (25). Moreover, the ability to isolate only limited numbers of these cells from peripheral blood has made expanding this regulatory cell population problematic.

One significant advance in the study of mouse and human Tregs has been the discovery of the transcription factor, FoxP3, as a major marker and functional regulator of Treg development and function (26-29). In a series of elegant mouse and human genetic studies, investigators demonstrated that mutations in the FoxP3 gene were linked to the autoimmune manifestations observed in the Scurfy mouse and humans with immune dysregulation, polyendocrinopathy, enteropathy, X linked syndrome (IPEX) disease (28). Subsequent studies in the mouse showed that FoxP3 deficient animals lack Tregs while over-expression of the FoxP3 protein leads to profound immune suppression (30). Although recent studies have questioned whether all Tregs are $FoxP3^+$ or whether all $FoxP3^+$ T cells are regulatory, FoxP3 protein remains the best and most specific marker of Tregs to date (30).

In this regard, flow cytometric and immunohistochemical analyses that FoxP3 is expressed in significantly more T cells than previously identified using the other available cell surface markers, including CD25. FoxP3 protein is found in CD25 low and negative $CD4^+$ T cells and, under certain conditions, some $CD8^+$ T cells (30, 31). Thus, it is likely that many of the natural and adaptive regulatory T cells are missed in current biomarker studies, calling into question the conclusions related to deficiencies or defects in certain autoimmune settings. Importantly, as FoxP3 is an intracellular protein, it cannot be used to separate human Tregs for functional studies or for in vivo expansion for cellular therapy, limiting its use in the human setting.

As noted above, the emergence of Tregs as an essential pathway in maintaining immune tolerance has opened the opportunity for a better understanding of immune homeostasis and the potential for therapeutic intervention. However, the human phenotyping of Tregs has been complex. Typically, investigators have noted that the most suppressive Tregs coincide with the $CD4^+$ T cells with the brightest CD25 staining. Recently, Cozzo et al (see, J Immunol. 2003 Dec. 1; 171(11):5678-82) have reported that $CD4^+CD25^+$ regulatory T cells express low levels of CD127 in a transgenic mouse. Hamaha et al. have reported in the context of Type 1 diabetes data indicating that $CD4^+CD25^+$ T cells express higher levels of CD127 (IL-7R alpha) than $CD4^+CD25^-$ cells. However, these results were again derived from mice, specifically NOD-SCID mice reconstituted with ex vivo engineered dendritic cells and NOD splenocytes (see, Hamaha, J et al. Diabetes 2006 January; 55(1):158-70). Unfortunately, the ability to accurately gate for CD25 is rather arbitrary as no other cell surface marker can be used to definitively identify the subset. Recently, Baecher-Allen has suggested that other markers such as HLA-DR allows for subdividing the $CD4^+CD25^{hi}$ subset to enrich Treg activity even further. However, this additional marker suggests that the number of Tregs is even less than previously suggested (41).

The identification of FoxP3 as a specific transcription factor that marks these suppressive T cells suggests that there may be a larger population of Tregs in human peripheral blood than previously appreciated, although this has been controversial due to unanticipated expression of FoxP3 in a number of activated CD25− T cell populations (30, 38). In fact, there may be regulatory cells that are Foxp3 negative as well. However, these studies have been compromised by the absence of cell surface markers that can be used to isolate these and other T cell subsets to examine regulatory T cell activity since FoxP3 cannot be used as a means to purify the cells for function.

This invention provides for these and other needs by using the reduced expression of the CD127 T-cell surface marker as a useful surrogate for identifying regulatory T-cells which are highly likely to be immunosuppressive FoxP3$^+$ regulatory T-cells. Use of the CD127 biomarker alone or in conjunction with other biomarkers can account for up to 7-8% of CD4$^+$ T cells, providing yields significantly greater than identified by previous approaches. Moreover, CD127$^{lo/-}$ cells suppress the proliferative response of alloreactive T cells in an MLR and are themselves anergic to the same stimuli. This is true in spite of the fact that in most individuals only 20-40% of the CD4+CD127lo/− cells are Foxp3$^+$"

BRIEF SUMMARY OF THE INVENTION

The invention relates to the discovery that CD127 is a particularly useful biomarker in identifying immunosuppressive regulatory T cells, including particularly, FoxP3$^+$ regulatory T-cells, in biological samples. Accordingly, in a first aspect, the invention provides methods of identifying whether a regulatory T-cell is an immunosuppressive regulatory T-cell by determining the level of expression of CD127 by the cell. In some embodiments, the invention provides methods of determining whether a regulatory T-cell in an enriched T-cell sample is highly likely to be a FoxP3$^+$ immunosuppressive T regulatory cell by detecting only one common determinant or cell surface antigen of the T-cell, CD127. In other embodiments, the invention provides methods of identifying immunosuppressive regulatory T-cells by identifying CD4$^+$CD127$^{lo/-}$ T cells according to their level of expression of the CD4 and CD127 biomarkers in a biological sample. In some embodiments, the invention provides methods of identifying immunosuppressive regulatory T-cells in a sample by identifying CD8$^+$CD127$^{lo/-}$ T cells according to their level of expression of the CD8 and CD127 biomarkers. In some embodiments, the invention provides methods of selecting or isolating the cells so identified. In some embodiments, the samples comprise T cells and are obtained from blood (e.g., isolated from PBMC), lymphoid, thymus or any specific tissues/organ sample of interest. These tissues or organs would include the pancreas, eye, heart, liver, nerves, intestine, skin, muscle, and joints.

In a second aspect, the invention, provides methods of making an isolated population of an immunosuppressive regulatory T-cells which are substantially FoxP3$^+$ or include FoxP3$^+$ T-cells. In one embodiment, the population is made by obtaining a biological sample comprising regulatory T-cells including CD127$^{lo/-}$ and CD127$^+$ cells and determining the level of expression of CD4 and/or the CD8 and CD127, on the surface of the T-cells and isolating the immunosuppressive CD4$^+$CD127$^{Lo/-}$, CD4$^+$CD8$^+$CD127$^{lo/-}$ or CD8$^+$CD127$^{lo/-}$ T-cells from those T-cells which are CD127$^+$. In some embodiments, the isolated population is obtained by providing an enriched T-cell sample and determining the level of expression of only one common determinant, CD127, on cells in the enriched sample and isolating CD127$^{lo/-}$ cells from the enriched T-cell sample. In some preferred embodiments, the isolated population is substantially CD8$^+$CD127$^{lo/-}$ T cells and/or CD4$^+$CD127$^{lo/-}$ T cells. In some additional embodiments, the isolated population is substantially CD8$^+$CD127$^{lo/-}$ T cells and/or CD4$^+$CD127$^{lo/-}$ T cells which are FoxP3$^+$ cells. The cells bearing the markers can be isolated, for instance, by the use of labeled antibodies or ligands with FACS or magnetic particles/bead technologies as known to one of ordinary skill in the art. Accordingly, in some embodiments, the invention provides a method of identifying immunosuppressive regulatory T-cells in a sample by screening T-cells in said sample to detect CD127$^{lo/-}$ T-cells; and then identifying said detected CD127$^{lo/-}$ T-cells as immunosuppressive regulatory T-cells. In some further embodiments, the identified immunosuppressive regulatory T-cells are isolated from the CD127$^+$ cells. In some embodiments, the isolated identified cells taken together provide a population of immunosuppressive regulatory T-cells for use according to the invention.

In a third aspect, the invention provides methods of making expanded populations of isolated immunosuppressive regulatory T-cell populations which are substantially FoxP3$^+$ by expanding an isolated T-cell population obtained by the above methods. In some embodiments, the isolated FoxP3$^+$ T cell population is expanded by contacting the isolated T-cells of the population with antigen, alloantigen, or anti-CD3/anti-CD28 antibodies in the presence of IL-2 plus TGFbeta or rapamycin. Alternatively, in this aspect, the T-cells in the biological sample can first be expanded and then isolated by the above methods. In some preferred embodiment, the isolated expanded population is substantially CD8$^+$CD127$^{lo/-}$ T cells and/or CD4$^+$CD127$^{lo/-}$ T cells which are FoxP3$^+$ cells.

In yet another aspect the invention provides methods of modulating an immune response in a subject, wherein the isolated or expanded, isolated immunosuppressive regulatory T-cell populations obtained by the above methods are administered to the subject.

In still another aspect, the invention provides, pharmaceutical compositions comprising isolated or expanded immunosuppressive FoxP3$^+$ T-cell populations obtained according to the above methods.

In another aspect, the invention provides methods for producing an antigen-specific or non-specific regulatory T cell enriched composition, and resultant compositions and methods of use. In one embodiment, the invention provides a method of modulating an immune reaction in a subject, said method comprising (a) obtaining a population of antigen specific or non-specific subject-compatible cells including CD4$^+$ and CD4$^-$ cells and CD127$^+$ and CD127$^-$ cells and CD25$^+$ and CD25$^-$ cells; (b) producing an antigen-specific or non-specific regulatory CD127$^{lo/-}$ or FoxP3$^+$ T cell enriched composition from said population of cells by sorting the cells on the basis of their levels of expression of the CD127 antigen and the CD4 antigen or the CD127 antigen and the CD8 antigen, or the CD4, CD8, and CD127 antigens and (c) introducing said composition into said subject to modulate said immune reaction in said subject. In some preferred embodiments, the immune response is an autoimmune response and the antigen is an autoantigen. In preferred embodiments, the cells are not sorted by their levels of expression of the CD25 common determinant.

In other aspects, the selection of the regulatory T-cell according to the level of expression of common determinant 127 comprises selections based upon one or more additional common determinants (e.g., CD4, CD8, and CD25) under the CD system (CD stands for cluster of designation) for classifying monoclonal antibodies and their specific antigens was established at the first workshop on leukocyte differentiation antigens (Paris: 1982), where the rule was also introduced that at least two mAbs that recognize the same molecule are required in order to assign a new CD. It was further recommended that the term CD be used for the clustered antibodies and the term CD molecule or CD antigen be used for antigens. Accordingly, the invention also provides methods for producing an antigen-specific regulatory T cell enriched composition, and resultant compositions and methods of use. In one embodiment, for instance, the invention provides a method of modulating an immune reaction in a subject, said method comprising (a) obtaining a population of subject-compatible cells containing $CD4^+$ and $CD4^-$ cells and $CD127^+$ and $CD127^-$ cells and $CD25^+$ and $CD25^-$ cells; (b) producing an antigen-specific regulatory $CD4^+CD127^{lo/-}$ T cell enriched composition from said population of cells by identifying and isolating cells according to their expression of both CD4, CD25 and CD127 and (c) introducing said composition into said subject to modulate said immune reaction in said subject. In some embodiments, $CD4^+CD127^{lo/-}$ T cell enriched composition is substantially $CD25^+$ enriched population obtained by also identifying and isolating the regulatory T cells according to their level of expression of CD25 wherein $CD25^+$ and $CD25^{hi}$ cells are both positively selected for. The identifying and isolating can proceed in any order or simultaneously by the use, for instance, of multiple, distinguishable fluorophores as labels on the antibodies used to detect the common determinants.

In another embodiment, for instance, the invention provides a method of modulating an immune reaction in a subject, said method comprising (a) obtaining a population of subject-compatible cells containing $CD127^+$ and $CD127^-$ cells and $CD25^{hi/+}$ and $CD25^-$ cells; (b) producing an antigen-specific regulatory $CD25^{hi/+/lo}CD127^{lo/-}$ or $CD25^{hi/+}CD127^{lo/-}$ or $CD25^{hi}CD127^{lo/-}$ T cell enriched composition from said population of cells by identifying and isolating cells according to their expression of both CD25 and CD127 and (c) introducing said composition into said subject to modulate said immune reaction in said subject.

In still a further aspect, the invention provides kits comprising materials useful in performing the above methods. A kit for isolating an immunosuppressive T-cell population, for instance, can comprise a ligand or antibody which binds CD127. The ligand or antibody is preferably labeled (e.g., a fluorescent or colored label or magnetic bead label) or a label to detect a cell bound by the ligand or antibody is provided with the kit (e.g., fluorescently labeled or magnetically labeled antibody which binds to the CD127 antibody). In some embodiments, the kit would further provide instructions for obtaining an immunosuppressive T-cell population by use of the kits contents and positive selection of T-reg cells which are low and/or negative CD127 expressers. In some embodiments, the kit instructions would set forth CD127 as a selection marker along with CD4 and/or CD25 as positive selection markers. In some embodiments, the kit provides a single CD127 antibody for use in selecting for T-reg cells which are low and/or negative CD127 expressers. In some embodiments, monoclonal antibodies for each of CD127 and CD4 and also optionally CD25 would be provided in the kit. These antibodies may be labeled (e.g., attached to a fluorescent label or magnetic label). In addition, the kit of could further provide instructions for obtaining a T-cell population for use in suppressing an immune response and optionally, further, instructions for formulating the obtained population in a suitable media for contacting with cells in vivo or in vitro. In some embodiments, of any of the above, the antibodies in the kit are not labeled, but the kit additionally provides means for labeling the antibodies (e.g., labeled antibodies which bind to an antibody used to bind CD127). In some further embodiments of any of the above, there is a proviso that the kit does not contain a means or antibody for detecting CD25. In some embodiments, the isolated population of cells, has not been directly selected against having $CD25^-$ and/or $CD25^{lo}$ cells. In some further embodiments, of any of the above, the kit provides further instruction for separating the cells using a FACS (fluorescence activated cell sorter) in the case where a fluorescent label is used or magnetism in the case where magnetic particles or beads are used as the label.

In still another aspect, the invention provides methods for identifying immunosuppressive drugs by determining their effect on only one T-cell surface marker, CD127, or on a plurality of markers including CD127 and optionally one or the other or both of CD4 and CD25. In some preferred embodiments, the assay is conducted using Tregs from an enriched T-cell sample.

With regard to any of the above aspects having embodiments wherein selection on the basis of the expression level of CD25 is not excluded subject matter, in preferred embodiments of such the selection of the regulatory T-cell positively selects cells which are $CD25^+$ or $CD25^{lo}$ in addition to cells which are $CD25^{hi}$. With regard to any of the above aspects having embodiments wherein selection on the basis of the expression level of CD25 is not excluded subject matter, in other embodiments of such selection on the basis of CD25 expression levels is excluded.

With regard to any of the above aspects having embodiments wherein steps are provided, the steps may be performed in any order, sequentially or contemporaneously.

expression. The numbers in the dot plot indicate the percentage of gated cells expressing the relevant marker. (3B) Spleen and lymph node cells isolated from FoxP3 transgenic mice were stained for cell surface expression of CD4, CD25 and CD127. For analysis, the spleen cells were gated on CD4$^+$ lymphocytes (based on forward and side light scatter) and analyzed for CD127 and FoxP3 expression. The numbers in the dot plot indicate the percentage of gated cells expressing the relevant marker.

Figure 4B:
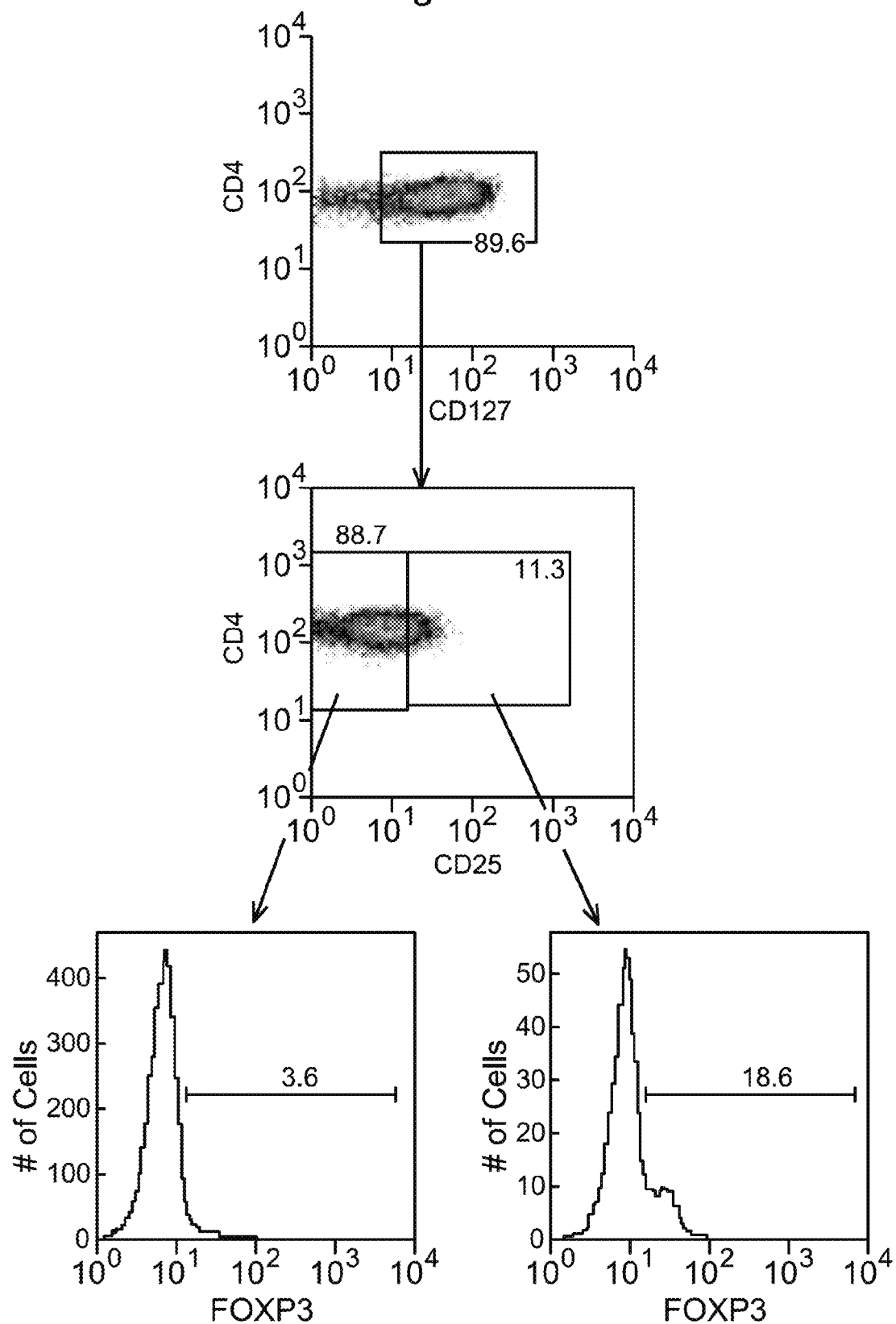

FIGS. 4A-4C. Expression of FoxP3 on different CD4$^+$ T cell subsets. (4A) Human PBMCs were stained for cell surface expression of CD4 and CD127. The stained cells were fixed and stained intracellularly for FoxP3. For analysis, the PBMCs were gated on CD4$^+$ lymphocytes (based on forward and side light scatter and CD4 staining) and analyzed for CD127 and FoxP3 expression. The boxes represent arbitrary designations of CD25+ versus CD25− cells. The numbers in the dot plot indicate the percentage of gated cells expressing the relevant marker. (4B) Human PBMCs were stained for cell surface expression of CD4 and CD127. The stained cells were fixed and stained intracellularly for FoxP3. For analysis, the PBMCs were gated on lymphocytes (based on forward and side light scatter) and analyzed for CD4, CD127 and FoxP3 expression. The boxes represent arbitrary designations of CD127$^+$ versus CD127$^{lo/-}$ cells. The numbers in the dot plot indicate the percentage of gated cells expressing the relevant marker. (4C) Similar staining and analysis was performed on whole blood obtained from 10 healthy individuals. Each symbol represents an individual person, the narrow bar represents the mean percentage of FoxP3$^+$ T cells on either CD4$^+$ T cells gated based on CD25 and/or CD127 expression.

Figure 5A:
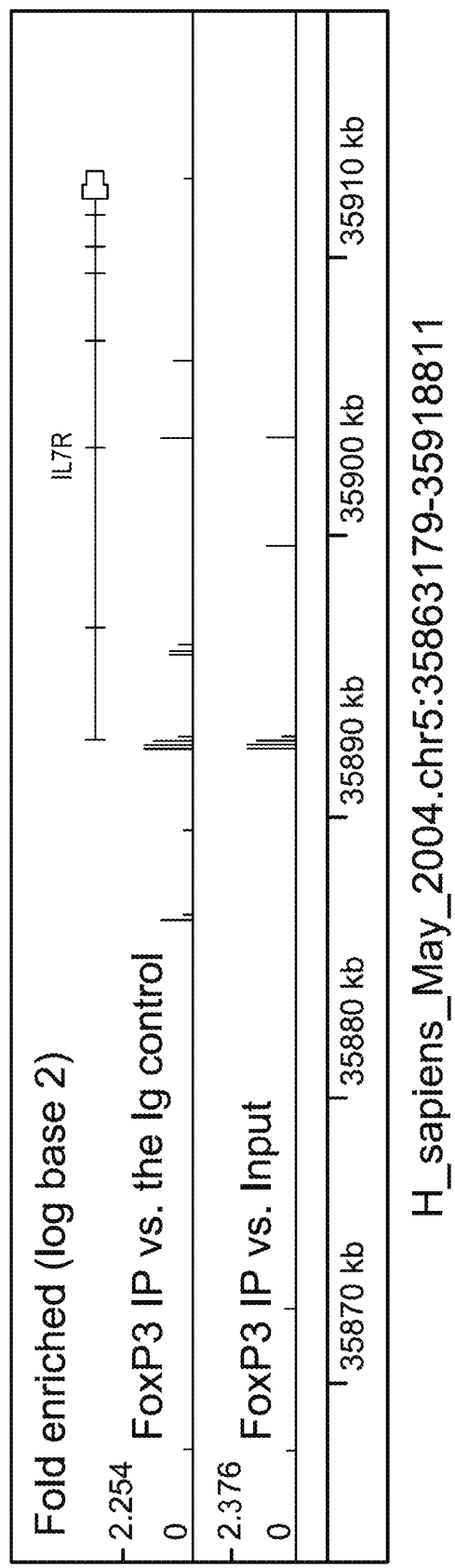
Figure 5B:
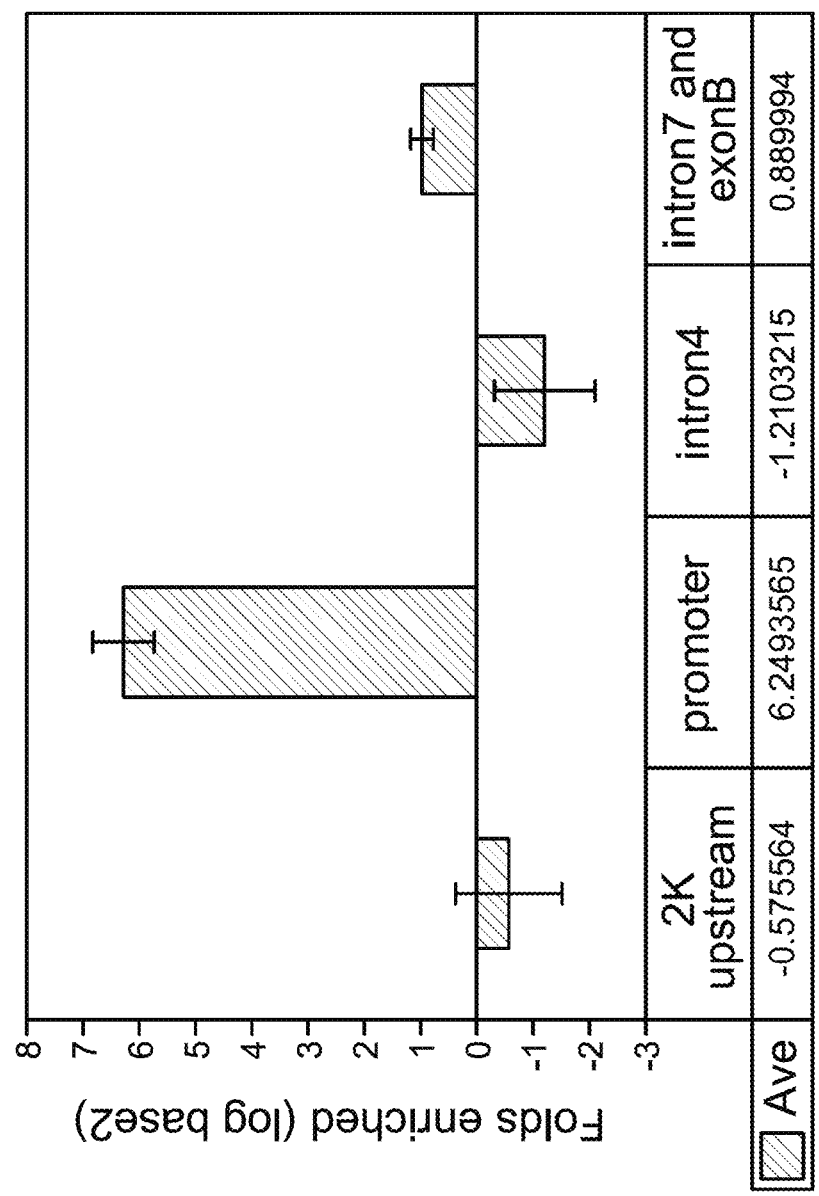

FIGS. 5A-5B. ChIP-CHIP and ChIP-qPCR analysis of FoxP3 bound DNA from CD4$^+$CD25$^{hi}$ human Tregs. Anti-FoxP3 or control rabbit Ig was used to precipitate cross-linked protein-DNA complexes from expanded CD4$^+$CD25$^{hi}$ human Tregs lysate. The cross-linking of the immunoprecipitated material was removed, protease-treated, and the DNA was purified and amplified. The resultant material was hybridized to the whole genome using GeneChip® Human tiling 1.0R array set to identify the locations of binding sites for FoxP3. 2 sets of graphs: FoxP3 IP vs the Ig control and FoxP3 IP vs Input DNA were generated on the hs.NCBIv35 version of the genome essentially following the method described in Cawley et el. (50). (5A) Signal enrichment graphs of IL-7R locus (chr5: 35863179-35918811). Several regions in IL-7R locus are predicted to be positive (chr5:35892564-35892809 promoter) and negative (chr5:35890618-35890846 2K upstream; chr5:35907667-35907852 Intron 4; chr5:35911721-35911888 intron 7 and exon 8). (5B) SYBR green qPCR of IL-7R chromosomal regions. FoxP3 IP vs the IgG fold enrichment ratio was determined from duplicate ChIP assay evaluated in duplicate by real time PCR.

Figure 6:
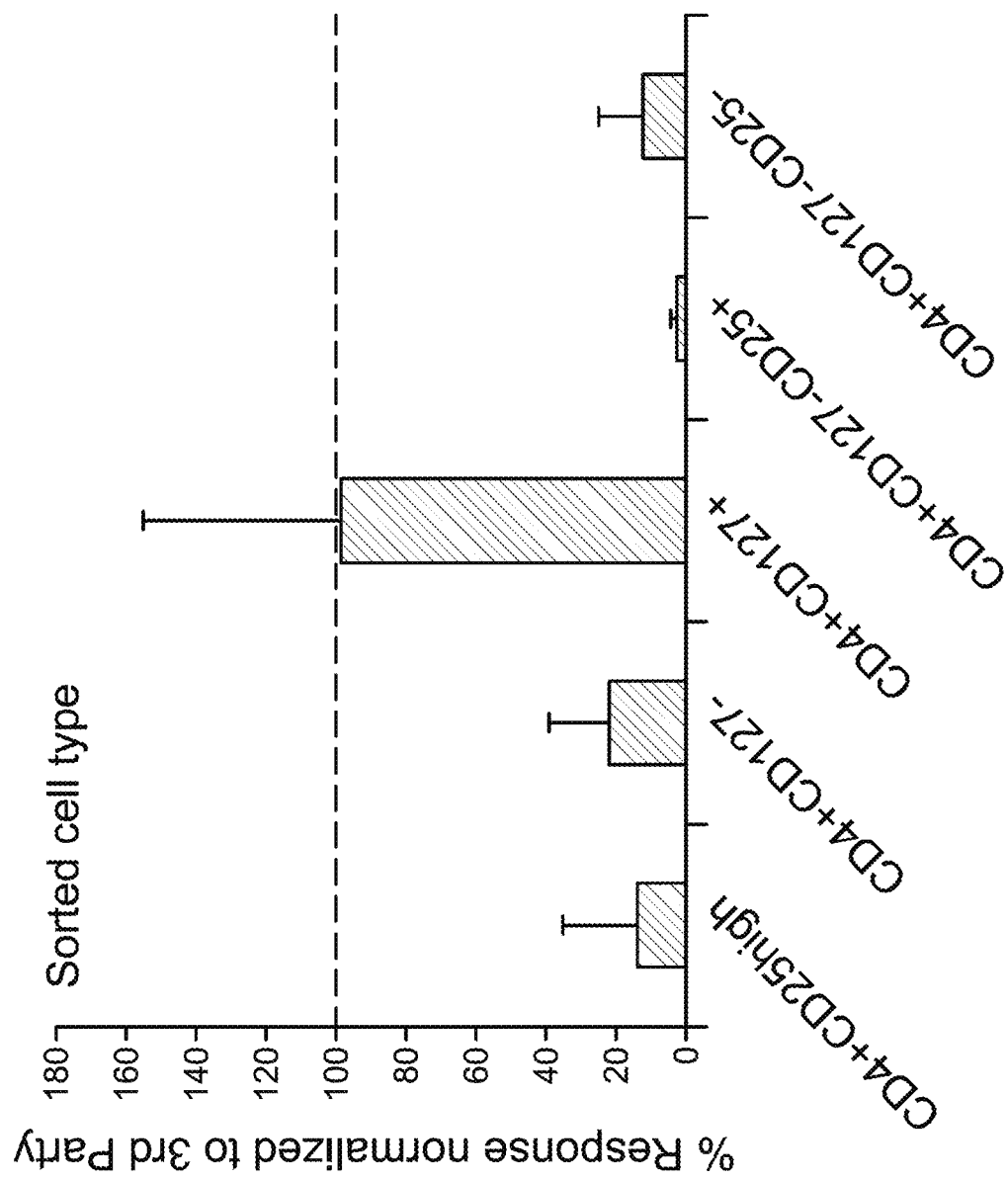

FIG. 6. Proliferative response of isolated T cell subsets. Buffy coat samples were sorted based on CD4, CD127 and CD25 expression. 30,000 sorted cells were put into culture with allogeneic anti-CD3-depleted, irradiated, third party PBMC as stimulators. T cells were incubated for 7 days at 37° C. in 5% $CO_2$. Sixteen hours before the end of the incubation, 1 µCi $^3$H-thymidine was added to each well. Plates were harvested and data analyzed. Data is representative of 9 separate experiments.

Figure 7A:
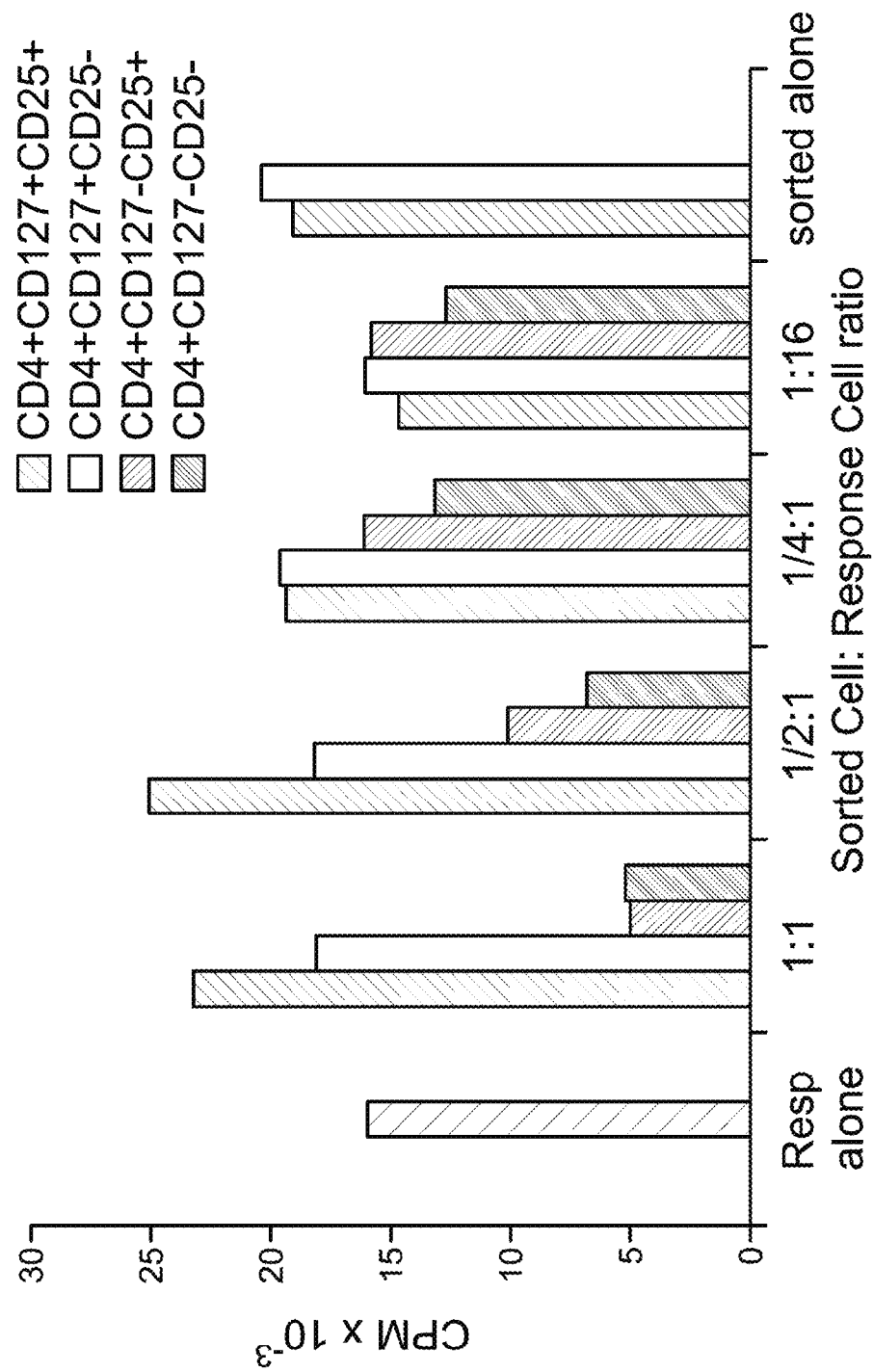
Figure 7B:
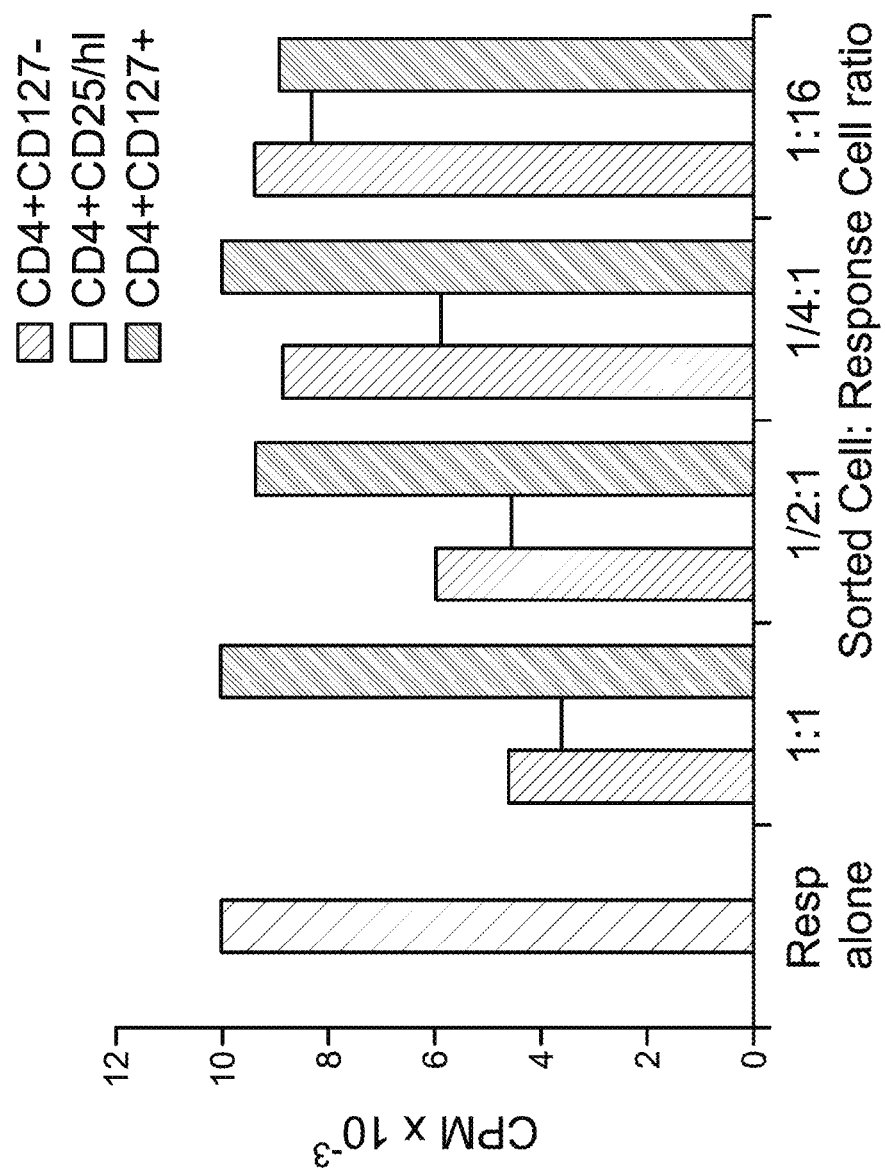

FIGS. 7A-7B. Suppression of allogeneic MLR by individual T cell subsets. Buffy coat samples were sorted based on CD127 and CD25 expression. 30,000 sorted cells were combined with 100,000 autologous PBMC as responders, and 100,000 allogeneic anti-CD3-depleted, irradiated third party PBMC as stimulators. T cells were incubated for 7 days at 37° C. in 5% $CO_2$. Sixteen hours before the end of the incubation, 1 µCi $^3$H-thymidine was added to each well. Plates were harvested and data analyzed. Data is representative of 9 separate experiments sorting 7 different subpopulations of CD4$^+$ cells indicated (7A) CD127$^+$CD25$^+$, CD127$^+$CD25$^-$, CD127$^{lo/-}$CD25$^+$, CD127$^{lo/-}$CD25$^-$ and (7B) CD127$^{lo/-}$, CD25$^{hi}$, CD127$^+$. 100,000 responders are present in each well with decreasing numbers of sorted cells added at 1:1 ratio (30,000:100,000), 1:½ (15,000 sorted cells), 1:¼ (7,500 sorted cells), 1:1/16 (1,875 sorted cells) in comparison to sorted cells alone. Results are represented as counts per minute (CPM).

Figure 8:
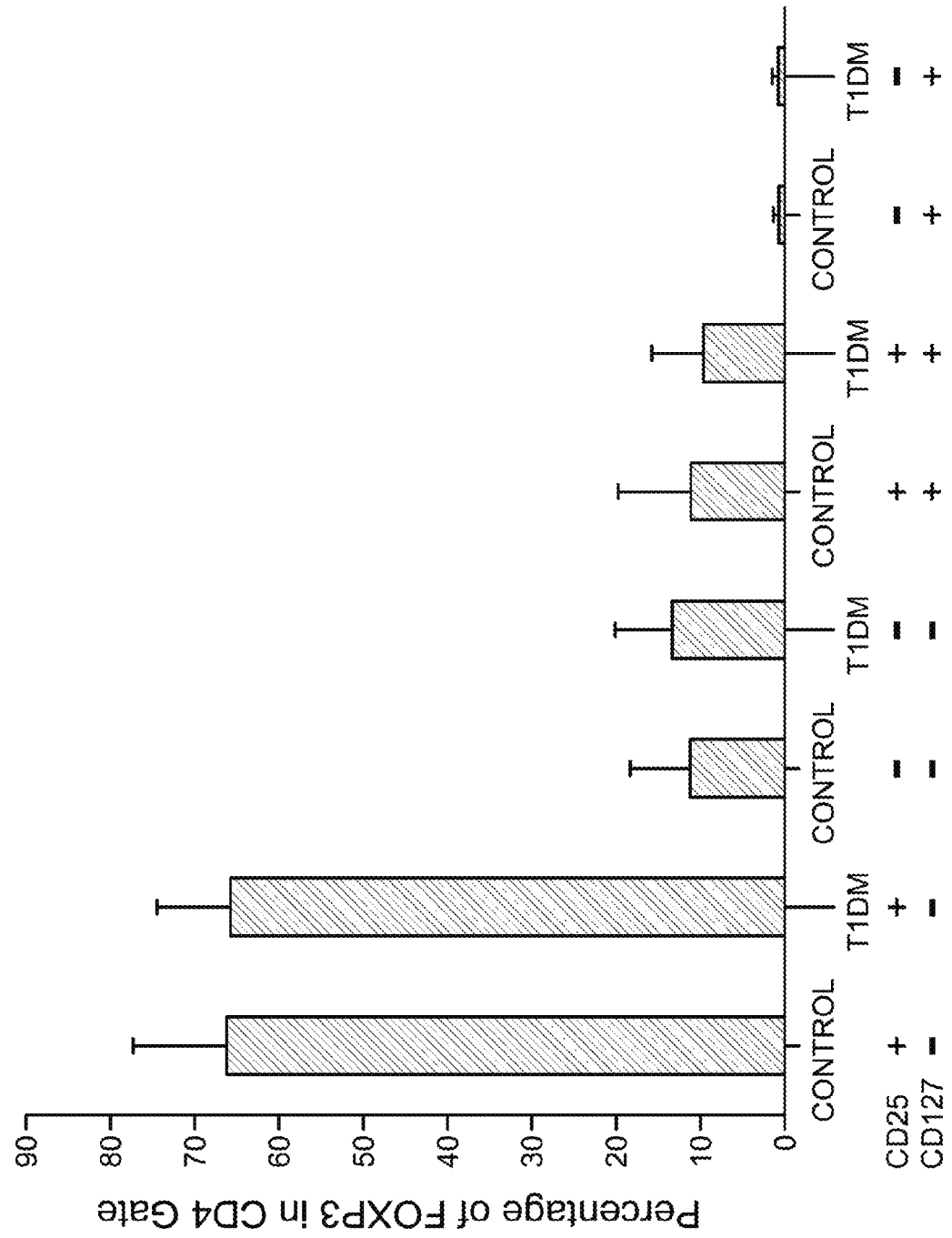

FIG. 8. Frequency of various T cell subsets in patients with Type 1 Diabetes versus healthy control subjects. The data was obtained from total 10 healthy control individuals and 16 patients with Type 1 Diabetes. The mean percentage of various T cell subsets and standard deviation.

FIG. 9 An amino acid sequence of a human CD127 protein (SEQ ID NO:1).

FIG. 10. An amino acid sequence of a human CD4 protein (SEQ ID NO:2).

Figure 11:
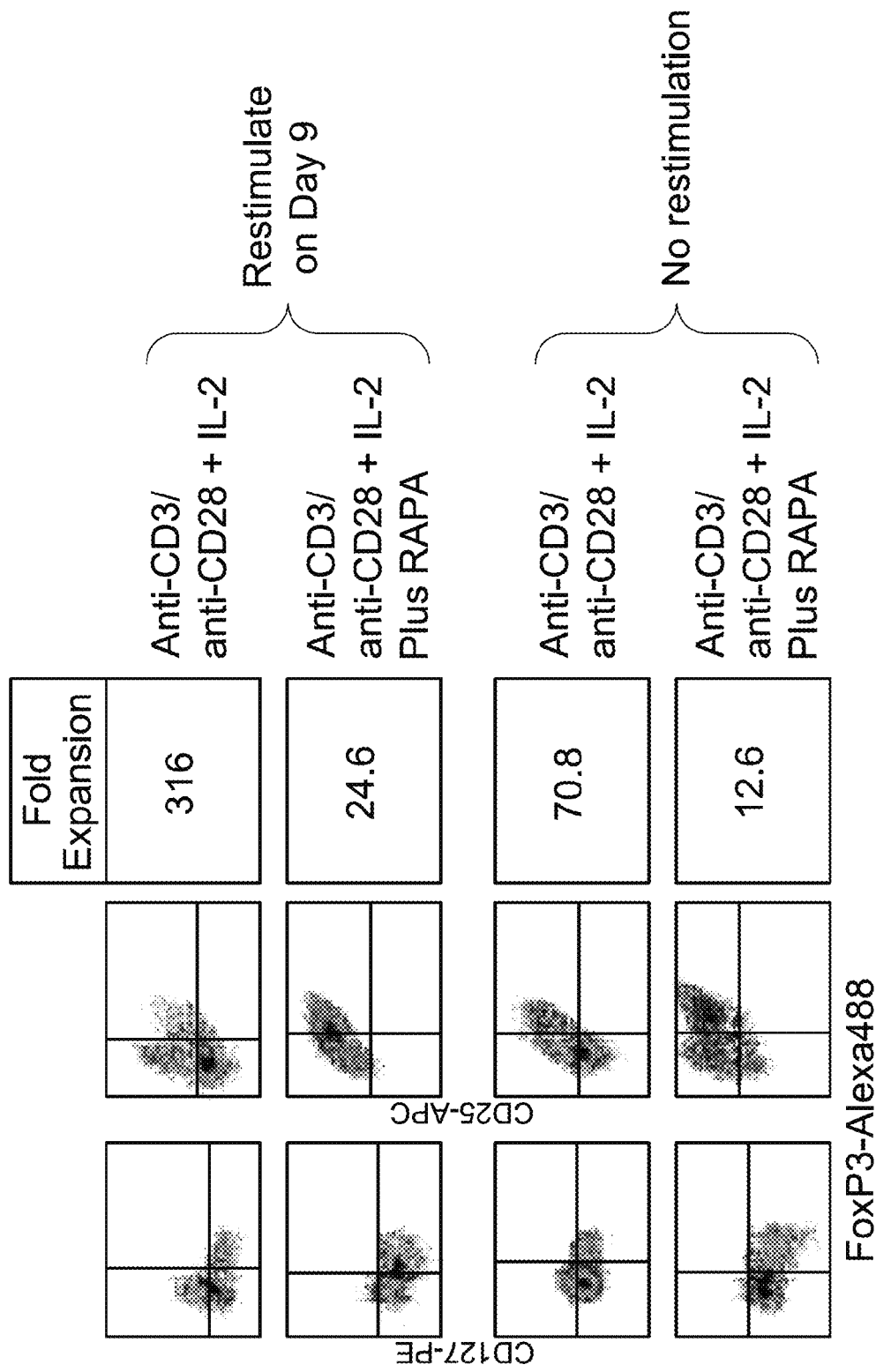

FIG. 11. FoxP3 expression on day 14 of expanded CD4$^+$CD127$^-$ T cells. Separated CD4$^+$CD127$^{lo}$ cells were cultured for 14 days with anti-CD3/anti-CD28 plus IL-2 and plus or minus rapamycin (RAPA). As can be seen the cells expanded best in the absence of rapamycin and when restimulated with the mAb and IL-2 cocktail on day 9. Extent of expansion shown in right hand boxes. The cell expanded with RAPA had the highest levels of FoxP3 and percentage of FoxP3$^+$ cells. The majority of FoxP3 negative cells were CD25$^{lo}$ versus FoxP3$^+$ cells in the same culture.

Figure 12:
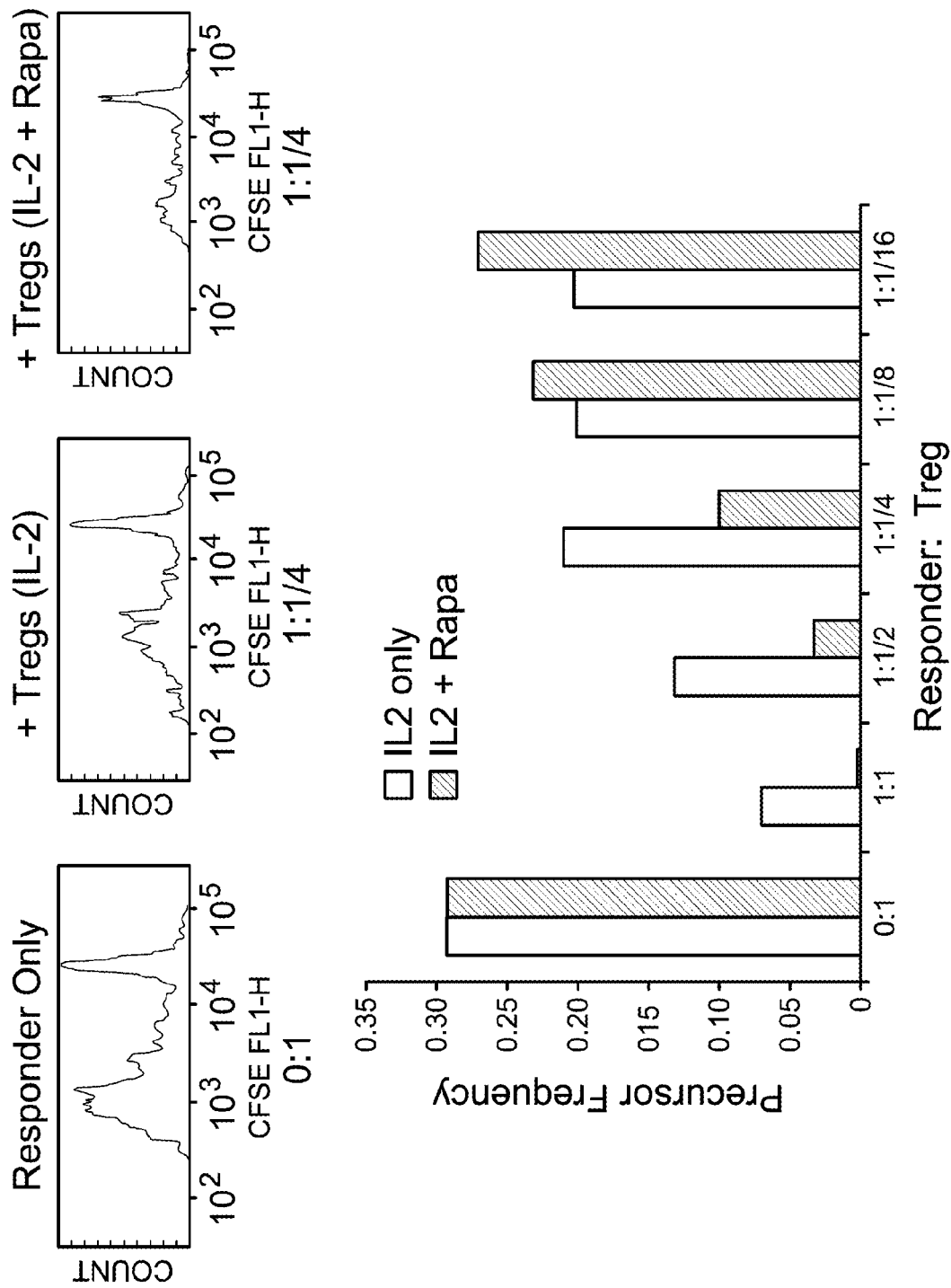

FIG. 12. Expanded CD4$^+$CD127$^{lo/-}$ Tregs suppress and maintain FoxP3, especially when treated with rapamycin. At 14 days, expanded cells were separated and added to a CFSE suppression assay.

Figure 13A:
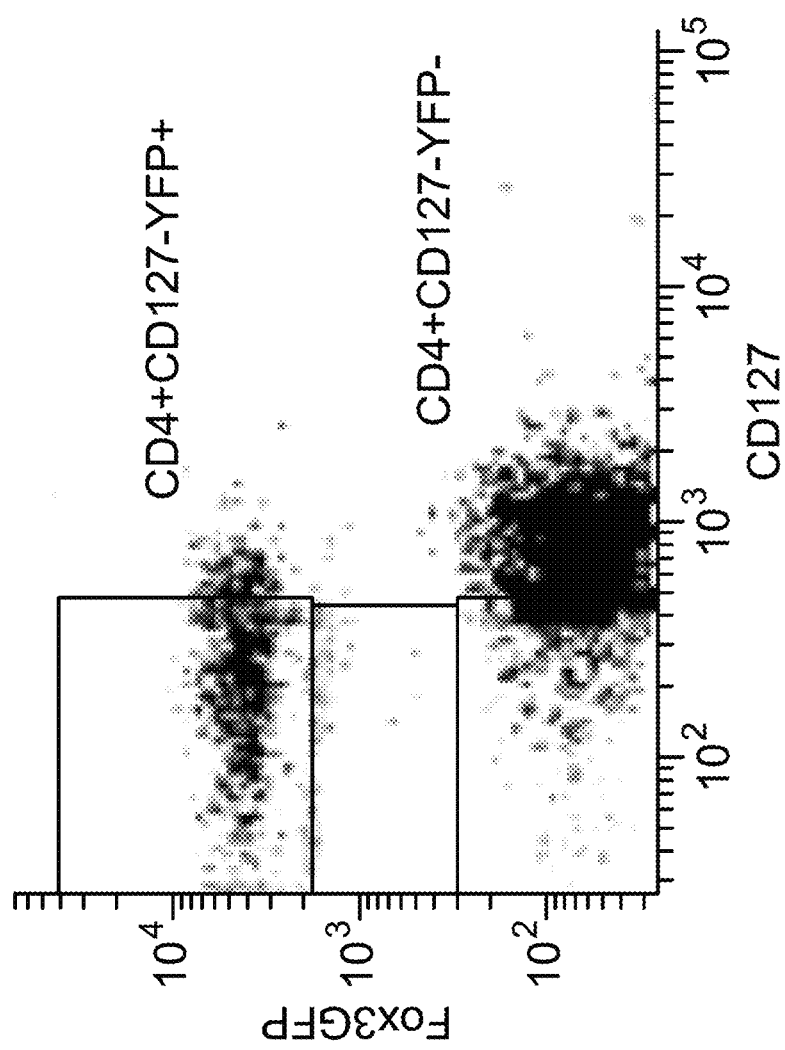
Figure 13B:
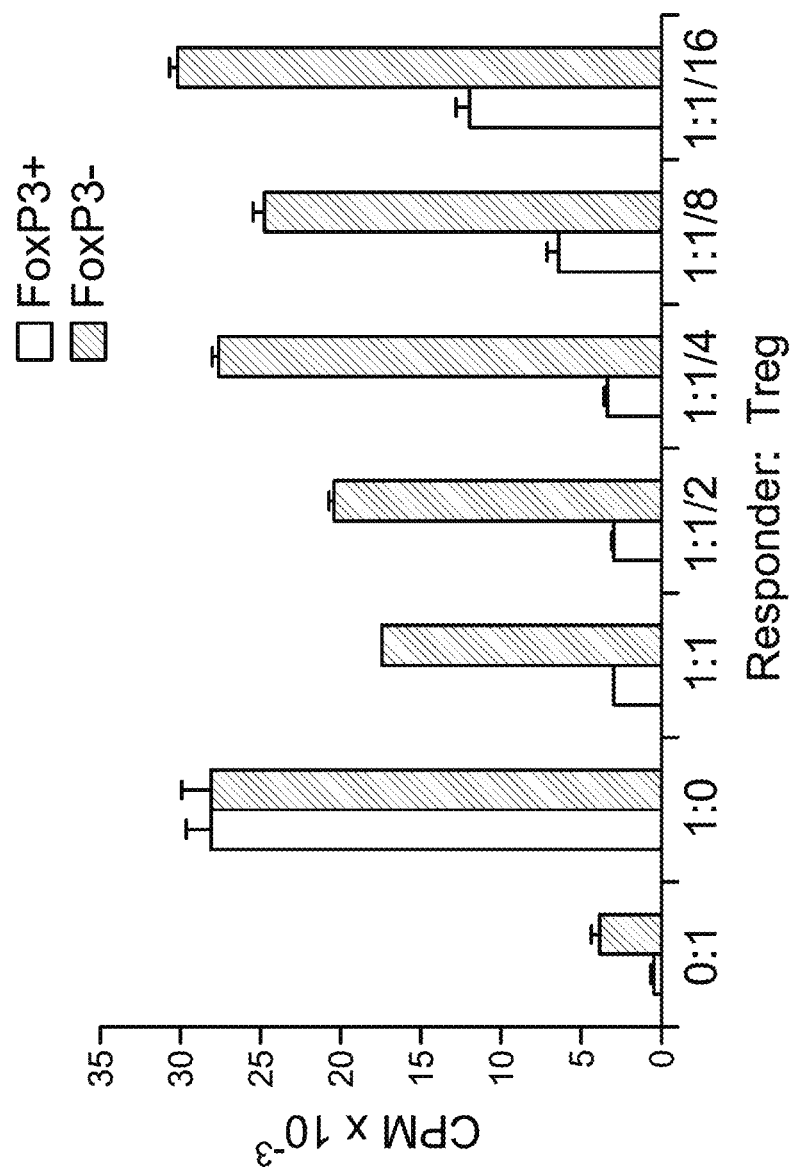

FIGS. 13A-13B. Expanded CD4$^+$CD127$^{lo/-}$ Tregs suppress and maintain FoxP3, especially when treated with rapamycin—Comparison of CD4$^+$CD27$^{lo}$ suppression based on CD25 separation after expansion. At 14 days, expanded cells were separated into CD25$^+$ (middle column) and CD25$^-$ (right column) subsets and added to a CFSE suppression assay. Interestingly, after culture both populations suppressed equivalently suggesting that CD25 expression was not essential to confer suppressive activity on the expanded cells. However, we were unable to rule out whether the cells that suppressed in these cultures were derived from CD25$^+$ cells or had down-regulated CD25 during the culture.

Figure 14B:
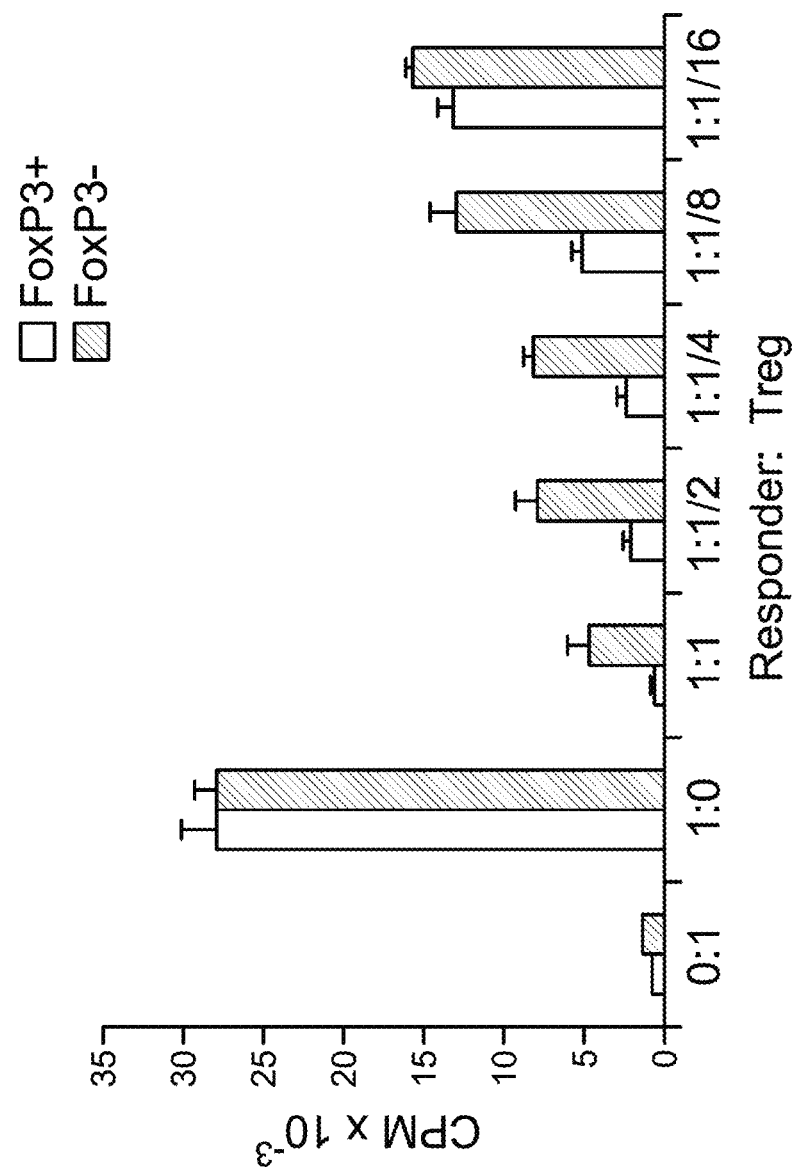

FIGS. 14A-14B. FoxP3 and CD127 expression and Treg function of fresh CD4$^+$CD127$^{lo}$ FoxP3$^+$ and FoxP3$^-$ mouse T cells.

DETAILED DESCRIPTION OF THE INVENTION

Definitions

Unless otherwise stated, the following terms used in the specification and claims have the meanings given below.

It is noted here that as used in this specification and the appended claims, the singular forms "a," "an," and "the" include plural reference unless the context clearly dictates otherwise.

By a "population of cells" is meant a plurality of cells, preferably at least $10^3$, $10^4$, $10^5$, $10^6$, $10^7$, $10^8$, $10^9$, $10^{10}$, or $10^{11}$ cells. The population in some embodiments has from $10^5$ to $10^7$ cells, $10^6$ to $10^8$ cells, or from $10^8$ to $10^{11}$ cells, or $10^{10}$ to $10^{12}$ cells.

A therapeutically effective amount of isolated or expanded isolated $CD127^{Lo/-}$ regulatory T-cells provided by the invention is generally between $10^7$ to $10^{11}$ cells, and more preferably $10^7$ to $10^9$ cells.

Immune conditions, diseases, disorders and reactions or responses to be treated according to the methods and compositions of the invention means a disease in which the immune system contributes to pathogenesis. These reactions include, but are not limited to, autoimmune conditions, disorders or diseases and persistent and progressive immune reactions to infectious non self antigens from bacterial, viral (e.g., HCV), fungal, or parasitic organisms which invade and persist within mammals and humans. Such conditions and disorders include allergies and/or asthma. The allergies and asthma may be due to sensitization with foreign or non-self antigens as pollen, animal dander and food proteins. The source of the provoking foreign antigen can be plant, fungal, mold, or other environmental contaminant.

Autoimmunity and Autoimmune Disorders and Diseases. Autoimmunity is defined as persistent and progressive immune reactions to non infectious self antigens, as distinct from infectious non self antigens from bacterial, viral, fungal, or parasitic organisms which invade and persist within mammals and humans. Autoimmune conditions include scleroderma, Grave's disease, Crohn's disease, Sjorgen's disease, multiple sclerosis, Hashimoto's disease, psoriasis, myasathenia gravis, Autoimmune Polyendocrinopathy syndromes, Type I diabetes mellitus (TIDM), autoimmune gastritis, autoimmune uveoretinitis, polymyositis, colitis, and thyroiditis, as well as in the generalized autoimmune diseases typified by human Lupus. "Autoantigen" or "self-antigen" as used herein refers to an antigen or epitope which is native to the mammal and which is immunogenic in said mammal disease.

A patient with an autoimmune disease may be diagnosed as known to one of ordinary skill in the art. Such patients may be identified symptomatically and/or by obtaining a sample from a patient and isolating autoreactive T cells and comparing the level of autoreactive T cells in a patient to a control (see, U.S. Patent Application Publication No. 20060105336). For instance, type 1 diabetes may be identified by age of on-set and dependence on insulin injections to maintain glucose homeostasis.

The response of a patient with an autoimmune disease to treatment may be monitored by determining the severity of their symptoms or by determining the frequency of autoreactive T cells in a sample from a patient with an autoimmune disease. The severity of symptoms of the autoimmune disease may correlate with the number of autoreactive T cells (see, U.S. Patent Application Publication No. 20060105336). In addition, an increase in the number of autoreactive T cells in the sample may be used as an indication to apply treatments intended to minimize the severity of the symptoms and/or treat the disease before the symptoms appear.

"CD," "cluster of differentiation" or "common determinant" as used herein refers to cell surface molecules recognized by antibodies. Expression of some CDs (e.g., CD4, CD8, CD25, CD127) is specific for cells of a particular lineage or maturational pathway, and the expression of others varies according to the state of activation, position, or differentiation of the same cells. Preferably, in some embodiments, the CD determinants are human when the isolated cells are to be administered to a human or a human immune response is being studied.

As used herein, the term "CD127" refers to the "interleukin-7 receptor," present on a Treg cell surface. The IL-7 receptor alpha chain is described in the literature. See, e.g., Goodwin et al. (1990) Cell 60:941-951; GenBank Accession Nos. NP.sub.--032398 and NP.sub.--002176. IL-7R is also referred to in the literature as CD127. (see FIG. 9). The term CD127 ligand refers to a compound that binds to the IL-7 receptor. (see, U.S. Pat. Nos. 5,194,375 and 5,264,416). $CD127^+$ refers to cells which stain intensely or brightly when treated with a labeled antibody directed toward CD127. $CD127^{Lo/-}$ refers to cells of a type which stains slightly/dully or not at all when contacted with a labeled CD127 antibody. Generally, the cells are distinguished according to their CD127 expression levels based upon a readily discernible differences in staining intensity as is known to one of ordinary skill in the art. In some embodiments, the cut off for designating a cell as a $CD127^{Lo/-}$ cell can be set in terms of the fluorescent intensity distribution observed for all the cells with those cells falling below the 50%, 40%, 30% or 20% of fluorescence intensity being designated as $CD127^{Lo/-}$ cells. A CD127– cell can be designated as one which falls below the tenth bottom percentile with respect to fluorescence intensity. In some embodiments, the frequency distribution of the CD127 staining is obtained for all the cells and the population curve fit to a higher staining and lower staining population, and cells assigned to the population to which they most statistically are likely to belong in view of a statistical analysis of the respective population distributions. In some embodiments, the $CD127^{lo/-}$ cells stain two to three fold less intensely than the $CD127^+$ cells. Particularly preferred methods are also exemplified in the Examples.

As used herein, the term "CD4" refers to a cell-surface glycoprotein typically found on the mature helper T cells and immature thymocytes, as well as on monocytes and macrophages. On T cells, CD4 is the co-receptor for the T cell receptor (TCR) and recruits the tyrosine kinase lck. With its D1-portion, CD4 can attach to the β2-domain of MHC class II molecules. $CD4^+$ refers to cells which stain brightly when contacted with labeled anti-CD4 antibody, and $CD4^-$ refers to cells of a type which stain the least brightly, dull or not at all, when contacted with a fluorescently labeled CD4 antibody. Generally, the cells are distinguished according to their CD4 expression levels based upon a readily discernible differences in staining intensity as the CD4 staining is clearly bimodal. In some embodiments, the frequency distribution of the CD4 staining is obtained for all the cells and the population curve fit to a higher staining and lower staining population, and cells assigned to the population to which they most statistically are likely to belong in view of a statistical analysis of the respective population distributions. In some embodiments, the $CD4^-$ cells stain two to three fold less intensely than the $CD4^+$ cells. Particularly preferred methods are also exemplified in the Examples.

Methods of segregating CD8 T cells into + and – categories are known to persons of ordinary skill in the art. In some embodiments, the frequency distribution of the CD8 staining is obtained for all the cells and the population curve fit to a higher staining and lower staining population, and cells assigned to the population to which they most statistically are likely to belong in view of a statistical analysis of the respective population distributions. In some embodiments, the $CD8^+$ cells stain two to three fold more intensely than the $CD8^-$ cells. Particularly preferred methods are also exemplified in the Examples.

As used herein, the term "CD25" refers to the alpha subunit of interleukin-2 receptor, a single-chain glycoprotein with a molecular weight of 55 kD. Following the activation of T cells with antigen or mitogen in the presence of the monokine interleukin-1, interleukin 2 (IL-2) is rapidly synthesised and secreted. In response to this, a subpopulation of T cells expresses high affinity receptors for IL-2. These cells proliferate, expanding the T cell population which is capable of mediating helper, suppressor and cytotoxic functions. IL-2 receptor is not uniquely found on T cells. $CD25^{hi}$ refers to cells which stain brightly when contacted with labeled anti-CD25 antibody, $CD25^+$ refers to cells which stain less brightly when contacted with labeled anti-CD25 antibody, and $CD25^{lo/-}$ refers to cells which are of a type which stains the least brightly dull or null when contacted with a labeled CD25 antibody. Generally, the cells are distinguished according to their CD25 expression levels based upon differences in staining intensity as is known to one of ordinary skill in the art. In some embodiments, the cut off for designating a cell as a CD25 expression category hi, +, lo, or -- cell can be set in terms of the fluorescent intensity distribution observed for all the cells. Generally, cells in the top 2, 3, 4, or 5% of staining intensity are designated "hi", with those falling in the top half of the population categorized as being "+". Those cells falling below 50%, of fluoresecence intensity are designated as $CD25^{lo}$ cells and below 5% as $CD25^-$ cells. Suitable methods of identifying and categorizing regulatory T-cells with respect to their expression of CD25 are described further in Baecher-Allen (41), which is incorporated by reference with respect to same. Particularly preferred methods are also exemplified in the Examples.

A $CD127^{lo/-}$ cell accordingly is of a type which stains the least brightly, dull or null when contacted with a labeled CD127 antibody. Most preferably, the $CD127^{lo/-}$ cells are FoxP3$^+$ cells. In some embodiments the $CD127^{lo/-}$ cells are $CD127^-$ cells, $CD4^+ CD127^{lo/-}$ cells, $CD25^+CD4^+ CD127^-$ cells, $CD25^-CD4^+ CD127^-$ cells, $CD25^{hi-} CD4^+ CD127^-$ cells, or $CD25^{hi-} CD4^+ CD127^{lo/-}$ cells. The designation of a cell type with respect to its levels of expression of a recited biomarker or CD is meant to describe the cell being referenced by its biomarker expression phenotype and is not necessarily an indicator that expression levels were actually determined for the referenced cell. In preferred embodiments, the CD expression pattern of the $CD127^{lo/-}$ cell was determined only with respect to CD127.

$CD127^{lo/-}$ regulatory T-cell populations for use according to the invention are cell populations which have been negatively selected for the CD127 biomarker. In some embodiments, the cells have been further characterized with respect to other CD determinants, particularly the CD4, CD8 and CD25 determinants (e.g., positively selected for with respect to CD4, CD8 and/or CD25). In other embodiments, the cells have been further characterized according to their expression of common determinants other than CD4 and/or CD25. In preferred embodiments, the cell populations are substantially the selected cell type.

In some embodiments, the immunosuppressive T-cell inhibits the production of IL-2 or the proliferation of T-cells in an assay (e.g., MLR). These and other methods of assaying T cells for immunosuppressive activity are known to persons of ordinary skill in the art.

As used herein, the term "sample" or "biological sample" refers to tissues or body fluids removed from a mammal, preferably human, and which contain regulatory T cells, including, but not limited to, FoxP3$^+$ T cells and/or $CD127^{lo/-}$ regulatory T-cells. In some embodiments, the samples are taken from individuals with an immune response which needs to be suppressed. In some embodiments, the individual has an allergy, Graft vs. Host Disease, an organ transplant, or autoimmune disorder. Samples preferably are blood and blood fractions, including peripheral blood. The biological sample is drawn from the body of a mammal, such as a human, and may be blood, bone marrow cells, or similar tissues or cells from an organ afflicted with the unwanted immune response. Methods for obtaining such samples are well known to workers in the fields of cellular immunology and surgery. They include sampling blood in well known ways, or obtaining biopsies from the bone marrow or other tissue or organ. In preferred embodiments, the sample is a T-cell enriched sample in which the sample cells are substantially T-cells.

Enriched T-cell samples refer to those samples or biological samples that have been enriched for T cells by positive selection of the T cells bearing the CD4 marker and/or positive selection of the CD8 marker by determining the levels of expression of the CD4 and CD8 markers, respectively. Other enriched T-cell samples have been enriched for T-cells by negative selection of (i.e., selecting against) non-T-cells which can be distinguished by their levels of expression of other common determinants exclusive of CD25. Most preferably, the enrichment of the sample for T-cells is not specifically according to their level of expression of CD25. Accordingly, in preferred embodiments, the enriched sample substantially comprises a regulatory T-cell population which comprises at least 2, 4, 6, 8, 10, 12, or 20% $CD25^+$ cells or $CD25^{lo}$ or $CD25^-$ cells.

"Inhibitors," "activators," and "modulators" of expression or of activity are used to refer to inhibiting, activating, or modulating cells, respectively, and are identified using in vitro and in vivo assays for expression or activity. The term "modulator" includes inhibitors and activators. A modulator can be an antibody or a soluble ligand which binds a protein of interest. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Preferred modulators according to the invention, inhibit or suppress immune responses to an antigen or alloantigen. Assays to identify inhibitors and activators include, e.g., applying putative modulators to immune cells and then determining the functional effects of the cell on the immune response (e.g., MLR). Inhibitors or modulators are compared to control samples without the inhibitor or modulator to examine the extent of effect. Control samples (untreated with modulators) are assigned a relative activity value of 100%. Inhibition is achieved when the activity value of a polypeptide or polynucleotide of the invention relative to the control sample is about 80%, optionally 50% or 25 to 1%, or less. Activation is achieved when the activity value of a polypeptide or polynucleotide of the invention relative to the control sample is 110%, optionally 150%, optionally 200-500%, or 1000-3000%, or higher.

The term "isolated" with regard to a population of cells as used herein refers to a cell population which either has no naturally-occurring counterpart or has been separated or purified from other components, including other cell types, which naturally accompany it, e.g., in normal or diseased tissues such as lung, kidney, or placenta, tumor tissue such as colon cancer tissue, or body fluids such as blood, serum, or urine. Typically, an isolated cell population is at least two-fold, four-fold, or eight-fold enriched for a specified cell type when compared to the natural source from which the population was obtained.

A population or subpopulation of cells which is "substantially" of a specified cell type is one which has a count of the specified cell type which is at least 50%, 75%, 80%, 90%, 95% or, most preferably, 98% or 99% of the total cell count of the population or subpopulation or one which is at least two-fold, four-fold, eight-fold, ten-fold or 20-fold enriched for a specified cell type as compared to a source population of the specified cell type.

An "anti-X antibody" or "X antibody" according to the invention is an antibody which can specifically bind to X. For instance, the anti-CD127 antibody or CD127 antibody is capable of binding CD127. The antibodies for use according to the invention include, but are not limited to, recombinant antibodies, polyclonal antibodies, monoclonal antibodies, chimeric antibodies, human monoclonal antibodies, humanized or primatized monoclonal antibodies, and antibody fragments. A great many lymphocyte biomarker specific antibodies are commercially available. These include anti-CD127, anti-CD4, and anti-CD25 antibodies.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). In some embodiments, a high affinity ligand of a target may be used in place of the antibody.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules.

Preferably a "label" or a "detectable moiety" is covalently or noncovalently attached to the antibody. A label may be detectable by spectroscopic, photochemical, biochemical, immunochemical, chemical, or other physical means. Particularly useful labels are fluorescent dyes. Methods of attaching labels to antibodies are well known to those of ordinary skill in the art. Particularly preferred labels are those which are attached to the antibody by a linker which can be readily cleaved or separated or subject to hydrolysis by contact with a predetermined enzyme under physiological conditions. The antibody may also be conjugated with a magnetic particle, such as a paramagnetic microbead (Miltenyi Biotec, Germany). An activated T cell bound by a magnetically labeled antibody may be isolated using techniques including, but not limited to, magnetic cell sorting. Suitably labeled antibodies to CD127, CD4 and CD25, as well as many other CDs, are commercially available and known to one of ordinary skill in the art. The antibody may be labeled before or after contact with the sample or before or after contact with the CD. The CD antibody may be labeled by contacting with an a labeled antibody which binds to the CD-antibody.

The term "test compound" or "candidate molecule" or "modulator" or grammatical equivalents as used herein describes any molecule, either naturally occurring or synthetic, e.g., protein, polypeptide, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful immunosuppressive properties are generated by identifying a test compound (called a "lead compound") with some desirable property or activity, e.g., inhibiting expression of CD127, upregulating expression of FoxP3, and creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

"Determining the functional effect" refers to assaying for a compound that increases or decreases the expression of CD127. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; e.g., via chemiluminescence, fluorescence, colorimetric reactions, antibody binding, inducible markers, and ligand binding assays.

Samples or assays for identifying immunosuppressive agents or drugs are conducted in the presence of the candidate inhibitor of CD127 expression and then the results are compared to control samples without the inhibitor to examine for the desired activity or to determine the functional effect of the candidate inhibitor. A positive reference control which is an agent having the desired activity may be used. Control samples (untreated with inhibitors) are assigned a relative of 100%. Inhibition is achieved when the activity value relative to the control is about 80%, preferably 50%, more preferably 25 to 1%, or even less (e.g., 0.2%, 0%).

Discoveries and Findings

We have discovered that CD127, even in the absence of CD25 selection, is an excellent marker of Tregs in human peripheral blood. The cell surface marker is expressed at low levels on an overwhelming majority of Tregs and distinguishes up to 20% of $CD4^+$ T cells as potential Tregs. Moreover, the cell surface marker can be used, without determining the expression of levels of CD25 on the regulatory T-cells, to separate a suppressive T cell subset and will thus be a useful tool for the selection and expansion of T cell for diagnostics and therapeutic applications. Reliance upon the CD127 marker expression alone, has the advantage of convenience and can afford a substantially greater yield of FoxP3+ cells when compared to methods relying on, for instance positive selection of both the CD4 and CD25 biomarkers.

As noted earlier, regulatory T cells (Treg) are critical regulators of immune tolerance. Most Treg are defined based on expression of CD4, CD25 and the transcription factor, FoxP3. Recent information has identified the importance of the gene Foxpro3 which is induced by thymus epithelium to cause T cells to develop $CD25^+$ $CD4^+$ regulatory T cells, in animal models of autoimmune diseases. Deficiency of this gene may lead to wide spread autoimmune phenomena and diseases. However, these markers have proven problematic for uniquely defining this specialized T cell subset in humans. We have found that IL-7 receptor (CD127) is down-regulated on a subset of $CD4^+$ regulatory T cells in peripheral blood. We demonstrate that the majority of these cells are $FoxP3^+$, including those that express low levels or no CD25. A combination of CD4, CD25 and CD127 resulted in a highly purified population of Tregs accounting for significantly more cells that previously identified based on other cell surface markers. These cells were highly suppressive in functional suppressor assays. In fact, cells separated based solely on CD4 and CD127 expression were anergic and, although representing at least 3-times the number of cells (including both $CD25^+$ $CD4^+$ and $CD25^-CD4^+$ T cell subsets), were as suppressive as the "classic" $CD4^+CD25^{hi}$ Treg subset. Finally, we show that CD127 can be used to quantitate Treg subsets in individuals with Type 1 diabetes supporting the use of CD127 as a biomarker for human Treg.

In an effort to define new biomarkers of human Tregs, we have combined gene expression microarray, flow cytometry and function assays to identify new cell surface proteins that distinguish human Tregs. We observed that IL-7R (CD127) is downregulated on all human T cells after activation. In contrast to the reported re-expression of CD127 on the majority of effector and memory T cells (32-35), $FoxP3^+$ T cells remain $CD127^{lo/-}$. In fact, the $CD127^{lo/-}$, $FoxP3^+$ T cells accounted for a significant percentage of $CD4^+$ T cells in the peripheral blood. We demonstrate that FoxP3 interacts with the CD127 promoter and given its purported repressor function likely contributes to the reduced expression of CD127 in Tregs. Finally, we show that isolated $CD4^+$ $CD127^{lo/-}$ T cell subset is anergic and suppresses alloantigen responses in vitro. Together, these data suggest a dichotomy between memory T cells which are IL-$2R^{lo}$IL-$7R^{hi}$ and regulatory $FoxP3^+$ T cells which in most instances up-regulate IL-2R while remaining IL-$7R^{lo/-}$ (30). Thus, the CD127 biomarker can be used to selectively enrich human Tregs for in vitro functional studies and in vivo therapy.

EMBODIMENTS

Accordingly, in a first aspect, the invention provides methods of identifying whether a regulatory T-cell is a suppressive regulatory T-cell by detecting only one cell surface antigen of the T-cell, CD127 in an enriched T cell sample. In some embodiments, the invention provides methods of determining whether a regulatory T-cell is highly likely to be a $FoxP3^+$ suppressive T regulatory cell by detecting only one cell surface antigen of the T-cell, CD127 in an enriched T-cell sample. In preferred embodiments, the $CD127^{lo/-}$ cells are identified by contacting regulatory T-cells in the sample with fluorescently-labeled monoclonal antibodies which specifically bind to $CD127^+$ and identifying cells having a reduced level of fluorescent label attached thereto. The $CD127^{lo/-}$ T-cells in large proportion are immunosuppressive or $FoxP3^+$ cells. In further embodiments, the $CD127^{lo/-}$ T-cells are $CD127^-$ T-cells. In further embodiments, the invention provides methods of estimating the number of FoxP3 positive regulatory T-cells in a sample by detecting only one cell surface antigen of the T-cell, CD127. In other embodiments, the invention provides methods of identifying regulatory T-cells by identifying $CD4^+CD127^{lo/-}$ T cells according to their level of expression of the CD4 and CD127 biomarkers in a biological sample. In some embodiments, the invention provides methods of identifying regulatory T-cells in a sample by identifying $CD8^+CD127^{lo/-}$ T cells according to their level of expression of the CD8 and CD127 biomarkers.

In a second aspect, the invention, provides methods of making an isolated population of an immunosuppressive regulatory T-cells which are substantially $FoxP3^+$ by obtaining a biological sample comprising regulatory T-cells including, but not limited to, $CD127^{lo/-}$ and $CD127^+$ cells and determining the level of expression of CD127, on the surface of the T-cells and isolating the immunosuppressive $CD127^{Lo/-}$ or $CD127^-$ T-cells from those T-cells which are $CD127^+$. In some embodiments, the sample is an enriched T-cell sample. In some embodiments, the T-cell populations so made have at least 4, 8, 10, or 20% $CD25^+$ and/or $CD25^-$ regulatory T cells. In some embodiments, the isolated population is obtained by providing an enriched T-cell sample and determining the level of expression of only one common determinant, CD127, on cells in the enriched sample and isolating $CD127^{lo/-}$ cells from the enriched T-cell sample. In some preferred embodiment, the isolated population is substantially $CD8^+CD127^{lo/-}$ T cells and/or $CD4^+CD127^{lo/-}$ T cells which are Fox $3^+$ cells.

In a third aspect, the invention provides methods of making expanded populations of isolated immunosuppressive regulatory T-cell populations which are substantially $FoxP3^+$ by expanding an isolated T-cell population obtained by the above methods. In some embodiments, the isolated FoxP3$^+$ T cell population is expanded by contacting the isolated T-cells of the population with antigen, alloantigen, or anti-CD3/anti-CD28 antibodies in the presence of TGF-beta or rapamycin. Alternatively, in this aspect, the T-cells in the biological sample can first be expanded and then isolated by the above methods. In preferred embodiments of either approach, the expanded isolated immunosuppressive T-cell populations comprise at least 2, 4, 8, 10, or 20% CD25$^-$ and or CD25$^+$ T regulatory cells. In preferred embodiments, the CD127$^{lo/-}$ cells are identified by contacting regulatory T-cells in the sample with fluorescently-labeled monoclonal antibodies which specifically bind to CD127$^+$ and sorting the regulatory T-cells according to their level of expression of CD127 using a fluorescently activated cell sorter (FACS). In some preferred embodiment, the isolated expanded population is substantially CD8$^+$CD127$^{lo/-}$ T cells and/or CD4$^+$ CD127$^{lo/-}$ T cells which are Fox P3$^+$ cells.

In yet another aspect the invention provides methods of modulating an immune response in a subject, wherein the isolated or expanded, isolated immunosuppressive regulatory T-cell populations obtained by the above methods are administered to the subject. The biological sample from which the regulatory T-cells are obtained may be autologous in that the biological sample itself was obtained from the subject to be treated. The subject can be any mammal (e.g., human, primate) in which modulation of an immune reaction is desired. In some embodiments, a human or mammalian subject has immune disorder, disease or condition or an autoimmune disease to be treated. There are numerous, established animal models for using T cell epitopes of autoantigens to induce tolerance, including multiple sclerosis (EAE: experimental autoimmune encephalomyelitis), myasthenia gravis (EMG: experimental myasthenia gravis) and neuritis (EAN: experimental autoimmune neuritis). In another embodiment, the subject is a human afflicted with an autoimmune disease or disorder, such as any of the diseases/disorders listed in Table A.

In still another aspect, the invention provides, pharmaceutical compositions comprising isolated or expanded immunosuppressive FoxP3$^+$ T-cell populations obtained according to the above methods.

In another aspect, the invention provides methods for producing an antigen-specific regulatory T cell enriched composition, and resultant compositions and methods of use. In one embodiment, the invention provides a method of modulating an immune reaction in a subject, said method comprising (a) obtaining a population of subject-compatible cells including CD4$^+$ and CD4$^-$ cells and CD127$^+$ and CD127$^-$ cells and CD25$^+$ and CD25$^-$ cells; (b) producing an antigen-specific regulatory CD127$^{lo/-}$ or FoxP3$^+$ T cell enriched composition from said population of cells by sorting the cells solely on the basis of the CD127 antigen, and (c) introducing said composition into said subject to modulate said immune reaction in said subject. In some preferred embodiments, the immune response is an autoimmune response and the antigen is an autoantigen. In other embodiments, the immune response is a graft vs. host immune response and the antigen is an autoantigen. In other embodiments, the immune response is allergy, asthma, tissue or organ transplant rejection, or a graft vs. host immune response and the antigen is a purified or unpurified component of the allergen or transplanted tissue or organ provoking the harmful immune response. In preferred embodiments of any of the above, as the enriched composition was not directly selected for on the basis of the presence or absence of CD25 biomarker on the cells, the enriched composition comprises at least 2%, 4%, 6%, 8%, 10% or 20% of CD25$^-$ cells.

In yet further embodiments of any of the above aspects, the selection is not based solely on the determining of the expression level of the CD127 biomarker, but can include determining the expression levels of secondary T-cell surface antigen biomarkers or common determinants, including the CD4, and CD8 and CD25 biomarkers. In some such further embodiments, there is a proviso that no secondary T-cell surface antigen biomarker used isolating the cells is CD4. In still further other embodiments, there is a proviso that no secondary T-cell surface antigen used in isolating the cells is CD25. In some such further embodiments, there is a proviso that no secondary T-cell surface antigen biomarker is CD4 or CD25. In further embodiments of any of the above aspects, the selection is not based solely on the expression level of the CD127 biomarker, but can include T-cell expression levels of the CD25 biomarker. In some other embodiments of any of the above aspects, the selection is not based solely on the expression level of the CD127 biomarker, but can include T-cell expression levels of the CD4 biomarker. In still some further embodiments of the above, the selection is not based solely on the expression level of the CD127 biomarker, but can include T-cell expression levels of both the CD4 biomarker and CD25 biomarkers. Generally, in these embodiments, the CD4 and CD25 biomarkers are positively selected for and the CD127 biomarker is negatively selected for. To enhance enrichment, positive selection may be combined with selection against cells comprising surface makers specific to non-regulatory T-cell types, such as depletion of CD8, CD11b, CD16, CD19, CD36 and CD56-bearing cells as known to one or of ordinary skill in the art. Accordingly, the selection in any of the above embodiment be practiced on an enriched T-cell sample.

In accordance with these further embodiments, the invention also provides methods for producing an antigen-specific regulatory T cell enriched composition, and resultant compositions and methods of use. In one embodiment, the invention provides a method of modulating an immune reaction in a subject, said method comprising (a) obtaining a population of subject-compatible cells containing CD4$^+$ and CD4$^-$ cells and CD127$^+$ and CD127$^-$ cells and CD25$^+$ and CD25$^-$ cells; (b) producing an antigen-specific regulatory CD4$^+$CD127$^{lo/-}$ T cell enriched composition from said population of cells and (c) introducing said composition into said subject to modulate said immune reaction in said subject. In some preferred embodiments, the immune response is an autoimmune response and the antigen is an autoantigen. In other embodiments, the immune response is a graft vs. host immune response and the antigen is an autoantigen. In other embodiments, the immune response is allergy, asthma, tissue or organ transplant rejection, or a graft vs. host immune response and the antigen is a purified or unpurified component of the allergen transplanted tissue or organ provoking the immune response. In preferred embodiments of any of the above, the enriched composition was not directly selected for on the basis of the presence or absence or expression of CD25 biomarker on the cells. In some embodiments, accordingly, the enriched composition comprises at least 2%, 4%, 6%, 8%, 10% or 20% of CD25$^-$ or CD25$^+$ cells. In some embodiments, the enriched composition was also enriched for CD25$^+$ cells by sorting the cells on the basis of the presence or absence of the CD25 biomarker on the cells.

In still a further aspect, the invention provides kits comprising materials specifically useful in performing the above methods.

In still another aspect, the invention provides methods for identifying immunosuppressive drugs by determining their effect on only one T-cell surface marker, CD127, or on a plurality of markers including CD127 and optionally one or the other or both of CD4 and CD25. Drugs which are immunosuppressive reduce the number of CD127$^{lo/-}$ cells in a sample T-cell population when contacted with a sample of such cells as compared to a suitable control sample contacted with vehicle or a non-immunomodulatory substance.

In some embodiments, the invention further provides, an isolated population of regulatory T cells which are substantially CD4$^+$ and CD127$^{lo/-}$. In other embodiments, the Treg cells were isolated from a sample comprising the CD4$^+$ and CD127$^{lo/-}$ Treg cells and further comprising CD4$^-$ cells and CD127$^+$ Treg cells by sorting the cells in the sample according to their expression of the CD4 biomarker and according to their expression of the CD127 biomarker. In some further embodiments, the isolated population is obtained by contacting a sample containing Treg cells with a labeled antibody specific for the CD4 biomarker and with a labeled antibody specific for the CD127 biomarker to identify Treg cells which are CD4$^+$ and CD127$^{lo/-}$, and isolating the identified cells. In some embodiments, the CD4 antibody and the CD127 antibody are each labeled with a different label. In further such embodiments, the CD4 antibody label and the CD127 antibody label are each a fluorescent label. In some further embodiments of any of the above, the sample is not contacted with an antibody specific for the CD25 biomarker or for the CD4 biomarker, or both. Preferably, the CD4$^+$ and CD127$^{lo/-}$ cells are identified and isolated in a fluorescence activated cell sorter. In some embodiments, of any of the above, the sample is a sample of peripheral blood. Preferably, in some embodiments, at least 2, 4, 8, 10, or 20% of the CD4$^+$ CD127$^{lo/-}$ T-cells, of the population are also CD25$^{lo/-}$ or CD25$^-$. In other embodiments, the isolated population of Treg cells are substantially CD4$^+$ and CD127$^-$.

In some embodiments, the invention further provides, an isolated population of regulatory T cells which are substantially CD8$^+$ and CD127$^{lo/-}$. In other embodiments, the Treg cells were isolated from a sample comprising the CD8$^+$ and CD127$^{lo/-}$ Treg cells and further comprising CD8$^-$ cells and CD127$^+$ Treg cells by sorting the cells in the sample according to their expression of the CD8 biomarker and according to their expression of the CD127 biomarker. In some further embodiments, the isolated population is obtained by contacting a sample containing Treg cells with a labeled antibody specific for the CD8 biomarker and with a labeled antibody specific for the CD127 biomarker to identify Treg cells which are CD8$^+$ and CD127$^{lo/-}$, and isolating the identified cells. In some embodiments, the CD8 antibody and the CD127 antibody are each labeled with a different label. In further such embodiments, the CD8 antibody label and the CD127 antibody label are each a fluorescent label. In some further embodiments of any of the above, the sample is not contacted with an antibody specific for the CD25 biomarker or for the CD8 biomarker, or both. Preferably, the CD8$^+$ and CD127$^{lo/-}$ cells are identified and isolated in a fluorescence activated cell sorter. In some embodiments, of any of the above, the sample is a sample of peripheral blood. Preferably, in some embodiments, at least 2, 4, 8, 10, or 20% of the CD8$^+$ CD127$^{lo/-}$ T-cells, of the population are also CD25$^{+/-}$ or CD25$^-$. In other embodiments, the isolated population of Treg cells are substantially CD8$^+$ and CD127$^-$.

In other embodiments, the invention provides an expanded, isolated population of Treg cells which are substantially CD4$^+$ and CD127$^{lo/-}$ or CD8$^+$ and CD127$^{lo/-}$ wherein said expanded population is obtained by contacting the isolated population as described above with alloantigen or anti-CD3/anti-CD28 antibodies in the presence of IL2 plus TGFbeta or rapamycin.

In other embodiments, the invention provides a pharmacological composition comprising isolated cell populations obtained as described above. In related embodiments, the invention provides for the use of a population of any one of the above claims in the manufacture of a medicament for suppressing the immune response in a subject in need thereof. The subject can have an immune disease or disorder, an autoimmune disease, a graft versus host reaction, an organ transplant, asthma, or allergy. In particular embodiments, the subject has Type I diabetes.

Further in view of the above, the invention provides a method of obtaining a population of anergic Treg cells, said method comprising obtaining a sample containing Treg cells and sorting the cells according to the absence or presence of the CD127 biomarker, the CD4 biomarker and/or the CD8 biomarker, and optionally the CD25 biomarker. In further such methods the anergic Tregs are substantially FoxP3$^+$ cells.

In yet other embodiments within this view, the invention provides a method of obtaining an expanded population of anergic T-cells, said method comprising the step of obtaining a sample containing Treg cells, expanding a CD4$^+$CD127$^{lo/-}$ Treg or CD4$^8$CD127$^{lo/-}$ Treg cell population therein and sorting the cells according to the absence or presence or level of expression of the CD127 and CD4 or CD8 biomarkers wherein the suppressive T-cell subset consists substantially of the expanded population of CD8$^+$CD127$^{lo/-}$ Treg or CD4$^+$ CD127$^{lo/-}$ T-cells. In some further embodiments, the cells of the expanded population are not further sorted with respect to the presence of absence of the CD25 biomarker and the suppressive T-cell subset consists substantially of CD4$^+$ CD127$^{lo/-}$ T-cells, with at least 2% of the CD4$^+$ CD127$^{lo/-}$ T-cells, being CD25$^-$. In other embodiments, if sorted according their level of CD25 expression, CD25$^+$ cells in addition to Cd25$^{hi}$ cells are positively selected for.

In yet other embodiments within this view, the invention provides a method of obtaining an expanded population of anergic T-cells, said method comprising the step of obtaining an enriched T-cell sample and isolating and expanding or expanding and isolating a CD127$^{Lo/-}$ Treg cell population therein. In some further embodiments, the cells of the expanded population are not further sorted with respect to the presence of absence of the CD25 biomarker and the suppressive T-cell subset consists substantially of CD4$^+$ CD127$^{lo/-}$ T-cells, with at least 2% of the CD4$^+$ CD127$^{lo/-}$ T-cells, being CD25$^-$. In other embodiments, if sorted according their level of CD25 expression, CD25$^+$ cells in addition to Cd25$^{hi}$ cells are positively selected for.

In another embodiment with this view, the invention provides a method of obtaining an expanded population of anergic T-cells, said method comprising the step of obtaining a sample containing Treg cells, sorting the cells according to the absence or presence of the CD127 and CD4 or CD8 biomarkers to obtain an isolated population of CD4$^+$ CD127$^{lo/-}$ Treg cells and expanding the isolated population of CD4$^+$CD127$^{lo/-}$ Treg cells to obtain the expanded population of anergic T-cells. In yet other embodiments of such, the cells of the expanded population are not further sorted with respect to the presence of absence of the CD25 biomarker and the suppressive T-cell subset consists substantially of CD4$^+$ CD127$^{lo/-}$ T-cells, with at least 2% of the CD4$^+$ CD127$^{lo/-}$ T-cells, being CD25$^-$.

Methods of Modulating an Immune Reaction Using Expanded Populations of CD127$^{lo/-}$ Tregs.

In another aspect, the invention provides methods for producing an antigen-specific regulatory T cell enriched composition, and resultant compositions and methods of use. In one embodiment, the invention provides a method of modulating an immune reaction in a subject, said method comprising (a) obtaining a population of subject-compatible cells containing CD4$^+$ and CD4$^-$ cells and CD127$^+$ and CD127$^-$ cells and CD25$^+$ and CD25$^-$ cells; (b) producing an antigen-specific regulatory CD127$^{lo/-}$ T and/or FoxP3$^+$ cell enriched composition from said population of cells by use of methods described above and (c) introducing said composition into said subject to modulate said immune reaction in said subject. In some preferred embodiments, the immune response is an autoimmune response and the antigen is an autoantigen. In other embodiments, the immune response is a graft vs. host immune response and the antigen is an autoantigen. In other embodiments, the immune response is allergy, asthma, tissue or organ transplant rejection, or a graft vs. host immune response and the antigen is a purified or unpurified component of the allergen transplanted tissue or organ provoking the immune response. In preferred embodiments of any of the above, the enriched composition was not directly selected for on the basis of the presence or absence of CD25 biomarker on the cells. In some embodiments, accordingly, the enriched composition comprises at least 2%, 4%, 6%, 8% of CD25$^-$ cells. In some embodiments, the enriched composition was also enriched for CD25$^+$ cells by sorting the cells on the basis of the presence or absence of the CD25 biomarker on the cells.

In particular embodiments, the population of cells is obtained from said subject, obtained from a donor distinct from said subject, and/or harvested from peripheral blood. The population of cells obtained comprises antigen or autoantigen-specific regulatory T (Treg) cells, and may be derived from any source in which antigen or autoantigen-specific Treg cells exist, such as peripheral blood, the thymus, lymph nodes, spleen, and bone marrow. In certain embodiments, the source of Treg cells may be from cadaveric tissue.

In other embodiments, the producing step comprises expanding said antigen-specific regulatory T cells, and/or enriching the antigen-specific regulatory T cells from said obtained population of cells.

In some embodiments, the expanding is achieved by contacting said population of cells with an antigen-specific regulatory T cell stimulatory composition.

In particular embodiments, the isolated CD127$^{lo/-}$, CD4$^+$ CD127$^{lo/-}$ and/or FoxP3$^+$ T cells are isolated from said population of cells prior to said expanding step, or after said expanding step. In some embodiments, accordingly, the isolated cells comprise at least 2%, 4%, 6%, 8% of CD25$^-$ cells.

In particular embodiments, the stimulatory composition comprises an MHC class II/autoantigenic peptide complex, a co-stimulatory agent or a second regulatory T cell stimulatory agent. In other embodiments, the isolated CD127$^{lo/-}$, CD4+CD127$^{lo/-}$ cells with or without the inclusion of CD25 as an additional positive selection marker are isolated from said population of cells prior to said expanding step, or after said expanding step.

In yet another embodiment, the co-stimulatory agent is an agonist antibody (e.g., an agonist antibody which binds to CD28). In still another embodiment, the second stimulating agent is a cytokine, (e.g, an interleukin, (e.g., interleukin-2)). In some embodiments, the co-stimulatory agent is an agonist antibody (e.g., an agonist antibody which binds to CD28 in the presence or absence of a second stimulating agent which can be a cytokine (e.g., an interleukin, interleukin-2).

In particular embodiments, the stimulatory composition is immobilized on a substrate, such as a cell or bead.

The invention also provides compositions comprising a population of cells wherein the cells are substantially antigen- or auto-antigen specific regulatory CD127$^{lo/-}$, CD4$^+$ CD127$^{lo/-}$ T-cells and/or FoxP3$^+$ T-cells which comprise at least 2, 4, 6, 8, or 10% of CD25$^-$ T cells.

The invention also provides compositions comprising a population of cells wherein the cells are substantially antigen- or auto-antigen specific regulatory CD127$^{lo/-}$, CD8$^+$ CD127$^{lo/-}$ T-cells and/or FoxP3$^+$ T-cells which comprise at least 2, 4, 6, 8, or 10% of CD25$^-$ T cells.

In particular embodiments, autoantigen-specific regulatory T cells are specific for peptides presented in MHC class II molecules including those shown in Table A. In other embodiments, the autoantigen-specific regulatory T cells are effective at modulating an autoimmune reaction when administered to a subject.

TABLE A

| Autoimmune disease | Autoantigen | MHC class II molecule/peptide(s) bound (SEQ ID NO:) |
|---|---|---|
| Lupus erythematosus | giantin | |
| | golgin-245/p230 | |
| | golgin-160/GCP170 | |
| | golgin-95/GM130 | |
| | golgin-97 | |
| | golgin-67 | |
| | transferrin | 119-VVKKGTDFQLNQLEGKK (3) |
| | | 119-VVKKGTDFQLNQLGKK (4) |
| | | [see Freed et al., J. Immunol. (2000) 164: 4697-4705 |
| | $A_\beta^k$ (37-51 major; (37-52 minor) | YVRFDSDVGEYRAVTE (5) |
| | Lysozyme c (48-63) | GDQSTDYGIFQINSRY (6) |
| | nucleoporin NUP155 (120–) | RQVRFYSGVIEL (7) |

TABLE A-continued

| Autoimmune disease | Autoantigen | MHC class II molecule/peptide(s) bound (SEQ ID NO:) |
|---|---|---|
| | Saposin D (37—) | LPDPYQKQCDDFVAE (8) |
| | 26S proteasome p112 (224—) | IFLDDPQAVSDVL (9) |
| | 14-3-3 protein β, δ, ζ, θ, or τ (95—) | KTAFDEAIAELD (10) |
| | $A_\beta^k$ (146—) (110—) | STQLIRNGDWTFQVLVMLEM (11) HHNTLVCSVTDFYPAKIKVR (12) |
| | Ig γ 1-chain (141—) | SMVTLGCLVKGYFPEPVTVT (13) |
| Thrombocytopenic purpura | GPIIb/IIIa platelet integrin | HLA-DR (Kuwana et al., J Clin Invest. 1998 Oct 1;102(7); 1393-402) |
| Goodpasture's syndrome | human glomerular basement membrane | |
| Graves disease | thyroglobulin thyroperoxidase sodium-iodide symporter TSH receptor | |
| Type I diabetes mellitus | Insulin, proinsulin | DQ0601/insulin B ss5-15 aa1-15: FVNQHLCGSHLVEAL (14) (see Ettinger and Kwok, J. Immunol. 1998 Mar 1; 160(5):2365-73) HLA-DR3 |
| | glutamic acid decarboxylase (GAD65) | HLA-DR4 (DRB1*0401)/271-285 (PRLIAFTSEHSHFSL) (15), 116-130 (NILLQYVVKSFDRST) (16); HLA-DR4 (DRA1*0101)/356-370 (KYKIWMHVDAAWGGG) (17), 376-390 (KHKWKLNGVERANSV) (18), 481-495 (LYNIIKNREGYEMVF) (19), 511-525 (PSLRVLEDNEERMSR) (20), 546-560 (SYQPLGDKVNFFRMV) (21), 556-570 (FFRMVISNPAATHQD) (22), and 566-580 (ATHQDIDFLIEEIER) (23); HLA-DQ8/206-220 (TYEIAPVFVLLEYVT) (24) (see Peng, Y. Chin Med J 2001; 114(10):229-242) |
| | tyrosine phosphatase IA-2 tyrosine phosphatase 2b IGRP Human protein: Q9UN79 - SOX-13 protein (Type 1 diabetes autoantigen ICA12) (Islet cell antigen 12). ICA69 | |
| Mysasthenia gravis | Gravin muscle nicotinic acetylcholine receptor (AChR) | 121-126 (PAIFKSYCEIIVTHFP) (25), 129-145 (EIIVTHFPFDEQNCSMK) (26) [see J Immunol 159(3):1570-7] p195-212 (DTPYLDITYHFVMQRLPL) (27) [see Scand J Immun. 44(5):512-21] |
| Pemphigus vulgaris | desmoglein 1, desmoglein 3, Human desmocollin 1 (Dscl) | |
| bullous pemphigoid | BP 180 | |
| Autoimmune hepatitis | Formiminotransferase cyclodeaminase | |
| Autoimmine atrophic corpus gastritis | parietal cell H,K-adenosine triphosphatase (ATPase) | |
| Addison's diesease | CYP21 CYP17 CYP11A1 | |
| Rheumatoid arthritis | endoplasmic reticulum molecular chaperone immunoglobulin binding protein (BiP) | |

TABLE A-continued

| Autoimmune disease | Autoantigen | MHC class II molecule/peptide(s) bound (SEQ ID NO:) |
|---|---|---|
| | human cartilage glycoprotein-39 (YKL40) | HLA-DR4 (DRB1*0401)/aa259-271 (PTFGRSFTLASSE) (28) (see Vos et al, Rheumatology (2000) 39:1326-1331) |
| | type II collagen | |
| | glucose-6-phosphate isomerase | |
| Multiple sclerosis | alpha β-Crystallin | DRB1*1501 |
| | myelin oligodendrocyte glycoprotein (MOG) | HLA-DR4(DRB1*0401)/97-108 (TCFFRDHSYQEE) (29) (see Forsthuber et al, J Immunol. 2001 Dec 15; 167(12):7119-25) |
| | Myelin basis protein (MBP) | 111-119 (SLSRFSWGA) (30) and 87-95 (VVHFFKNIV) (31) presented in HLA-A2 and HLA-A24) [see JI, 172(8):5120-7] |
| | X2MBP | |
| Psoriasis | Cytokeratin 17 cutaneous lymphocyte antigen (CLA) | |
| Autoimmune hemolytic anemia | anion channel protein band 3 | 861-874 (CLAVLWVVKSTPAS) (32) [see Blood 15;102(10):3800-6] |
| Uveitis | S-antigen | 341-354 (FLGELTSSEVATEV) (33) [see Int. Immun., 15(8):927-935] |
| | interphotoreceptor retinoid-binding protein (IRBP) | |
| | HLA-B(B27PD) | 125-138 ALNEDLSSQTAADT (34) [see Int. Immun., 15(8):927-935] |

The invention also provides kits for producing a composition of antigen-specific and antigen non-specific regulatory T cells. The kit can include (a) CD127 antibody, (b) an antigen-specific or non-specific T cell receptor stimulatory agent; and (c) a costimulatory agent. In particular embodiments, the stimulatory agent is an MHC class II/autoantigenic peptide complex. In some embodiments, the costimulatory agent is an agonist antibody, such as an antibody which binds to CD28. The kit may further comprise a second regulatory T cell stimulating agent, such as a cytokine, such as an interleukin, such as interleukin-2 or interleukin-15. The stimulatory agent and said costimulatory agent can be immobilized on a substrate, such as a cell or bead in some embodiments. The kit may also contain a CD4 antibody and/or a CD25 antibody. The antibodies preferably are fluorescently or magnetically labeled and monoclonal. The kit preferably will also contain instructions as to how to isolate CD127$^{lo/-}$ cells and how to store or formulate them for in vitro or in vivo use. Such kits may also provide instructions as to how to select for the CD127$^{lo/-}$ cells using a CD127 antibody. In some embodiments, there is a proviso that the kit does not have means for detecting the CD25 marker.

The invention provides methods and compositions for ex vivo expansion of therapeutic regulatory T cells, and resultant compositions and methods of use. The expansion methods generally comprise the steps of: isolating from a mixed population of T cells a subpopulation enriched in CD127$^{lo/-}$ T cells (Treg cells) by sorting the cells according to the presence or absence or expression of biomarkers as set forth above; expanding the Treg cells of the subpopulation by contacting the subpopulation with effective amounts of (i) a TCR/CD3 activator (ii) a TCR costimulator activator and (iii) IL-2, to obtain ex vivo expanded Treg cells, wherein the expanded Treg cells demonstrate immune suppression, wherein the isolating step is typically prefaced by extracting the population from a person or patient, typically suffering or in remission from an autoimmune or other immune (e.g., graft vs. host disease, asthma, allergy, transplant rejection) disease amenable to therapy as described herein. In some embodiments, the isolating from a mixed population of T cells of a subpopulation enriched in CD4$^+$ CD127$^{lo/-}$ T cells (Treg cells) by sorting the cells according to the presence or absence or expression level of the CD127 biomarkers is performed without regard to the presence or absence of CD25 or CD4 on the cells. In other embodiments, the Treg cells are also enriched for CD25$^+$ cells by selection according to the absence or presence of the CD25 biomarker.

In particular embodiments, the subpopulation comprises greater than 90, 95, 98 or 99% CD127$^{lo/-}$ Treg cells; the isolation step comprises both negative and positive immunoselection and cell sorting; preferably the expanding step effects at least a 100-fold expansion of the subpopulation; the TCR/CD3 activator is a multivalent antibody or ligand for TCR/CD3; the TCR costimulator activator is a multivalent antibody or ligand for CD28, GITR, B7-1/2, CD5, ICOS, OX40 or CD40; the effective amount of IL-2 is 200 to 2500 IU IL-2/ml; and/or the Treg cells suppress proliferation of anti-CD3 or alloantigen stimulated CD25$^-$ T cells in vitro, or allergic immunity or autoimmunity, including graft-versus-host disease in vivo.

In more particular embodiments:

an effective amount of the ex vivo expanded Treg cells is introduced into the patient diagnosed with diabetes mellitus and presenting an indication of impaired glucose homoeostasis selected from fasting plasma glucose (FPG), postprandial glucose (PPG), and glucose tolerance (GTT) and the introduction provides a resultant improvement in the impaired glucose homoeostasis, wherein the improvement is preferably selected from an FPG of 110 mg/dL or less, a 2-hour PPG of 140 mg/dL or less, and a GTT of 140 mg/dL or less 2 hours after a 75-g glucose load;

the TCR/CD3 activator is an anti-CD3 antibody, and the TCR costimulator activator is an anti-CD28 antibody, wherein the anti-CD3 and anti-CD28 antibodies are immobilized on paramagnetic beads provided in a Treg cell:bead ratio of between 1:1 and 1:2;

the TCR/CD3 activator and the expanded Treg cells are antigen-specific, preferably wherein the TCR/CD3 activator is an MHC-peptide multimer, wherein the peptide is a diabetes-associated autoantigen peptide and the diabetes-associated autoantigen is selected from glutamic acid decarboxylase (GAD), an islet cell autoantigen (ICA) and insulin, and the TCR costimulator activator is an anti-CD28 antibody.

The invention also provides methods and compositions for adoptive cellular immunotherapy comprising the step of introducing into a patient in need thereof an effective amount of the subject ex vivo expanded $CD4^+CD127^{lo/-}$ or $CD4^+$ $FoxP3^+$ Treg cells or $CD127^{lo/-}$ or $FoxP3^+$ Treg cells. These methods generally comprise the steps of: extracting a mixed population of T cells from a person; isolating from the population a subpopulation enriched in $CD127^{lo/-}$ regulatory T-cells; expanding the regulatory T-cells of the subpopulation by contacting the subpopulation with effective amounts of (i) a TCR/CD3 activator, (ii) a TCR costimulator activator, and (iii) IL-2, to obtain ex vivo expanded regulatory T-cells; introducing into a patient an effective amount of the ex vivo expanded regulatory T-cells; and detecting a resultant suppression of autoimmunity.

In particular embodiments, the person and patient is a patient diagnosed with diabetes mellitus and presenting an indication of impaired glucose homoeostasis selected from fasting plasma glucose (FPG), post-prandial glucose (PPG), and glucose tolerance (GTT); the subpopulation comprises >98% Treg cells; the subpopulation comprises >98% $CD4^+$ $CD127^{lo/-}$ Treg cells; the isolation step comprises negative and positive immuno-selection and cell sorting; the expanding step effects at least a 100-fold expansion of the subpopulation; the TCR/CD3 activator is selected from a multivalent antibody or ligand for TCR/CD3; the TCR costimulator activator is a multivalent antibody or ligand for CD28, GITR, CD5, ICOS, OX40 or CD40L; the effective amount of IL-2 is 200 to 2500 IU IL-2/ml; the Treg cells suppress proliferation of anti-CD3 or alloantigen stimulated CD25.sup.-T cells, and/or the resultant suppression of autoimmunity is detected as a resultant improvement in the impaired glucose homoeostasis.

In more particular embodiments:

the improvement is selected from an FPG of 110 mg/dL or less, a 2-hour PPG of 140 mg/dL or less, and a GTT of 140 mg/dL or less 2 hours after a 75-g glucose load;

the TCR/CD3 activator is an anti-CD3 antibody, and the TCR costimulator activator is an anti-CD28 antibody, wherein the anti-CD3 and anti-CD28 antibodies are immobilized on paramagnetic beads provided in a Treg cell:bead ratio of between 1:1 and 1:2; and/or the TCR/CD3 activator is an MHC-peptide multimer, wherein the peptide is a diabetes-associated autoantigen peptide and the diabetes-associated autoantigen is selected from glutamic acid decarboxylase (GAD), an islet cell autoantigen (ICA) and insulin, and the TCR costimulator activator is an anti-CD28 antibody.

The population of cells may be obtained from the subject into which the isolated or isolated and expanded Treg-enriched composition is subsequently introduced. The subject can be any mammal in which modulation of an auto-immune reaction is desired. Mammals of interest include, but are not limited to: rodents, e.g. mice, rats; livestock, e.g. pigs, horses, cows, etc., pets, e.g. dogs, cats; and primates, e.g. humans. In one embodiment, the subject is an animal model of an autoimmune disease. There are numerous, established animal models for using T cell epitopes of autoantigens to induce tolerance, including multiple sclerosis (EAE: experimental autoimmune encephalomyelitis), myasthenia gravis (EMG: experimental myasthenia gravis) and neuritis (EAN: experimental autoimmune neuritis). In another embodiment, the subject is a human afflicted with an autoimmune disease or disorder, such as any of the diseases/disorders listed in Table A.

In an alternate embodiment, the population of cells is obtained from a donor distinct from the subject. The donor is preferably syngeneic, but can also be allogeneic, or even xenogeneic provided the cells obtained are subject-compatible in that they can be introduced into the subject, optionally in conjunction with an immunosuppressive therapy, without resulting in extensive chronic graft versus host disease (GvHD). Allogeneic donor cells are preferably human-leukocyte-antigen (HLA)-compatible, and are typically administered in conjunction with immunosuppressive therapy. To be rendered subject-compatible, xenogenic cells may be subject to gamma irradiation or PEN1 0 treatment (Fast, L D et al, Transfusion. 2004 February; 44(2):282-5).

The producing step can provide a predetermined antigen- or autoantigen-specific regulatory T cell enriched composition from said population of cells, preferably specific for a predetermined antigen or autoantigen associated with the targeted allergic or autoimmune reaction, preferably predetermined to be associated with the targeted allergic or autoimmune reaction. In particular embodiments, the producing step comprises expanding said antigen-specific regulatory T cells, and/or enriching said autoantigen-specific regulatory T cells from said obtained population of cells.

An antigen or autoantigen-specific regulatory T (Treg) cell enriched composition is one in which the percentage of antigen or autoantigen-specific $CD127^{lo/-}$ Treg cells is higher than the percentage of antigen or autoantigen-specific $CD127^{lo/-}$ Treg cells in the originally obtained population of cells. In particular embodiments, at least 75%, 85%, 90%, 95%, or 98% of said cells of the composition are antigen or autoantigen-specific regulatory T cells. In particular embodiments, the producing step comprises expanding the antigen-specific regulatory $CD127^{lo/-}$ T cells, and/or enriching said autoantigen-specific regulatory $CD127^{lo/-}$ T cells from said obtained population of cells. In some embodiments, the composition is further enriched by positive selection for CD4 and/or CD25 biomarkers.

In particular embodiments, the regulatory $CD127^{lo/-}$ T cells are enriched from said population of cells prior to said expanding step, or after said expanding step. $CD127^{lo/-}$ Treg cells can be enriched by targeting for selection of cell surface markers specific for immune suppressive $CD127^{lo/-}$ Tregs and separating using automated cell sorting such as fluorescence-activated cell sorting (FACS), solid-phase magnetic beads, etc, as is known to one of ordinary skill in the art (see, U.S. Patent Application Publication No. 2005/0186207) which is assigned to the same assignee as the present invention and incorporated by reference in its entirety. To enhance enrichment, positive selection for T-reg cells may be combined with selection against cells comprising surface makers specific to non-Treg cell types, such as depletion of CD8, CD11b, CD16, CD19, CD36 and CD56-bearing cells as known to one or of ordinary skill in the art.

In particular embodiments, the expanding is achieved by contacting the population of cells with an antigen- or autoantigen-specific regulatory $CD127^{lo/-}$ T cell stimulatory composition. The antigen or autoantigen-specific regulatory CD127$^{lo/-}$ T cells are preferably expanded at least 50-fold, and preferably at least 100, 200, 300, 500 and 800-fold. Antigen and autoantigen-specific regulatory CD127$^{lo/-}$ T cell stimulatory compositions promote the survival, growth, and/or expansion of the antigen or autoantigen-specific regulatory CD127$^{lo/-}$ T cells that express T cell receptor(s) that recognize the desired antigen or autoantigen.

Preferred stimulatory compositions stimulate the CD127$^{lo/-}$ T cell by antigen-specifically binding and activating the T cell receptor complex. A variety of antigen-specific TCR-binding reagents may be used, including cross-linked peptide-bound MHC molecules, antibodies, and mimetics. In a preferred embodiment, the compositions comprises an MHC class I/autoantigenic peptide complex, particularly an aggregate of such MHC/peptide complexes. These complexes comprises at least the extracellular peptide binding domain of an MHC class II molecule in which is functionally bound an autoantigenic peptide. The complexes can be in solution or suspension or immobilized on a substrate, such as presented on the surface of a cell, particularly an APC. Numerous applicable methods are known in the art for generating functional MHC class I/peptide complexes, such as may be found in literu In one embodiment, the autoantigenic peptide is a peptide of the naturally occurring autoantigen that is capable of complexing with an MHC class II molecule. Exemplary MHC class II molecules/peptide complexes are listed in Table A. In an alternative embodiment, the autoantigenic peptide is a mimotope peptide capable of complexing with an MHC class II molecule.

In another embodiment the autoantigenic peptide is a mimotope peptide that is capable of complexing with an MHC class II molecule. Mimotope peptides are described in the literature, further below, and in Examples 1. Protocols for using autoantigen peptides to expand Tregs from otherwise conventional T cells include the use of autoantigen-specific MHC-peptide tetramers, peptide-pulsed DCs (Yamazaki, et al, 2003, J Exp Med 198:235-47) or artificial APCs (Maus et al. Nat. Biotechnol. 20:143-8, 2002) to expand Tregs from patients independent of the cell surface phenotype. In addition, a combination of in vitro and in vivo approaches can enhance the effects of the therapy. For example, recent studies have shown that administration of self antigens, altered peptide ligands and even non-specific stimuli such as FcR non-binding anti-CD3 mAbs can promote antigen-specific Treg activity (Apostolou et al. J. Exp. Med. 199:1401-8, 2003; Belghith et al. Nat. Med. 9:1202-8, 2003). Hence, combining in vivo immunization to induce the Tregs with ex vivo expansion or visa versa may be advantageous.

The stimulatory composition may further include one or more additional agents, e.g., a costimulatory agent, a second regulatory T cell stimulatory agent, or agents that generally promote the survival and/or growth of T cells.

The costimulatory agent is an antibody or ligand specific for a TCR costimulator, such as CD28 or GITR, as described below. In particular embodiments, the costimulatory agent is an agonist antibody, such as an agonist antibody which binds to CD28.

The stimulatory composition alternatively comprises a second regulatory T cell stimulatory agent. Exemplary stimulatory agents include granulocyte colony stimulating factor, interleukins such as IL-2, IL-6, IL-7, IL-13, and IL-15, and hepatocyte growth factor (HGF). In particular embodiments, the second stimulating agent is a cytokine, such as an interleukin, such as interleukin-2.

In some embodiments, one or more components of the stimulatory composition is immobilized on a substrate, such as a cell or bead. Cells suitable for use as substrates include artificial antigen-presenting cells (aAPCs) (Kim, J V et al, Nat Biotechnol. 2004 April; 22(4):403-10; and Thomas, A K et al, Clin Immunol. 2002 December; 105(3):259-72). Beads can be plastic, glass, or any other suitable material, typically in the 1-20 micron range. Paramagnetic beads are preferred.

Optimal concentrations of each component of the stimulatory compositions, culture conditions and duration can be determined empirically using routine experimentation.

The expanded and/or enriched antigen- or autoantigen-specific regulatory CD127$^{lo/-}$ T cells are introduced into the subject to modulate an immune or autoimmune reaction. For example, the subject may be afflicted with a disease or disorder characterized by having an ongoing or recurring autoimmune reaction, such as the diseases/disorders listed in Table A. In particular embodiments, the said modulating comprises inhibiting. CD127$^{lo/-}$ Tregs may serve as a "Trojan Horse" to deliver suppressive or other biologic factors to sites of inflammation, such as IL-4 (Yamamoto et al. J. Immunol. 166:4973-80, 2001), stem cell growth factors, angiogenesis regulators, genetic deficiencies, etc. For example, overexpression of foxp3 has been shown to transform otherwise pathogenic T cells into Tregs (Jaeckel et al. Diabetes. 2004 Dec. 10; [Epub]), and polyclonally expanded Tregs can be transduced with genes encoding an antigen-specific TCR plus FoxP3 to generate potent antigen-specific Tregs in very high numbers and efficiency (Mekala, et al., Blood. 2004 Nov. 4; [Epub]). Thus, these antigen-specific approaches decrease the requirement for high cell numbers while maximizing Treg specificity and function.

Antigen-specific CD127$^{lo/-}$ Tregs are particularly indicated in infectious diseases in which the pathogenicity of the infections is not a result of the cytopathic effects of the pathogen but rather the tissue damage caused by the immunoinflammatory response to the infectious agent. In diseases, such as hepatitis C or HSV-induced corneal inflammation, CD4$^+$ CD127$^{lo/-}$ Treg therapy provides a unique opportunity to control viral-induced immunoinflammatory disease (Suvas et al. J. Immunol. 172: 4123-4132, 2004). Viruses, such as Coxsackie, are known to cause pancreatitis and have been associated with the development of Type 1 Diabetes. Thus, CD127$^{lo/-}$ Tregs that target expressed viral antigens can be used to suppress local tissue damage caused by the infection and reduce the inflammation that incites autoimmune disease development.

The invention also provides compositions comprising a population of cells wherein at least 50% of said cells of said composition are natural (nontransformed), preferably expanded antigen or autoantigen-specific CD127$^{lo/-}$ Treg cells, wherein the antigen or autoantigen-specificity is preferably predetermined, preferably predetermined to a targeted immune or autoimmune reaction antigen. The compositions are made by the methods described herein. The percentage of the antigen or autoantigen-specific regulatory CD127$^{lo/-}$ Treg cells in the composition can be ascertained using the methodology described in the Examples. Preferably, at least 75%, 85%, 90%, 95%, or 98% of said cells of the composition are antigen or autoantigen-specific regulatory T cells.

In addition, the autoantigen-specific regulatory CD127$^{lo/-}$ T cells, in some embodiments, are specific for an MHC class II molecule/peptide complex listed in Table A.

In some embodiments, the autoantigen-specific regulatory CD127$^{lo/-}$ T cells are effective at modulating an autoimmune reaction when administered to a subject. Effective and optimized dosages and treatment regimes using the expanded and/or enriched autoantigen-specific regulatory cells are informed from vast clinical experience with existing T-cell infusion therapies, and can be further determined empirically.

The subject methods find use in the treatment of a variety of different conditions in which the modulation of an aberrant immune response in the host is desired. By aberrant immune response in a host is meant any immune reaction in a subject characterized as an unwanted immune or autoimmune response (e.g., an autoimmune disease). In general, autoimmune responses occur when the immune system of a subject recognizes self-antigens as foreign, leading to the production of self-reactive effector immune cells. Self reactive effector immune cells include cells from a variety of lineages, including, but not limited to, cytotoxic T cells, helper T cells, and B cells. While the precise mechanisms differ, the presence of autoreactive effector immune cells in a host suffering from an autoimmune disease leads to the destruction of tissues and cells of the host, resulting in pathologic symptoms. Numerous assays for determining the presence of such cells in a host, and therefore the presence of an autoimmune disease, such as an antigen specific autoimmune disease in a host, are known to those of skill in the art and readily employed in the subject methods. Assays of interest include, but are not limited to, those described in: Autoimmunity. 2003 September-November; 36(6-7):361-6; J Pediatr Hematol Oncol. 2003 December; 25 Suppl 1:S57-61; Proteomics. 2003 November; 3(11):2077-84; Autoimmun Rev. 2003 January; 2(1):43-9.

By treatment is meant that at least an amelioration of the symptoms associated with the aberrant immune response in the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A therapeutically effect amount of a composition or cell population is an amount which is sufficient to treat or ameliorate the subject condition.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In preferred embodiments, the hosts will be humans.

In further embodiments, the methods include a step of diagnosing the presence of an autoimmune disease to be treated. By diagnosing is meant that the autoimmune response of a subject is generally classified, e.g, diabetes mellitus, SLE, MS, etc. Further, at least one autoantigen may be identified to which the aberrant immune response is directed.

Also provided are reagents and kits thereof for practicing one or more of the above-described methods. The subject reagents and kits thereof may vary greatly. In certain embodiments, the kits include at least a CD127 antibody, and an antigen specific regulatory T cell stimulatory composition. In other embodiments, the kit includes another regulatory T cell stimulating agent, such as a cytokine, such as an interleukin, such as interleukin-2 or interleukin-15. In certain embodiments, the kits may further include reagents for performing the antigen specific regulatory T cell expansion step, including culture dishes or flasks, culture medium, or any necessary buffers, factors, etc. In yet other embodiments, the kits include the means to harvest the sample containing the regulatory T cells and the reagents necessary to perform regulatory T cell enrichment/purification. The antibody may be labeled or the kit may provide reagents for labeling the antibody. In some embodiments of the above, the kits further comprise a CD4 and/or a CD25 antibody and, optionally, selecting for cells which are $CD127^{lo/-}$, $CD4^+$.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

In some embodiments, the stimulatory agent is an MHC class I/autoantigenic peptide complex. Exemplary MHC class II molecules/peptide complexes are listed in Table A. In other embodiments, the stimulatory agent is an antigen which prompts an unwanted immune response in the subject or patient.

The costimulatory agent can be an antibody or ligand specific for a TCR costimulator, such as CD28 or GITR, as described below. In particular embodiments, the costimulatory agent is an agonist antibody, such as an antibody which binds to CD28. In some embodiments, the stimulatory agent and said costimulatory agent are immobilized on a substrate, such as a cell or bead.

The invention also provides methods and compositions for ex vivo expansion of therapeutic regulatory $CD127^{lo/-}$ T cells, and the use of such expanded Treg cells for adoptive cellular immunotherapy to suppress autoimmunity.

The expansion methods generally comprise first extracting a mixed population of T cells from a person or patient, and isolating from the population a subpopulation enriched in $CD127^{lo/-}$ Treg cells. To maximize efficacy, the subpopulation is enriched to at least 90%, preferably at least 95%, and more preferably at least 98% $CD127^{lo/-}$ Treg cells. Cells are generally enriched by targeting for selection cell surface markers specific for immune suppressive $CD127^{lo/-}$ Tregs and separating using automated cell sorting such as fluorescence-activated cell sorting (FACS), solid-phase magnetic beads, etc. To enhance enrichment, positive selection may be combined with negative selection against cells comprising surface makers specific to non-Treg cell types, such as by depletion of CD8, CD11b, CD16, CD19, CD36 and CD56-bearing cells, and as exemplified below.

The $CD127^{lo/-}$ Treg-enriched subpopulation is then expanded ex vivo by culturing the cells in the presence of effective amounts of a TCR/CD3 activator, a TCR costimulator activator, and IL-2. The TCR/CD3 activator is selected from a multivalent antibody or ligand for TCR/CD3, including antigen non-specific activators such as an anti-CD3 antibody, and antigen-specific activators, such as an MHC-peptide multimer (see, e.g. Yee, et al., Adoptive T cell therapy using antigen-specific CD8+ T cell clones for the treatment of patients with metastatic melanoma: In vivo persistence, migration, and antitumor effect of transferred T cells. Proc Natl Acad Sci USA, Dec. 10, 2002; 99(25): 16168-16173; Butterfield, et al., T-Cell responses to HLA-A*0201 immunodominant peptides derived from a-fetoprotein in patients with hepatocellular cancer, Clin. Cancer Res., Dec. 1, 2003; 9(16): 5902-5908; and Yee, et al., Isolation of high avidity melanoma-reactive CTL from heterogeneous populations using peptide-MHC tetramers, J Immunol, 1999, 162: 2227-223), wherein the peptide is typically an autoimmune disease associated peptide, such as a diabetes-associated autoantigen peptide wherein suitable diabetes-associated autoantigens include glutamic acid decarboxylase (GAD), an islet cell autoantigen (ICA) and insulin, wherein combinations of such peptides may also be used.

The costimulator activator can be a multivalent antibody or ligand specific for a TCR costimulator, preferably CD28 or GITR (Shimizu et al., Stimulation of CD25(+)CD4(+) regulatory T cells through GITR breaks immunological self-tolerance, Nat Immunol. 2002 February; 3(2): 135-42. Epub 2002 Jan. 22; Tone et al., Mouse glucocorticoid-induced tumor necrosis factor receptor ligand is costimulatory for T cells, Proc Natl Acad Sci USA. 2003 Dec. 9; 100(25):15059-64. Epub 2003 Nov. 7), though alternative TCR costimulators such as CD5, ICOS, OX40 and CD40L may also be targeted where suitable expansion is so obtained, as may be determined empirically. To promote activation and expansion, the TCR/CD3 and TCR costimulator activators can be typically immobilized on a 3-dimensional solid surface, such as a host cell (e.g. Thomas et al, December 2002, Clin Immunol 105, 259-72) or bead. In a particular embodiment, the activators may be immobilized on paramagnetic beads provided in a Treg cell:bead ratio of between 2:1 and 1:5, preferably between 1:1 and 1:3. Optimal bead size can be empirically determined, though typically the size falls in the range of 1 to 20 micron diameters.

The IL-2 is typically presented in recombinant form, wherein effective amounts of IL-2 can be typically 200 to 2500 IU IL-2/ml. Maximal expansions are determined empirically and will vary by cell type, incubation conditions, etc. For embodiments, maximal expansions may be about 300, 500 and 800-fold.

The suppressive function of the expanded $CD127^{lo/-}$ Treg cells may be detected in vitro or in vivo. For example, in vitro, the expanded $CD127^{lo/-}$ Treg cells may be shown to suppress proliferation of $CD25^-$ T cells stimulated with anti-CD3 in the presence of Fc-receptor-bearing cells, or $CD25^-$ T cells stimulated with irradiated allogeneic splenocytes. Suitable exemplary in vivo animal model and human clinical immune suppression protocols are described in U.S. Patent Application Publication No. 2005/0186207 which is herein incorporated by reference with respect to same.

In some embodiments, the TCR/CD3 activator and the expanded $CD127^{lo/-}$ Treg cells are autoantigen-specific. For example, in a particular such embodiment, an effective amount of the ex vivo expanded $CD127^{lo/-}$ Treg cells introduced into the patient diagnosed with diabetes mellitus (see, e.g. Mayfield et al., Diagnosis and classification of diabetes mellitus: new criteria, Am Fam Physician. 1998 Oct. 15; 58(6):1355-62, 1369-70) and presenting an indication of impaired glucose homoeostasis, such as fasting plasma glucose (FPG), post-prandial glucose (PPG), and glucose tolerance (GTT) provide a resultant improvement in the impaired glucose homoeostasis, particularly wherein the improvement is selected from an FPG of 110 mg/dL or less, a 2-hour PPG of 140 mg/dL or less, and a GTT of 140 mg/dL or less 2 hours after a 75-g glucose load.

Accordingly, the invention provides methods and compositions for adoptive cellular immunotherapy comprising introducing into a patient in need thereof an effective amount of the subject ex vivo expanded $CD127^{lo/-}$ Treg cells. These applications generally involve reintroducing expanded $CD127^{lo/-}$ Treg cells extracted from the same patient, though the methods are also applicable to adoptive cellular immunotherapy for treatment of graft-versus-host disease associated with transplantation, particularly bone marrow transplantation using $CD127^{lo/-}$ Tregs derived from donor tissue.

Adoptive transfer of $CD127^{lo/-}$ Tregs expanded as disclosed herein can be effective to suppress a wide variety of pathogenic autoimmune responses, including diabetes, GVHD, Lupus, rheumatoid arthritis, psoriasis, multiple sclerosis, degenerative heart disease (e.g. Ziad Mallat, et al. Induction of a Regulatory T Cell Type 1 Response Reduces the Development of Atherosclerosis in Apolipoprotein EBKnockout Mice, Circulation. 2003 Sep. 9; 108(10):1232-7), inflammatory bowel disease (Crohn's disease), etc.

In adoptive cell transfer protocols, a mixed population of T cells is initially extacted from a target donor. Depending on the application, the T cells may be extracted during a period of remission, or during active disease. Typically this is done by withdrawing whole blood and harvesting granulocytes by leukapheresis (leukopheresis). For example, large volume leukapherisis (LVL) has been shown to maximize blood leukocyte yield. Harvests reach $20 \times 0.10^6$ cells/L using a continuous flow apheresis device (Spectra, COBE BCT). Symptoms of hypocalcemia are avoided by a continuous infusion of calcium administrated throughout leukapheresis. Typically 15-45 liters of fluid corresponding to about 4 total blood volumes are harvested during a period of time ranging from about 100 to 300 minutes.

The harvested lymphocytes are separated by flow cytometry or other cell separation techniques based on Treg-specific cell markers such as CD127 and expanded as described herein, and then transfused to a patient, typically the cell donor (except in GVHD where the donor and recipient are different), for adoptive immune suppression. Alternatively, the cells may be frozen for storage and/or transport prior to and/or subsequent to expansion. In some embodiments for antigen non-specific expansions, approximately $10^9$ to $10^{11}$ Tregs are transfused; for antigen-specific expansions, therapeutically effective transfusions typically may use about $10^7$ to $10^9$ Treg cells.

Method of Sorting Cells.

The biomarkers used for positive or negative selection of the regulatory T cells of the present invention may be identified by immunoselection techniques known to those in the art which utilize antibodies including, but not limited to, fluorescence activated cell sorting (FACS), magnetic cell sorting, panning, and chromatography. Immunoselection of two or more markers on activated T cells may be performed in one or more steps, wherein each step positively or negatively selects for one or more markers. When immunoselection of two or more markers is performed in one step using FACS, the two or more different antibodies may be labeled with different fluorophores.

Methods of sorting cells are well known to persons of ordinary skill in the art. Cell sorters generally are capable of separating a complex mixture of cells into fractions of a single cell type. Typically, the cells to be sorted are introduced as a thin jet of carrier liquid emanating from a small nozzle orifice. Shortly after leaving the nozzle, the fluid passes through the waist of one or more tightly focused laser beams. The scattered and fluorescence light from these interactions can be collected and analyzed to determine if there are events (e.g., the presence of a fluorescence signal indicating that a fluorophore-labeled monoclonal antibody is bound to the surface of a cell) that prompt the sorting of the cell by various means. More than one label can be monitored at a time. FACS (fluorescence activated cell sorters) can easily analyze cells at speeds greater than 200,000 events per second. Generally, the physics of the carrier fluid, however, and the statistics of distributing the cells among the droplets limits sort rates to about 50,000 cells per second. This combination of speed and reliable separation allows individual cells to be isolated for other uses.

Magnetic cell sorting may be performed using superparamagnetic microbeads composed of iron oxide and a polysaccharide coat. Preferably the microbeads may be approximately 50 nanometers in diameter, and have a volume about one-millionth that of a typical mammalian cell. The microbeads are preferably small enough to remain in colloidal suspension, which permits rapid, efficient binding to cell surface antigens. The microbeads preferably do not interfere with flow cytometry, are biodegradable, and have negligible effects on cellular functions. The antibody coupling to the microbeads may be direct or indirect, via a second antibody to a ligand such as fluorescein.

Methods of Administration of the Isolated and Isolated, Expanded Cell Populations.

The cells can be administered in a variety of ways. By way of nonlimiting example, the cells may be delivered intravenously, or into a body cavity adjacent to the location of an immune response to be suppressed, such as the intraperitoneal cavity, or injected directly within or adjacent to the site of the immune reaction. Intravenous administration, for example, is advantageous in the treatment of many such conditions.

The medicaments and pharmaceutical compositions may be formulated using conventional pharmaceutically acceptable parenteral vehicles for administration by injection. These vehicles may be nontoxic and therapeutic, and a number of formulations are set forth in Remington's Pharmaceutical Sciences. Nonlimiting examples of excipients are saline, Ringer's solution, saline-dextrose solution, and Hank's balanced salt solution. Pharmaceutical compositions may also contain minor amounts of additives such as substances that maintain isotonicity, physiological pH, and stability.

The medicaments and compositions may be in unit dose format. Generally, the unit dose will contain a therapeutically effective amount of $CD127^{lo/-}$ regulatory T-cells. The amount will generally depend on the age, size, gender of the patient, the condition to be treated and its severity, the condition of the cells, and their original characteristics as obtained from the donor of the sample. Methods of titrating dosages to identify those which are therapeutically effective are known to persons of ordinary skill in the art. Generally, a therapeutically effective amount of the cells can be from $10^7$ to $10^{11}$.

The following examples are included to illustrate the invention and methods used in practicing the invention, and not to limit the invention.

EXAMPLES

Example 1. Antibodies

Human Antibodies:

PE-conjugated anti-CD127, APC-conjugated anti-CD25, PerCP-conjugated anti-CD4 used for staining and in sorting was provided by Becton-Dickenson (BD Pharmingen, San Diego, Calif.). Alexa488-conjugated anti-FoxP3 was purchased from BioLegend (San Diego, Calif.) and intracellular staining was performed according to manufacturer's instructions as modified as follows: $5\times10^5$ cells were stained with cell surface markers for 30 min at 4° C. and fixed for 30 min using 1× Fix/Perm buffer. After 3 washes cells were permeabilized in Perm buffer with DNase I (Sigma-Aldrich, St. Louis, Mo.) for 30 min followed by 3 washes. Then cells were blocked with human IgG and stained with anti-human FoxP3-Alexa488 conjugated (BioLegend, San Diego, Calif. clone 206D). The following anti-mouse antibodies were purchased from the indicated sources: anti-CD4, anti-CD25 and mouse IgGi (isotype control) (BD Pharmingen, San Diego, Calif.); and anti-IL-7R (eBioscience, San Diego, Calif.).

Example 2. Subjects

A total of 16 patients with longstanding type 1 diabetes mellitus were studied. Patients (age range 16-56 years, mean age 34, with a disease duration longer than 5 years) were recruited from the Barbara Davis Center for Childhood Diabetes, Denver, Colo., USA. Diagnosis of type 1 diabetes was made primarily by the presence of biochemical autoantibodies or presentation of hyperglycemia with ketosis in childhood. None of the diabetic subjects had severe nephropathy or neuropathy. As controls, 10 subjects (age range 20-50 years, mean age 29) with no family history of diabetes mellitus were also tested. Blood samples were obtained with informed consent under Institutional Review Board approved protocols at either the University of Colorado Health Sciences Center or UCSF as needed.

Example 3. Sorting of CD4+ T Cell Subsets for Flow Cytometry and Functional Studies Human T cells were isolated from leukopacs (Blood Centers of the Pacific). In some cases, negative selection using RosetteSep human CD3 depletion Cocktail (Stemcell Technologies, Seattle, Wash.) was performed. $100\text{-}120\times10^6$ PBMC cells were washed once, counted and resuspended in sorting buffer (PBS+0.1% BSA+1 mM EDTA) at $100\times10^6$ per ml in a 15 ml conical tube. After addition of 1 μl/l million cells volume PerCP conjugated anti-CD4, 1 μl/1 million cells PE conjugated anti-CD127, and 0.7 μl/million cells APC conjugated anti-CD25 antibodies, the cell suspension was mixed gently and incubated at 4 C for 30 min. Cold FACS sorting buffer was added up to a volume of 15 ml, T cells were pelleted and resuspended at $20\times10^6$ per ml. Labeled T cells were sorted using an Aria high-speed cell sorter. The sort gates for the various T cell subsets were set to include only those events exhibiting the CD4-specific fluorescence that were also within the lowest density region of a scatter plot. This amounted to between 11.4% and 33.9% (mean 20.87%) (n=22) of the total number of events for the $CD4^+$ T cells. Based on the CD4 gate, cells were then further gated based on CD127 and/or CD25 expression ($CD4^+CD127^{+/-}$ CD25+/− and $CD4^+CD127^{+/-}$ alone independent of CD25 as well as $CD25^{hi}$ conventional Tregs). Cells were collected into 100% human AB serum (Cambrex, Walkersville, Md.) and washed once with media (RPMI/5% human serum) until ready to be plated in suppression assay. Sorted Treg were 95-98% CD4$^+$CD25$^{hi}$ with a typical yield of 5-12×10$^5$ T cells per sort whereas CD4$^+$CD127–CD25$^+$ cells had a typical yield of 0.9-1.2×10$^6$ and 98% purity.

Example 4. Isolation of CD4$^+$CD25$^{hi}$ and CD4$^+$ CD25$^{neg}$ Cells for GeneChip Arrays Human CD4$^+$ T cells were isolated by negative selection from leukopacs (Stanford University Blood Center) using RosetteSep Human CD4$^+$ T cell Cocktail (Stemcell Technologies, Seattle, Wash.). 7.5-1.25×10$^8$ CD4$^+$ T cells (>90% purity by FACS) were washed once, counted and resuspended in FACS staining buffer (PBS+0.1% BSA) at 10×10$^6$ per ml in a 50 ml conical tube. After addition of 1/90 volume Cy-5 conjugated anti-CD4 (BD Pharmingen) and 1/100 FITC-conjugated anti-CD25 (DakoCytomation, Chicago, Ill.) antibodies, the cell suspension was mixed gently and incubated on ice for 45 min. Cold FACS staining buffer was added to a volume of 50 ml, T cells were pelleted and resuspended at 20×10$^6$ per ml. Labeled T cells were incubated on ice for 45 min and then submitted to flow sorting on a DakoCytomation MoFlo high-speed cell sorter. The sort gates were set to include only those events exhibiting the highest levels of CD25-specific fluorescence (CD4$^+$CD25$^{hi}$ cells) or lowest levels (CD4$^+$CD25$^{neg}$ cells) that were also within the lowest density region of a scatter plot. This amounted to between 0.8% and 1.4% of the total number of events for the CD4$^+$ T cells for each subset.

Example 5. RNA Isolation

Total RNA was isolated from Treg using the total RNA isolation protocol from the RNA RT-PCR Miniprep kit (Stratagene, La Jolla, Calif.) with the following modifications: 100,000 cells were lysed in 150 μl of lysis buffer. To digest DNA, two units of DNAse were added/ug nucleic acid, and Phenol/CHCl$_3$ (Sigma-Aldrich, St. Louis, Mo.) was used to purify total RNA followed by ethanol precipitation. The quantity of total RNA was measured using Nanodrop ND 100 (Nanodrop Technologies, Rockland, Del.). 100 ng of each RNA sample was used for target labeling by a two-round amplification protocol. This protocol was modified from the Affymetrix eukaryotic small sample prep by using 6 pMol of T7 primer and 3 μg/μl of the random primer.

Example 6. GeneChip Arrays and Data Analysis

A total 16 of human HG-U133A GeneChip arrays were used in this study (Affymetrix, Santa Clara, Calif.). Ten ug of fragmented cRNA per GeneChip hybridization were processed on the Affymetrix Fluidic station 450 (Affymetrix, Santa Clara, Calif.) and GeneChip scanner GCS2500 (Hewlett-Packard Company, Palo Alto, Calif.). Gene expression profile was analyzed with MAS5.0 (Microarray Suite version 5.0 (Affymetrix, Santa Clara, Calif.) was used for data acquisition and normalization. Present genes were defined by selecting genes that were present in 3 of 4 arrays. Signal intensities of all present genes for the activated and control groups were combined and analyzed by T-test. Significant genes were selected with p<0.05. The "signal log ratio" (SLR) and "Increase" or "Decrease" call was generated by comparison analysis MAS5.0 and then used for calculating fold changes between groups. We selected 9 out of 16 pair-wise comparisons for particular genes that showed increase or decrease at fold change >2.0. In the second step, signal intensities of present genes were analyzed with Significance Analysis of Microarrays (SAM) was applied for analyzing and determining the gene list based number of significant genes that were identified by T-test and fold change. The final significant genes were combined from the above two steps. Two-dimensional hierarchical clusters are generated using GeneSpring 6.0 software (Silicon Genetics, Redwood City, Calif.).

Example 7. Real-Time PCR Analysis

RNA was isolated using RNeasy mini kits (Qiagen, Valencia, Calif.) according to the manufacturer's instructions. For cDNA synthesis, 500 ng total RNA was transcribed with cDNA transcription reagents using SuperScriptIII reverse transcriptase and oligo(dT)12-18 (InVitrogen, Inc.), according to the manufacturer's instructions. Gene expression was measured in real-time with the GeneAmp 7900 Sequence Detection System (Applied Biosystems) using primers and QuantiTect SYBR Green PCR Kit purchased from Qiagen. The expression level of a gene in a given sample was represented as $2^{-\Delta\Delta Ct}$ where $\Delta\Delta CT=[\Delta CT_{(experimental)}]-[\Delta CT_{(medium)}]$ and $\Delta CT=[CT_{(experimental)}]-[CT_{(housekeeping)}]$. Data is presented normalized to the glyceraldehyde phosphate dehydrogenase (GADP).

Example 8. Suppression Assays

Suppression assays were performed in round bottom 96-well microtiter plates. 100,000 responder PBMC from same cell source as sorted populations, 30,000 sorted cells (one of 7 different sorted subtypes based on CD25 and/or CD127 expression), 100,000 allogeneic irradiated CD3-depleted PBMC were added as indicated. Responder ratio indicated refers to Treg to responder where 1 sorted: 1 responder is 30,000 sorted cells: 100,000 PBMC responder cells. APC consisted of allogeneic PBMC depleted of T cells using StemSep human CD3+ T cell depletion per manufacturer's recommendations (StemCell Technologies, Seattle, Wash.) and irradiated with 40 Gy. Cells were plated in the following order in 50 ul per well: sorted cells, responders, APC. No additional stimulus was added to the wells, however, additional media was added to each well so the final volume was 200 ul per well. Wells surrounding culture wells were filled with PBS in order to prevent evaporation. T cells were incubated for 7 days at 37° C. in 5% CO$_2$. Sixteen hours before the end of the incubation, 1 uCi $^3$H-thymidine was added to each well. Plates were harvested using a Tomtec cell harvester and $^3$H-thymidine incorporation was determined using a 1450 microbeta Wallac Trilux liquid scintillation counter.

Example 9. Antibody Staining and FACS Analysis

Five×10$^4$ T cells per sample were washed once with FACS staining buffer (PBS+0.1% BSA) and resuspended in 100 μL buffer. 1 μL of fluorescence-conjugated specific antibodies (1 μg/million T cells) was added, T cells were lightly vortexed and incubated on ice for 20 min. 500 μL of staining buffer was added to each sample, T cells were pelleted and resuspended in 200 μL buffer and analyzed on a flow cytometer (Becton Dickinson, FACScalibur) Intracellular staining was conducted using the recommended procedure from the BD Pharmingen or eBioscience where indicated.

Example 10. Chromatin Immunoprecipitation—DNA Microarray (ChIP-Chip)

Human CD4$^+$CD25$^{hi}$ Tregs were expanded in vitro as described previously (37). Chromatin fixation and immunoprecipitation were performed using chromatin immunoprecipitation assay kit (Upstate Biotechnology, Inc.) as recommended by the manufacturer. Expanded human Treg were fixed in 1.1% formaldehyde. Protein-DNA cross-linked cell pellets were resuspended in SDS-Lysis Buffer (1 ml per 1×10$^8$ cells) and incubated for 10 minutes on ice. Lysates were sonicated to shear DNA to lengths between 200 and 1000 basepairs and centrifuged for 10 minutes at 13,000 rpm at 4° C. to remove debris. The sonicated cell supernatant was diluted 10-fold in ChIP Dilution Buffer with protease inhibitors (Upstate Biotechnology, Inc) to reduce non-specific background, the diluted cell supernatant was pre-cleared with 40 µl of a Protein A Agarose-50% slurry per 1 ml lysate for 30 minutes at 4° C. with agitation. Cross-linked protein/DNA complexes were immunoprecipitated using control rabbit Ig or affinity-purified rabbit polyclonal anti-human FoxP3 (a generous gift of Roli Khattri and Fred Ramsdell, Celltech, Lt. Seattle, Wash.). The cross-linking of the material was reversed and Proteinase K treated to remove protein from the DNA. The remaining DNA was purified with QIAquick PCR Purification Kit (Qiagen, 28106) and amplified by LMPCR (ligation-mediated PCR) as described previously (49). Array hybridization and analysis were performed at Affymetrix as described previously (50). SYBR Green qPCR was carried out to verify the binding sites predicted by the arrays. Primers for the PCR reactions included: IL-7R promoter: 5'-primer, CAGGGAATATCCAGGAGGAA (SEQ ID NO:35); 3'-primer, TGTGTGAGCCAGTGTGTATGAA (SEQ ID NO:36); IL-7R 2K upstream: 5'-primer, TTTGGGATTTCTCCTTGAACA (SEQ ID NO:37); 3'-primer TCTCTGGGCATTTCAAAACC (SEQ ID NO:38); IL-7R intron 4:5' primer, GAGGTGGCAGAAGAGTGGAG (SEQ ID NO:39); 3'-primer, TGCATCACACTGCAAACAAA (SEQ ID NO:40); IL7-R intron 7 and exon 8:5'-primer, ACATGCTGGCAATTCTGTGA (SEQ ID NO:41); 3'-primer, TCTGGCAGTCCAGGAAACTT (SEQ ID NO:42).

Example 11. Lack of Correlation Between FoxP3 and CD25 in Human CD4$^+$ T Cells Previous studies in mouse using FoxP3-GFP knock-in mice have demonstrated that FoxP3 does not always correlate with CD25 expression (36). Since current efforts in humans have focused on the use of CD25 to isolate and quantify Tregs, we analyzed the expression of FoxP3 in the various CD4$^+$ T cell subsets. Peripheral blood cells from normal subjects were purified on Ficoll gradients and cell surface stained with anti-CD4 and anti-CD25 mAbs. This staining was following by cell membrane permeabilization and intracellular staining with a monoclonal anti-FoxP3 mAb.

Figure 1:
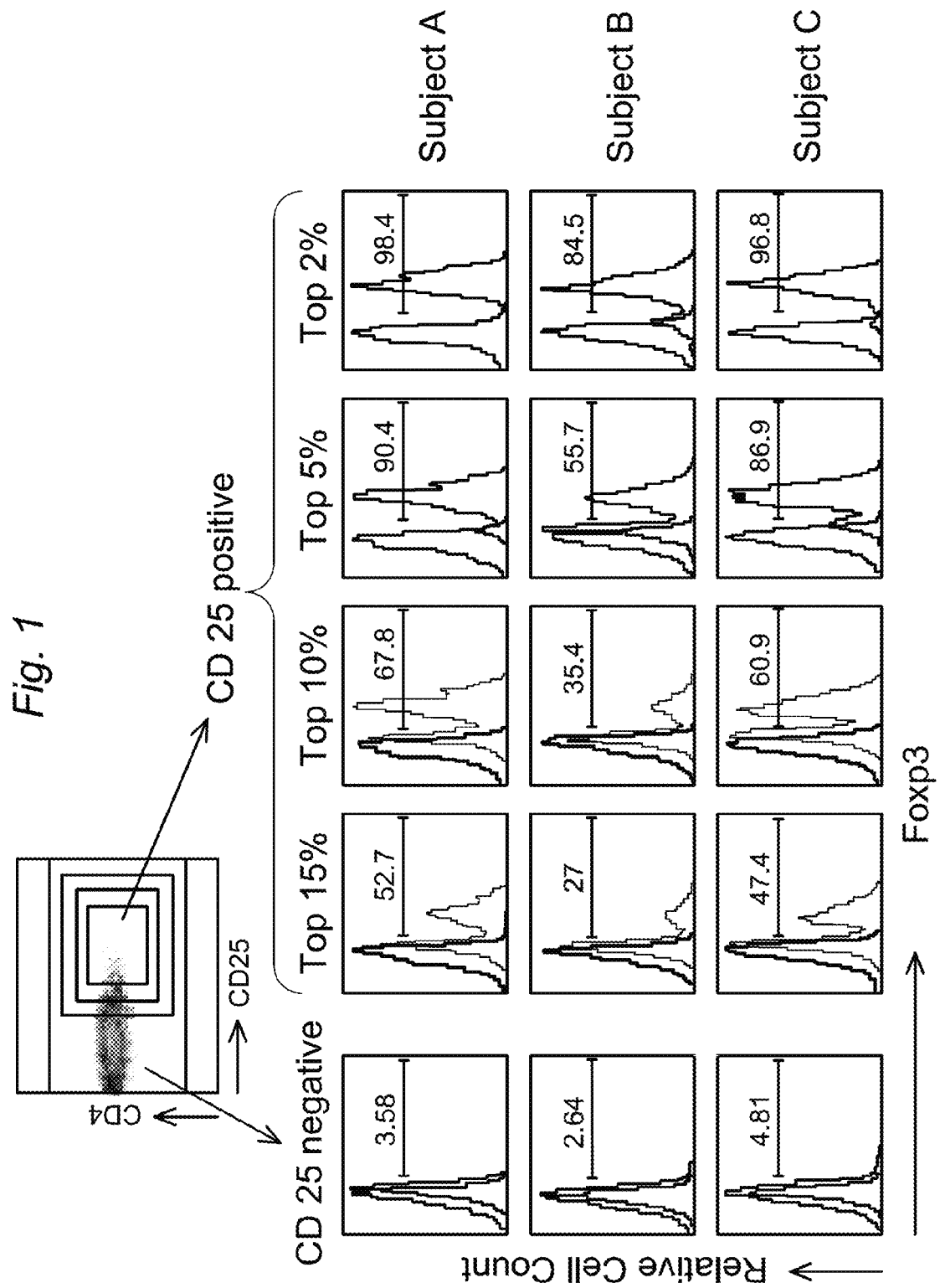
FIG. 1. FoxP3 is expressed on a significant percentage of $CD4^+$ T cells independent of CD25 expression. Human PBMCs were cell surface stained using a combination of anti-CD4 and anti-CD25 mAbs. Once fixed, the cells were stained additionally with anti-FoxP3 mAb. Data are representative of greater than 20 independent individuals and more than 10 experiments. The numbers in the dot plot indicate the percentage of $FoxP3^+$ cells.

As seen in FIG. 1, although the majority of CD4$^+$CD25$^{hi}$ cells (top 2% of gate) were FoxP3$^+$ (ranging from 84.5-96.8% in 3 individuals) there were considerable numbers of FoxP3$^+$ cells that were CD25 dull or even negative. In fact, based solely on CD4 and CD25 gating between 27-52.7% of the cells were FoxP3$^+$ accounting for up to 7.5% of the CD4$^+$ T cells. No significant staining was observed using an isotype control IgG-Alexa 488 while a second anti-FoxP3 mAb from Biolegend gave similar results (data not shown).

An analysis of FoxP3 expression in the CD4$^+$CD25$^-$ T cell subset showed that <5% of the CD25-CD4$^+$ T cells expressed FoxP3, although that percentage was probably an overestimate due to some background staining using the isotype control Ig. However, given the large numbers of cells in this gate, there are likely to be at least some CD4$^+$CD25$^-$ T cells that are FoxP3$^+$. Thus, rather than <2% of the CD4$^+$ T cells falling into a putative Treg subset, as many as 8-10% of the CD4$^+$ T cells may be regulatory in nature.

Example 12. Analysis of Novel Treg-Specific Cell Surface Molecules

To identify additional cell surface markers associated with function and phenotype of Treg, microarray analysis was performed comparing mRNA expressed by CD4$^+$CD25$^{hi}$ T cells with CD4$^+$CD25$^{neg}$ T cells isolated from healthy donor PBMC. mRNA was prepared from 3 blood donors, cRNA prepared and tested on Affymetrix U133A GeneChips. The sorting parameters were based on published studies in which the top 1-2% of CD4$^+$CD25$^+$ T cells were selected as the prototypic Treg subset (16, 37).

Among the genes that differed between the two subsets, IL-7R (CD127) expression was noted to be expressed at 2.4-fold lower levels in CD4$^+$CD25$^{hi}$ T cells as compared to CD4$^+$CD25$^{neg}$ T cells. To confirm the findings, mRNA isolated from 3 independent CD4$^+$CD25$^{hi}$ and CD4$^+$CD25$^{neg}$ T cell preparations were examined by quantitative real time PCR (qPCR). Expression of CD127 mRNA was inversely correlated with CD25 expression. In fact, the level of expression was 3.14 lower in the CD4$^+$CD25$^{hi}$ T cells as compared to CD4$^+$CD25$^-$ T cells (range 2.26- to 4.21-fold).

Figure 2B:
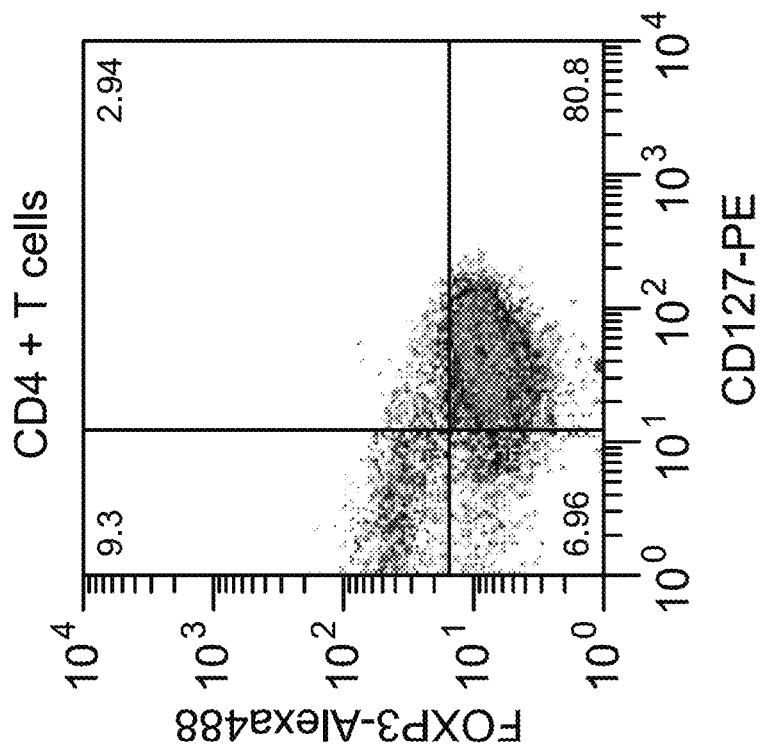
FIGS. 2A-2B. Expression of FoxP3 on different $CD4^+$ $CD127^{+/-}$ human T cell subsets. (2A) PBMCs were harvested from human peripheral blood and stained with CD4, CD25, and CD127 and analyzed on a Becton-Dickenson LSR II. and intracellularly with FoxP3-specific mAbs. Data are representative of greater than 20 independent individuals and more than 10 experiments. (2B) Human PBMCs were stained for cell surface expression of CD4 and CD127. The stained cells were fixed and stained intracellularly for FoxP3. For analysis, the PBMCs were gated on lymphocytes (based on forward and side light scatter) and analyzed for CD127 and FoxP3 expression. The numbers in the dot plot indicate the percentage of gated cells expressing the relevant marker. Data are representative of greater than 20 independent individuals and more than 10 experiments.
Figure 2A:
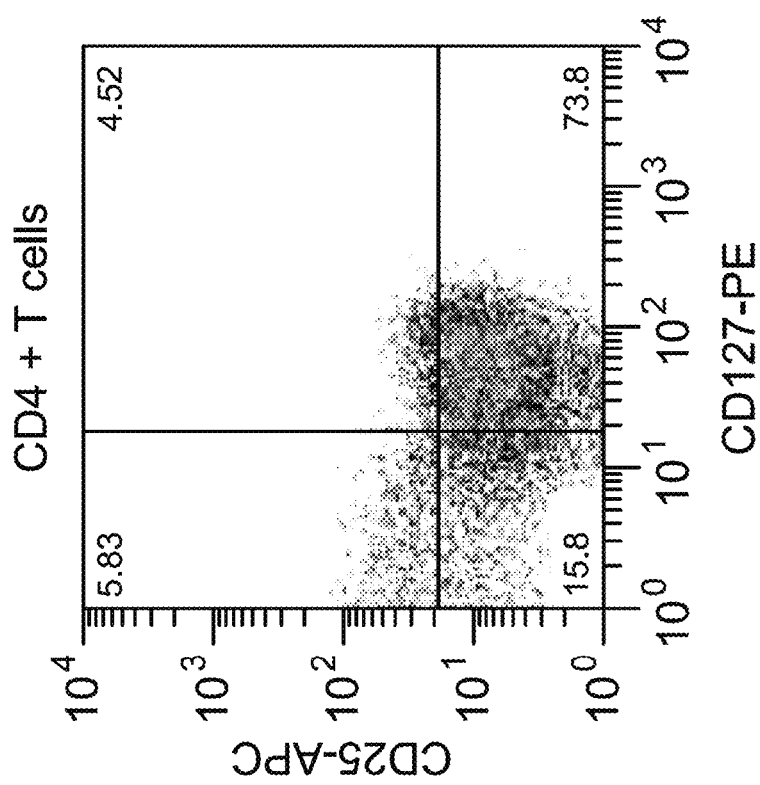
Figure 3A:
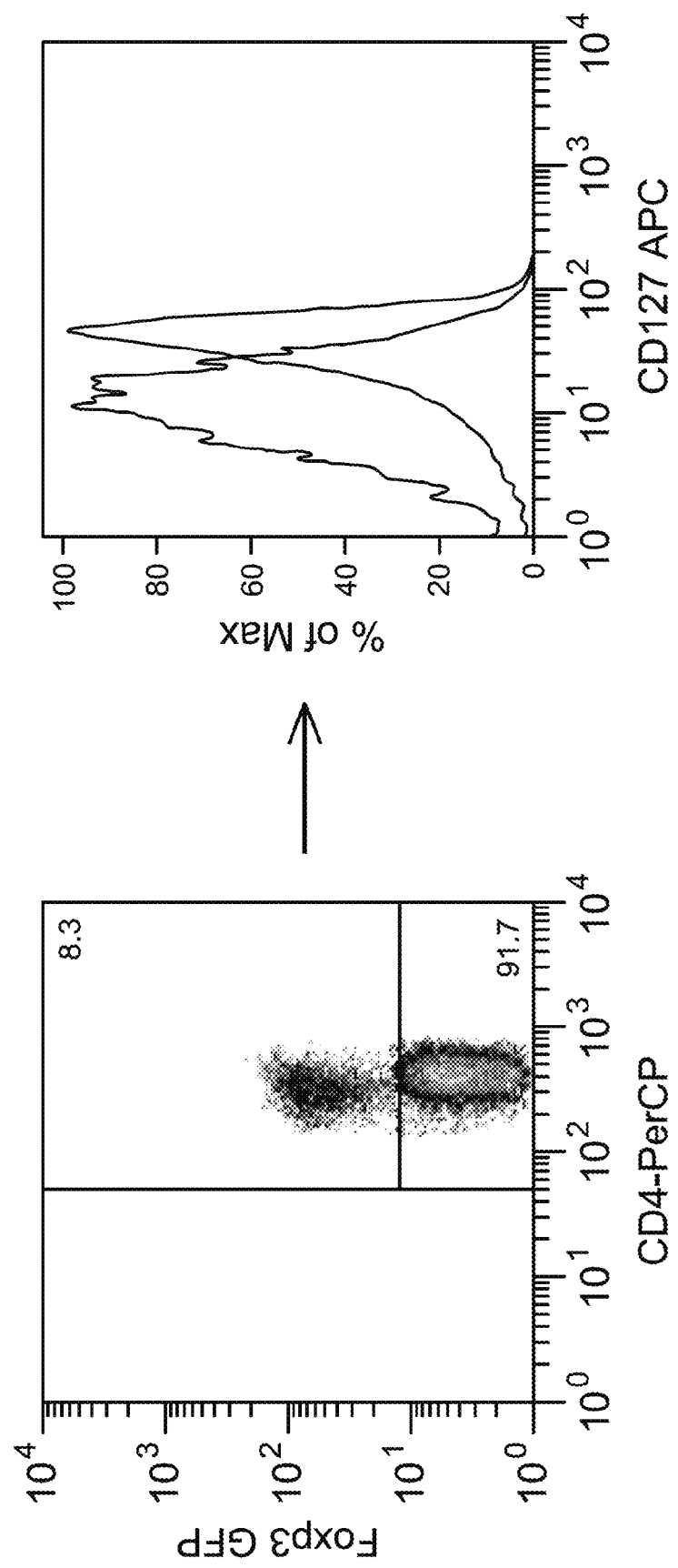
FIGS. 3A-3B. Expression of FoxP3 on different $CD4^+$ $CD127^{+/-}$ mouse T cell subsets. (3A) Mouse spleen and lymph node cells were stained for cell surface expression of CD4 and CD127. For analysis, the spleen cells from FoxP3-GFP mice were gated on lymphocytes (based on forward and side light scatter) and analyzed for CD127 and FoxP3 (GFP)
Figure 3B:
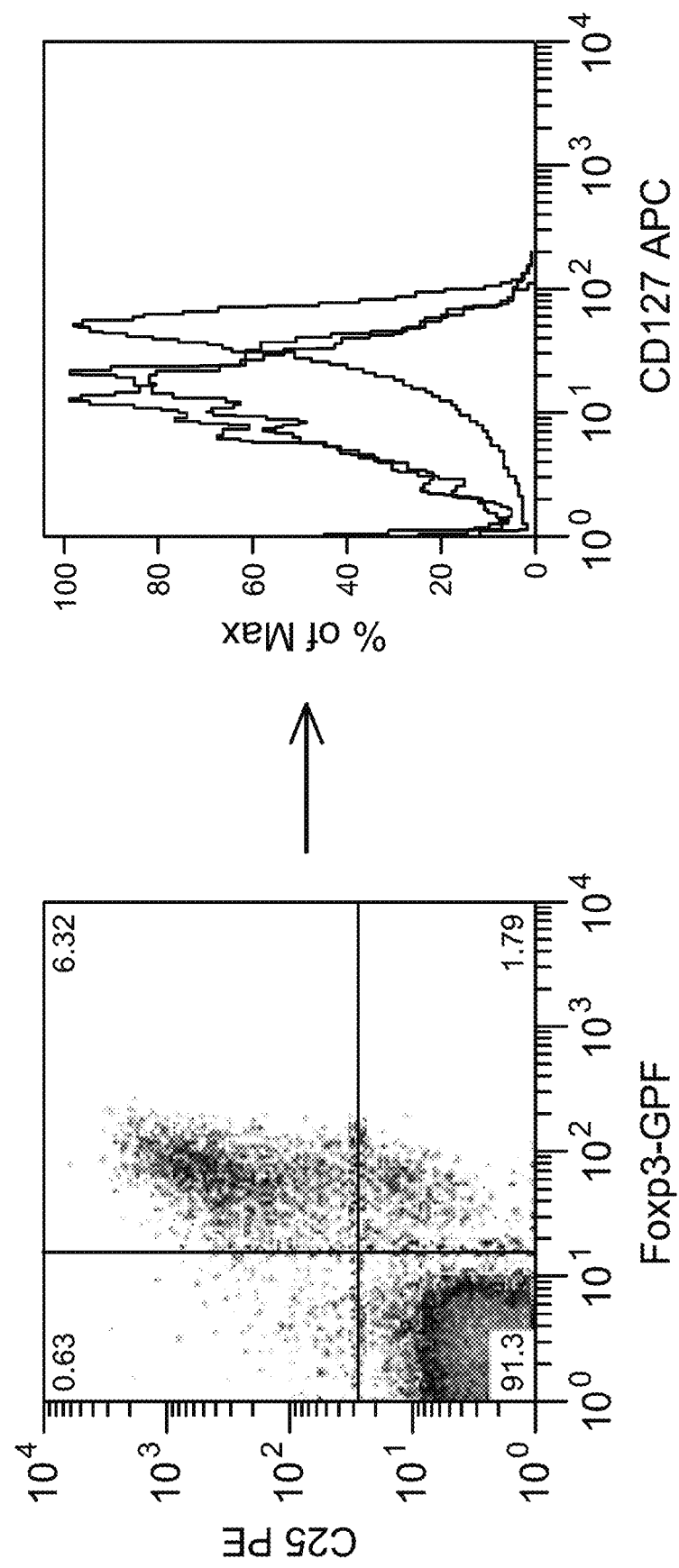

As predicted by the gene expression studies, the majority of the CD4$^+$CD25$^+$ cells, especially the CD4$^+$CD25$^{hi}$ T cells had low expression of CD127 (FIG. 2a). However, not all of the CD4$^+$CD127$^{lo/-}$ T cells were CD25$^+$. In fact, a significant percentage of CD4$^+$CD127$^{lo/-}$ T cells (15.8% in this individual) were CD25 negative. That said, the majority of the CD4$^+$CD25$^-$ T cells were CD127 bright (73.8%) accounting for the differential expression observed in the gene array analyses. More importantly, flow cytometric analysis of FoxP3 expression in CD127 positive and negative T cell subsets showed that the majority of FoxP3$^+$ T cells were in the CD127$^{lo/-}$ T cell subset (FIG. 2b). Interestingly, the relative expression of CD127 was inversely correlated with FoxP3 with the highest FoxP3-expressing CD4$^+$ T cells expressing the lowest levels of CD127. These results were uniformly observed in >20 different individuals examined. In fact, similar results were observed in mice. CD4$^+$ T cells isolated for FoxP3-GFP knock-in mice were stained for CD127 (36, 38). The vast majority of the mouse CD4$^+$FoxP3$^+$ T cells were CD127$^{lo/-}$ (FIG. 3a). Additional analyses of these mice showed that CD4$^+$CD25$^+$ FoxP3$^+$ Tregs were CD127$^{lo/-}$, however, like in humans, CD127 was a better marker than CD25 since all the CD4$^+$ T cells were CD127$^{lo/-}$ independent of CD25 expression (FIG. 3b).

Further studies were conducted to determine the relationship of CD4, CD127, FoxP3 and CD25 using multiparameter flow cytometry (FIG. 4). The overwhelming majority of CD4$^+$CD25$^+$ CD127$^{lo/-}$ T cells express FoxP3 (94% this individual) (FIG. 4a). However, a significant percentage of CD4$^+$CD25$^-$CD127$^{lo/-}$ cells are also FoxP3$^+$ (35% in this individual) although the mean fluorescence is often less than the CD4$^+$CD25$^{hi}$ cells. In sharp contrast, there were few FoxP3+ T cells in the CD4+CD127+ subset except a small percentage among those that expressed CD25. Thus, in spite of the fact that CD127+ T cells accounted for about 90% of the CD4+ T cells in this individual (FIG. 4b). Interestingly, back-gating of the CD4+CD127+FoxP3+ subset showed that the expression of CD25 in these T cells was intermediate and distinct from the CD25$^{hi}$ subset described as "classic" Tregs (data not shown) suggesting they may be a transitional cell. Similar results were observed in PBMCs obtained from 10 healthy donors stained for cell surface expression of CD4, CD127, CD25 followed by intracellular staining with FoxP3-specific mAb (FIG. 4c). Examination of multiple individuals confirmed that the majority of the CD4+FoxP3+ T cells were within the CD25+ CD127$^{lo/-}$ subset, however, in some individuals a significant percentage of the CD25− CD127$^{lo/-}$ and/or CD25+ CD127+ T cells were FoxP3+. Thus, CD127 is a better cell surface marker than CD25 for the identification of CD4+FoxP3+ T cells, however, the best combination of cell surface markers is CD4+CD25+ CD127$^{lo/-}$ which accounts for approximately 80% of the FoxP3+ depending on the individual. Thus, a broad gating strategy of CD4+CD25+ CD127$^{lo/-}$ results in a highly purified FoxP3+ T cell population as compared to the other subsets (FIG. 4d).

Example 13. ChIP-Chip Analysis of FoxP3 Interaction with CD127

The data clearly showed a "general" relationship between FoxP3 expression and CD127 down-regulation. However, we were struck with the apparently inverse correlation between FoxP3 and CD127 protein (FIG. 2b). These results suggested that there may be a direct structural relationship between the transcription factor, FoxP3, and CD127 transcription. This was especially attractive given previous studies suggesting that FoxP3 represses gene expression (39). Chromatin (Ch) immunoprecipitation (IP) of transcription factor-bound genomic DNA followed by microarray hybridization (chip) of IP-enriched DNA is a new technology that allows genome-wide analysis of transcription factor binding. ChIP-chip data are different than classical microarray gene expression data obtained by measuring mRNA levels in that it examines direct control of gene transcription not just potentially indirect downstream regulation.

We performed ChIP-chip experiments on anti-CD3/anti-CD28-expanded CD4+CD25$^{hi}$ human Tregs (37). Anti-FoxP3 or control rabbit Ig was used to precipitate cross-linked protein-DNA complexes from nuclear lysates. The cross-linking of the immunoprecipitated material was removed, protease-treated, and the DNA was purified and amplified. The resultant material was hybridized to the whole genome using GeneChip® Human Tiling 1.0R Array Set (Affymetrix 900774) to identify the locations of binding sites for FoxP3. Statistical analysis was performed to determine sites that were selectively associated with FoxP3 protein and not rabbit Ig.

The IL-7R promoter region scored among the various sites bound by the FoxP3 protein immunoprecipitates (data not shown). The CD127 promoter binding was confirmed by qPCR. Oligonucleotide primers spanning the CD127 promoter region were used on anti-FoxP3 immunoprecipitated DNA from CD4+CD25$^{hi}$ human Tregs (FIGS. 5a-5b). There was a strong enrichment of CD127 DNA amplified from the anti-FoxP3 immunoprecipitates as compared to the rabbit Ig immunoprecipitates specifically in the IL-7R promoter region but not other DNA sequences surrounding this area on the genome. These data support the direct regulation of CD127 by FoxP3.

Example 14. Suppression of Allogeneic Mixed Lymphocyte Response (MLR) Using Different CD4+ T Cell Subsets Although the low expression of CD127 correlated with FoxP3 expression, a number of studies have questioned whether FoxP3 is always a marker of Tregs in humans. Thus, we examined the ability of CD4+CD25+ CD127$^{lo/-}$ T cells and other subsets to suppress an allogeneic MLR. PBMCs were sorted into 4 subsets based on CD127, CD25 and CD4 expression. First, we examined the ability of the individual subsets to respond to the allogeneic APCs. As can be seen in FIG. 6, as previously reported, the CD4+CD25$^{hi}$ T cell subset was anergic when stimulated with alloantigen consistent with the fact that these cells were FoxP3+ and comprise the "classical" Treg subset. Similarly, neither of the CD127$^{lo/-}$ subsets, CD25+ or CD25−CD4+ T cells or the bulk CD4+CD127$^{lo/-}$ T cells responded in the allogeneic MLR suggesting that like the CD4+CD25$^{hi}$ T cells, these cells were anergic (37). In contrast, the CD4+CD127+ T cell subset responded normally to alloantigen consistent with publications suggesting that these cells represented naive and memory T cell compartments (32, 34, 40). Similar results were observed when the cells were stimulated with anti-CD3 and anti-CD28 (data not shown) suggesting that like "classical" Treg subsets, the FoxP3-expressing cells were anergic. Next, the various subpopulations were added to an allogeneic MLR and compared for their ability to suppress T cell proliferation. The CD4+CD127$^{lo/-}$ CD25+ T cell subset suppressed the MLR as well or better that CD4+CD25$^{hi}$ T cells (FIGS. 7a-7b). This is significant since this subset represents at least 3-fold more CD4+ T cells including both CD25 intermediate and negative subsets. Thus, CD127 is more that just another marker of CD4+ CD25$^{hi}$ Tregs but allows for the identification and isolation of a significantly more inclusive suppressive T cell subset. In fact, suppressive activity was independent of CD25 as both the CD4+CD127$^{lo/-}$ CD25+ and CD4+CD127$^{lo/-}$ CD25− T cell subsets suppressed the MLR, although in multiple studies the CD4+CD127$^{lo/-}$ CD25+ T cells suppressed responses more effectively than the CD4+CD127$^{lo/-}$ CD25− T cell subset especially at lower Treg:Tresp ratios. These results are consistent with the lower percentage and level of expression of FoxP3+ cells in this T cell subset. Neither of the CD127+ cells suppressed the MLR reproducibly (n=9). As can be seen, the CD127 marker is the most discriminating in showing suppressor cell activity. These results indicated that CD127 is a sufficient marker for defining the CD4+ regulatory T cell subset. To demonstrate this directly, PBMCs were sorted based only on the expression of CD4 and CD127 and examined in an allogeneic MLR. The CD4+CD127$^{lo/-}$ T cell subset were anergic (data not shown) and suppressed the MLR almost as efficiently as the CD4+ CD127$^{lo}$-CD25+ or CD4+CD25$^{hi}$ T cells.

In addition, the Applicants compared gene expression profiles for a gene array in which mRNA from various T cell subsets were analyzed on an Affy whole genome chip and assessed for level of expression. CD4+CD127$^{lo}$CD25+ cells have closely the same overall fingerprint as the classical CD4+CD25$^{bright}$ cells which differs from CD25− cells (data not shown), including, particularly with respect to selected T-reg marker TNF-R75, CTLA4, IL2RB, CD58, and CCR6 gene expression (not shown).

Example 15. Frequency of CD4$^+$CD25$^+$ CD127$^{lo/-}$ T Cells from Patients with T1D Previous studies have suggested that Treg numbers might be deficient in patients with Type 1 diabetes (24). To investigate quantitative differences in the Treg populations in patients with T1D versus control subjects, peripheral blood T cells were stained with CD4, CD25, CD127 and FoxP3. The frequency of CD4$^+$CD25$^+$ CD127$^{lo/-}$ Tregs was not significantly different between T1D (mean 66.1%, Std 11.3%, range 53.7-82.8%) and control subjects (mean 65.5%, Std 8.66%, range 45.4-76.2%) (FIG. 8). Although the percentages of FoxP3$^+$ T cells among the CD4$^+$ T cells in the two groups were higher than those reported for the CD4$^+$CD25$^{hi}$ Treg subset, the patterns matched those previously observed. These results are in contrast with some reports that found differences in the percentage of CD4$^+$ CD25$^{hi}$ T cells in T1D subjects when analyzed as a percentage of CD4$^+$ T cells.

Example 16. CD4$^+$CD127$^{lo/-}$ Tregs are Suppressive and have Treg Phenotype Flow cytometric analyses showed that only 30-40% of the isolated CD4+CD127$^{lo}$ cells expressed Foxp3 at the beginning of culture, with even less Foxp3 expression (both based on percentage and MFI (mean fluorescence intensity)) after expansion. These results raised the question as to the functional activity of the Foxp3 negative T cells in the culture. As a first approach to determining the functional potential of the different cells grown in the culture, we separated CD4+ CD127lo cells and cultured for 14 days with anti-CD3/anti-CD28+IL-2 plus/minus rapamycin. The cells expanded best in the absence of rapamycin and when re-stimulated with the mAb and IL-2 cocktail on day 9. The cell expanded with RAPA had the highest levels of Foxp3 and percentage of Foxp3+ cells. The majority of Foxp3$^-$ cells were CD25lo versus Foxp3+ cells in the same culture.

We next compared CD4$^+$CD127$^{lo}$ suppression for cells expanded in the presence of IL-2 or IL-2 rapamycin. At 14 days, expanded cells were separated and added to a CFSE (carboxyfluorescein succinimidyl ester) suppression assay. Interestingly, after culture both populations suppressed but those grown in Rapamycin suppressed better (see FIG. 12). This correlated with increased FoxP3 expression suggesting that FoxP3 expression was linked to suppressive activity but not essential for suppressor cell activity by the expanded cells. In this regard, it should be noted in FIG. 7 that the fresh CD4$^+$CD127$^{lo}$CD25$^-$ T cells were suppressive supporting the possibility that CD127, not Foxp3, is a better marker for suppressor cell activity in this assay.

We next compared CD4$^+$CD127$^{lo}$ suppression based upon CD25 separation after expansion (see, FIGS. 13a-13b). At 14 days, expanded cells were separated into CD25$^+$ (middle column) and CD25$^-$ (right column) subsets and added to a CFSE suppression assay. Interestingly, after culture both populations suppressed equivalently suggesting that CD25 expression was not essential to confer suppressive activity on the expanded cells. However, we were unable to rule out whether the cells that suppressed in these cultures were derived from CD25$^+$ cells or had down-regulated CD25 during the culture.

We also examined FoxP3 and CD127 expression and Treg function of fresh CD4$^+$CD127$^{lo}$ FoxP3$^+$ and FoxP3$^-$ mouse T cells. These studies in mouse Tregs have confirmed our observations and showed that only the FoxP3$^+$CD127$^-$ cells suppress before expansion while after culture both the FoxP3$^+$ and FoxP3$^-$ populations suppress effectively. This result indicates that CD127 is the best marker and that CD127$^{lo}$ FoxP3$^+$ cells can "educate" FoxP3$^-$ cells to become suppressors in vitro.

Discussion of the Examples

The above findings raise several critical issues. First, since the majority of CD4$^+$FoxP3$^+$ T cells may fall outside the typical gate for human Tregs, studies used for functional and immunophenotypic analyses are potentially missing a large number of putative Tregs. This has important implications in determining quantitative differences in patients with a variety of diseases. Second, the fact that CD4$^+$ CD127$^{lo/-}$ CD25$^-$ T cells suppress an allogeneic MLR call into question those studies suggesting that FoxP3 is not a "good" marker for Treg activity. It may be that FoxP3 is an excellent marker and the small populations that arise during normal T cell activation are indeed adaptive regulatory T cells expanding as a consequence of sub-optimal or supra-optimal TCR signaling. It should be emphasized, however, that not all FoxP3$^+$ T cells are necessarily Tregs and their activity may depend on the level of FoxP3 expression and isoforms of the protein expressed. However, these CD4$^+$ CD25$^+$ CD127$^{lo/-}$, once isolated, may be treated in vivo with TGFβ or other factors to enhance Treg function in these cells. Third, efforts to select Tregs for in vitro expansion may be hindered by the underestimate of Tregs in any separation strategy based on CD25 expression. The ability to identify and select a significantly greater number of Tregs circulating in the peripheral blood of humans, especially those with autoimmune diseases, is likely to make it easier to expand sufficient cell numbers for immunotherapy. Finally, the identification of CD127 as a marker that distinguishes effector/memory from regulatory T cells indicates that anti-CD127 therapy might be appropriate for the treatment of autoimmune diseases such as Type 1 Diabetes, Systemic Lupus Erythematosis, or Multiple Sclerosis.

The identification of CD127 as a useful marker can be related to genetic observations. First, microarray analysis of mRNA from individual T cell subsets showed that CD127 was expressed at significantly lower levels in CD4$^+$CD25$^{hi}$ versus CD4$^+$CD25$^-$ T cells. Unlike the majority of activated T cells, which rapidly re-express CD127 and memory T cells that express high levels of CD127, the Treg population remains CD127$^{lo/-}$. There may be two reasons for this. First, Tregs may be constantly undergoing antigenic stimulation which is CD28-dependent resulting in continued signaling that shuts down CD127 mRNA transcription. In this regard, it is interesting to note that activation of naïve T cells by anti-CD3 plus anti-CD28 but not anti-CD3 alone led to a rapid down-regulation of CD127 (J. Esensten, A. Weiss and J. A. Bluestone, unpublished data) suggesting that CD28 signals are uniquely involved in regulating CD127 down-regulation. Alternatively, and not mutually exclusive, is the possibility that FoxP3 expression in this T cell subset controls CD127 expression. There are a number of reasons to think that this may be the case As illustrated in the flow cytometric staining profiles, the more FoxP3 expression, the less CD127 (FIG. 2b). In addition, over-expression of FoxP3 in transgenic mice results in a uniformly CD127$^{lo/-}$ population of cells with suppressive activity. Finally, data generated using CHiP analysis (first by ChIP-Chip followed by ChIP-qPCR) suggested that the CD127 promoter is a target for FoxP3 binding. Whether the low expression of CD127 is a consequence of constant antigen exposure in vivo or FoxP3 upregulation resulting in CD127 gene repression are not mutually exclusive.

The $CD4^+CD127^{lo/-}CD25^-$ T cells suppress quite effectively although the percentage of $FoxP3^+$ T cells in this subset can be quite variable. These results suggested that the CD127 marker may be useful in identifying different subtypes of regulatory T cells including Tr1 and TH3 cells. In this regard, there are currently a number of settings, including the treatment of humans with T1D with anti-CD3 that induces T cells with a regulatory phenotype (11, 31, 42, 43). These studies, which mimic similar results in Treg-deficient mice treated with non-mitogenic anti-CD3 (10), indicate that it may be possible to identify an "adaptive" Treg response using CD127 as a biomarker in addition to lower CD25 expression previously observed on these cells.

One of the more intriguing aspects of the results is the seeming dichotomy in cytokine receptor expression in memory T cells versus Tregs. Whereas a high percentage of Tregs now appear to be IL-7R low and IL-2R positive, memory T cells have the opposite phenotype, expressing high levels of IL-7R and low levels of IL-2R. The functional basis for this differential expression is unclear but it may reflect the evolution of distinct pathways for cell survival and expansion of these T cell subsets. For instance, it is possible that regulatory T cells may play a critical role in normal homeostasis. Thus, the cells attempt to regulate the earliest immune perturbation that may occur in the absence of a pathogenic response. Since IL-2 is an "early cytokine" produced rapidly by activate T cells in the draining lymph nodes, IL-2 may be a critical signal for awakening the Treg response which can effectively suppress T cell expansion in these lymphoid tissues (44). In contrast, IL-7 is commonly produced locally in sites of inflammation leading to increased survival and expansion of effector cells. If this localized IL-7 expression promoted Treg expansion it might be counterproductive. Moreover, avoiding competition for the use of the common γ chain by these receptors would enhance the functionality of the cytokine function. Finally, it should be noted that the situation might be quite distinct in thymus when all the pre-T and immature T cells are $CD127^+$ and $CD25^+$. At this stage in development other factors might come into play to determine the differentiation pathways that determine whether a T cell become a Treg or a naive conventional T cell.

Several studies have examined the number and function of Treg cells in humans with autoimmune diseases. In some settings, such as Multiple Sclerosis, Type 1 Diabetes and autoimmune polyglandular syndrome II, the data, based on the number and function of $CD4^+CD25^{hi}$ Tregs, suggest that there are either fewer Tregs or less functional Tregs in diseased individuals (24, 45-47). However, in Type 1 Diabetes and other autoimmune diseases, there have been contradictory results (25, 48). In the present study, we re-evaluated Tregs in patients with T1D as compared to normal individuals. Using the new markers, FoxP3 and CD127, we analyzed the frequency of $CD4^+CD25^+$ $FoxP3^+$ $CD127^{lo/-}$ T cells and the function of sorted $CD4^+CD25^+$ $CD127^{lo/-}$ to alloantigen stimulation. In this study, it is clear that human Tregs as defined by CD4, CD25, CD127 and FoxP3 expression are present within the same range of percentages as control individuals with no autoimmunity. Moreover, the functionality of the Tregs isolated from the patients with T1D cannot be distinguished from healthy control subjects. We cannot explain the basis for differences between our studies and those of others in the T1D field. It had been suggested that the discrepancy might be due to subtle differences in flow cytometry-based techniques for cell separation or different mAbs used. However, our use of distinct markers that identify the overwhelming bulk of Tregs in human peripheral blood is likely to be a more definitive assessment of the Treg numbers and functional potential in this patient population. Lastly, it is interesting to note that several of the T1D patients had high Tregs numbers as compared to the bulk of the control and T1D subjects. This is consistent with some studies in other autoimmune diseases where the frequency of $CD4^+CD25^{hi}$ T cells was reported to be increased as compared to controls. Moreover, these results fit with mouse studies demonstrating increased Treg number at the time of T1D disease onset as well as other immune disease settings (J. Adams, Q. Tang and J. A. Bluestone, unpublished data). We hypothesize that rather than a Treg-deficiency being the cause of disease precipitation, there is actually increased Treg activity in an attempt to stem the losing battle being waged against the increasingly aggressive effector cells that may indeed become more Treg resistant.

REFERENCES

1. Sakaguchi, S., N. Sakaguchi, J. Shimizu, S. Yamazaki, T. Sakihama, M. Itoh, Y. Kuniyasu, T. Nomura, M. Toda, and T. Takahashi. 2001. Immunologic tolerance maintained by $CD25^+$ $CD4^+$ regulatory T cells: their common role in controlling autoimmunity, tumor immunity, and transplantation tolerance. *Immunol Rev* 182:18-32.
2. Chatenoud, L., B. Salomon, and J. A. Bluestone. 2001. Suppressor T cells—they're back and critical for regulation of autoimmunity! *Immunol Rev* 182:149-163.
3. Wood, K. J., and S. Sakaguchi. 2003. Regulatory T cells in transplantation tolerance. *Nat Rev Immunol* 3:199-210.
4. Singh, B., S. Read, C. Asseman, V. Malmstrom, C. Mottet, L. A. Stephens, R. Stepankova, H. Tlaskalova, and F. Powrie. 2001. Control of intestinal inflammation by regulatory T cells. *Immunol Rev* 182:190-200.
5. Curotto de Lafaille, M. A., and J. J. Lafaille. 2002. CD4(+) regulatory T cells in autoimmunity and allergy. *Curr Opin Immunol* 14:771-778.
6. Tang, Q., K. J. Henriksen, M. Bi, E. B. Finger, G. Szot, J. Ye, E. L. Masteller, H. McDevitt, M. Bonyhadi, and J. A. Bluestone. 2004. In vitro-expanded antigen-specific regulatory T cells suppress autoimmune diabetes. *J Exp Med* 199:1455-1465.
7. von Boehmer, H. 2005. Mechanisms of suppression by suppressor T cells. *Nat Immunol* 6:338-344.
8. Shevach, E. M. 2002. CD4+ CD25+ suppressor T cells: more questions than answers. *Nat Rev Immunol* 2:389-400.
9. Thornton, A. M., C. A. Piccirillo, and E. M. Shevach. 2004. Activation requirements for the induction of CD4+ CD25+ T cell suppressor function. *Eur J Immunol* 34:366-376.
10. Belghith, M., J. A. Bluestone, S. Barriot, J. Megret, J. F. Bach, and L. Chatenoud. 2003. TGF-beta-dependent mechanisms mediate restoration of self-tolerance induced by antibodies to CD3 in overt autoimmune diabetes. *Nat Med* 9:1202-1208.
11. Apostolou, I., and H. von Boehmer. 2004. In vivo instruction of suppressor commitment in naive T cells. *J Exp Med* 199:1401-1408.

12. Bluestone, J. A., and A. K. Abbas. 2003. Natural versus adaptive regulatory T cells. *Nat Rev Immunol* 3:253-257.
13. Levings, M. K., and M. G. Roncarolo. 2005. Phenotypic and functional differences between human CD4+ CD25+ and type 1 regulatory T cells. *Curr Top Microbiol Immunol* 293:303-326.
14. Weiner, H. L. 2001. Oral tolerance: immune mechanisms and the generation of Th3-type TGF-beta-secreting regulatory cells. *Microbes Infect* 3:947-954.
15. Tarbell, K. V., S. Yamazaki, K. Olson, P. Toy, and R. M. Steinman. 2004. CD25+ CD4+ T cells, expanded with dendritic cells presenting a single autoantigenic peptide, suppress autoimmune diabetes. *J Exp Med* 199:1467-1477.
16. Baecher-Allan, C., J. A. Brown, G. J. Freeman, and D. A. Hafler. 2001. CD4+CD25high regulatory cells in human peripheral blood. *J Immunol* 167:1245-1253.
17. Takahashi, T., Y. Kuniyasu, M. Toda, N. Sakaguchi, M. Itoh, M. Iwata, J. Shimizu, and S. Sakaguchi. 1998. Immunologic self-tolerance maintained by CD25+ CD4+ naturally anergic and suppressive T cells: induction of autoimmune disease by breaking their anergic/suppressive state. *Int Immunol* 10:1969-1980.
18. Shimizu, J., S. Yamazaki, T. Takahashi, Y. Ishida, and S. Sakaguchi. 2002. Stimulation of CD25(+)CD4(+) regulatory T cells through GITR breaks immunological self-tolerance. *Nat Immunol* 3:135-142.
19. Salomon, B., and J. A. Bluestone. 2001. Complexities of CD28/B7: CTLA-4 costimulatory pathways in autoimmunity and transplantation. *Annu Rev Immunol* 19:225-252.
20. McHugh, R. S., M. J. Whitters, C. A. Piccirillo, D. A. Young, E. M. Shevach, M. Collins, and M. C. Byrne. 2002. CD4(+)CD25(+) immunoregulatory T cells: gene expression analysis reveals a functional role for the glucocorticoid-induced TNF receptor. *Immunity* 16:311-323.
21. Kataoka, H., S. Takahashi, K. Takase, S. Yamasaki, T. Yokosuka, T. Koike, and T. Saito. 2005. CD25(+)CD4(+) regulatory T cells exert in vitro suppressive activity independent of CTLA-4. *Int Immunol* 17:421-427.
22. Tang, Q., E. K. Boden, K. J. Henriksen, H. Bour-Jordan, M. Bi, and J. A. Bluestone. 2004. Distinct roles of CTLA-4 and TGF-beta in CD4+CD25+ regulatory T cell function. *Eur J Immunol* 34:2996-3005.
23. Ronchetti, S., O. Zollo, S. Bruscoli, M. Agostini, R. Bianchini, G. Nocentini, E. Ayroldi, and C. Riccardi. 2004. GITR, a member of the TNF receptor superfamily, is costimulatory to mouse T lymphocyte subpopulations. *Eur J Immunol* 34:613-622.
24. Kukreja, A., G. Cost, J. Marker, C. Zhang, Z. Sun, K. Lin-Su, S. Ten, M. Sanz, M. Exley, B. Wilson, S. Porcelli, and N. Maclaren. 2002. Multiple immunoregulatory defects in type-1 diabetes. *J Clin Invest* 109:131-140.
25. Putnam, A. L., F. Vendrame, F. Dotta, and P. A. Gottlieb. 2005. CD4+CD25high regulatory T cells in human autoimmune diabetes. *J Autoimmun* 24:55-62.
26. Fontenot, J. D., M. A. Gavin, and A. Y. Rudensky. 2003. Foxp3 programs the development and function of CD4+ CD25+ regulatory T cells. *Nat Immunol* 4:330-336.
27. Khattri, R., T. Cox, S. A. Yasayko, and F. Ramsdell. 2003. An essential role for Scurfin in CD4+CD25+ T regulatory cells. *Nat Immunol* 4:337-342.
28. Gambineri, E., T. R. Torgerson, and H. D. Ochs. 2003. Immune dysregulation, polyendocrinopathy, enteropathy, and X-linked inheritance (IPEX), a syndrome of systemic autoimmunity caused by mutations of FOXP3, a critical regulator of T-cell homeostasis. *Curr Opin Rheumatol* 15:430-435.
29. Hori, S., T. Nomura, and S. Sakaguchi. 2003. Control of regulatory T cell development by the transcription factor Foxp3. *Science* 299:1057-1061.
30. Ziegler, S. F. 2006. FOXP3: Of Mice and Men. *Annu Rev Immunol* 24:209-226.
31. Bisikirska, B., J. Colgan, J. Luban, J. A. Bluestone, and K. C. Herold. 2005. TCR stimulation with modified anti-CD3 mAb expands CD8+ T cell population and induces CD8+CD25+ Tregs. *J Clin Invest* 115:2904-2913.
32. Fuller, M. J., D. A. Hildeman, S. Sabbaj, D. E. Gaddis, A. E. Tebo, L. Shang, P. A. Goepfert, and A. J. Zajac. 2005. Cutting edge: emergence of CD127high functionally competent memory T cells is compromised by high viral loads and inadequate T cell help. *J Immunol* 174:5926-5930.
33. Boettler, T., E. Panther, B. Bengsch, N. Nazarova, H. C. Spangenberg, H. E. Blum, and R. Thimme. 2006. Expression of the interleukin-7 receptor alpha chain (CD127) on virus-specific CD8+ T cells identifies functionally and phenotypically defined memory T cells during acute resolving hepatitis B virus infection. *J Virol* 80:3532-3540.
34. Huster, K. M., V. Busch, M. Schiemann, K. Linkemann, K. M. Kerksiek, H. Wagner, and D. H. Busch. 2004. Selective expression of IL-7 receptor on memory T cells identifies early CD40L-dependent generation of distinct CD8+ memory T cell subsets. *Proc Natl Acad Sci USA* 101:5610-5615.
35. Li, J., G. Huston, and S. L. Swain. 2003. IL-7 promotes the transition of CD4+ effectors to persistent memory cells. *J Exp Med* 198:1807-1815.
36. Fontenot, J. D., J. P. Rasmussen, L. M. Williams, J. L. Dooley, A. G. Farr, and A. Y. Rudensky. 2005. Regulatory T cell lineage specification by the forkhead transcription factor foxp3. *Immunity* 22:329-341.
37. Earle, K. E., Q. Tang, X. Zhou, W. Liu, S. Zhu, M. L. Bonyhadi, and J. A. Bluestone. 2005. In vitro expanded human CD4+CD25+ regulatory T cells suppress effector T cell proliferation. *Clin Immunol* 115:3-9.
38. Fontenot, J. D., J. L. Dooley, A. G. Farr, and A. Y. Rudensky. 2005. Developmental regulation of Foxp3 expression during ontogeny. *J Exp Med* 202:901-906.
39. Schubert, L. A., E. Jeffery, Y. Zhang, F. Ramsdell, and S. F. Ziegler. 2001. Scurfin (FOXP3) acts as a repressor of transcription and regulates T cell activation. *J Biol Chem* 276:37672-37679.
40. Okada, E., M. Yamazaki, M. Tanabe, T. Takeuchi, M. Nanno, S. Oshima, R. Okamoto, K. Tsuchiya, T. Nakamura, T. Kanai, T. Hibi, and M. Watanabe. 2005. IL-7 exacerbates chronic colitis with expansion of memory IL-7Rhigh CD4+ mucosal T cells in mice. *Am J Physiol Gastrointest Liver Physiol* 288:G745-754.
41. Baecher-Allan, C., E. Wolf, and D. A. Hafler. 2005. Functional analysis of highly defined, FACS-isolated populations of human regulatory CD4+ CD25+ T cells. *Clin Immunol* 115:10-18.
42. Herold, K. C., W. Hagopian, J. A. Auger, E. Poumian-Ruiz, L. Taylor, D. Donaldson, S. E. Gitelman, D. M. Harlan, D. Xu, R. A. Zivin, and J. A. Bluestone. 2002. Anti-CD3 monoclonal antibody in new-onset type 1 diabetes mellitus. *N Engl J Med* 346:1692-1698.
43. Chen, W., K. C. Herold, and J. A. Bluestone. 2005. Achieving antigen-specific tolerance in diabetes: regulating specifically. *Int Rev Immunol* 24:287-305.

44. Tang, Q., J. Y. Adams, A. J. Tooley, M. Bi, B. T. Fife, P. Serra, P. Santamaria, R. M. Locksley, M. F. Krummel, and J. A. Bluestone. 2006. Visualizing regulatory T cell control of autoimmune responses in nonobese diabetic mice. *Nat Immunol* 7:83-92.

45. Cox, A. L., S. A. Thompson, J. L. Jones, V. H. Robertson, G. Hale, H. Waldmann, D. A. Compston, and A. J. Coles. 2005. Lymphocyte homeostasis following therapeutic lymphocyte depletion in multiple sclerosis. *Eur J Immunol* 35:3332-3342.

46. Viglietta, V., C. Baecher-Allan, H. L. Weiner, and D. A. Hafler. 2004. Loss of functional suppression by CD4+ CD25+ regulatory T cells in patients with multiple sclerosis. *J Exp Med* 199:971-979.

47. Kriegel, M. A., T. Lohmann, C. Gabler, N. Blank, J. R. Kalden, and H. M. Lorenz. 2004. Defective suppressor function of human CD4+ CD25+ regulatory T cells in autoimmune polyglandular syndrome type II. *J Exp Med* 199:1285-1291.

48. de Kleer, I. M., L. R. Wedderburn, L. S. Taams, A. Patel, H. Varsani, M. Klein, W. de Jager, G. Pugayung, F. Giannoni, G. Rijkers, S. Albani, W. Kuis, and B. Prakken. 2004. CD4+CD25bright regulatory T cells actively regulate inflammation in the joints of patients with the remitting form of juvenile idiopathic arthritis. *J Immunol* 172:6435-6443.

49. Oberley, M. J., J. Tsao, P. Yau, and P. J. Farnham. 2004. High-throughput screening of chromatin immunoprecipitates using CpG-island microarrays. *Methods Enzymol* 376:315-334.

50. Cawley, S., S. Bekiranov, H. H. Ng, P. Kapranov, E. A. Sekinger, D. Kampa, A. Piccolboni, V. Sementchenko, J. Cheng, A. J. Williams, R. Wheeler, B. Wong, J. Drenkow, M. Yamanaka, S. Patel, S. Brubaker, H. Tammana, G. Helt, K. Struhl, and T. R. Gingeras. 2004. Unbiased mapping of transcription factor binding sites along human chromosomes 21 and 22 points to widespread regulation of noncoding RNAs. *Cell* 116:499-509.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. No reference to a publication herein should be construed as an admission that such is prior art.

---

What is claimed is:

1. A method of enriching a sample comprising human T-cells for FoxP3$^+$ immunosuppressive regulatory T-cells, the method comprising:

providing the sample comprising human T-cells, wherein the sample is a peripheral blood mononuclear cell (PBMC) sample; and enriching the sample for cells expressing CD4 on their surface and being CD127$^{lo/-}$, wherein CD127$^{lo/-}$ cells have reduced or no levels of surface-expressed CD127 compared to other cells in the sample expressing greater amounts of CD127, wherein the enriching step comprises contacting the sample with a labeled anti-CD4 antibody and a labeled anti-CD127 antibody and selecting cells according to the amount of labeled anti-CD4 antibody and anti-CD127 antibody bound to them;

thereby forming a FoxP3$^+$-enriched cell population.

2. The method of claim 1, wherein the enriching comprises enriching for CD4 and CD127$^{lo/-}$ markers simultaneously.

3. The method of claim 1, wherein the enriching comprises enriching for CD4 and CD127$^{lo/-}$ markers by enriching for one of the CD4 or CD127$^{lo/-}$ markers and subsequently enriching for the other of the CD4 and CD127$^{lo/-}$ markers.

4. The method of claim 1, wherein the enriching comprises:

(a) enriching for cells expressing CD4, thereby generating a population of CD4$^+$ cells; and then (b) enriching the population of CD4$^+$ cells for cells that are CD127$^{lo/-}$.

5. The method of claim 1, wherein the labeled anti-CD4 antibody is a fluorescently labeled anti-CD4 antibody and/or the labeled anti-CD127 antibody is a fluorescently labeled anti-CD127 antibody.

6. The method of claim 1, wherein at least 10% of the FoxP3$^+$-enriched cell population is CD25$^-$ or CD25$^{lo}$ cells.

7. The method of claim 1, wherein the FoxP3$^+$-enriched cell population comprises at least 25% CD25$^+$ cells.

8. The method of claim 1, wherein the method further comprises expanding the FoxP3$^+$-enriched cell population by contacting the FoxP3$^+$-enriched cell population with a T-cell receptor (TCR) activator, a TCR costimulatory activator, and IL-2.

9. The method of claim 1, wherein CD127$^{lo/-}$ cells are cells that fall below the 50$^{th}$ percentile fluorescence intensity of cells in the sample when contacted with a fluorescently-labeled anti-CD127 antibody.

10. The method of claim 1, wherein the labeled anti-CD4 antibody is a magnetic bead-labeled anti-CD4 antibody and/or the labeled anti-CD127 antibody is a magnetic bead-labeled anti-CD127 antibody.

* * * * *